United States Patent
Zeligs et al.

(10) Patent No.: US 10,441,569 B2
(45) Date of Patent: *Oct. 15, 2019

(54) SELF-EMULSIFYING FORMULATIONS OF DIM-RELATED INDOLES

(71) Applicant: BioResponse, L.L.C., Boulder, CO (US)

(72) Inventors: Michael A. Zeligs, Boulder, CO (US); Irwin C. Jacobs, Defiance, MO (US)

(73) Assignee: BioResponse, L.L.C., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/844,365

(22) Filed: Dec. 15, 2017

(65) Prior Publication Data

US 2018/0161308 A1 Jun. 14, 2018

Related U.S. Application Data

(63) Continuation of application No. 15/094,732, filed on Apr. 8, 2016, now Pat. No. 9,918,965.

(60) Provisional application No. 62/146,216, filed on Apr. 10, 2015.

(51) Int. Cl.
*A61K 31/404* (2006.01)
*A61K 9/08* (2006.01)
(Continued)

(52) U.S. Cl.
CPC .......... *A61K 31/404* (2013.01); *A61K 9/0014* (2013.01); *A61K 9/0053* (2013.01);
(Continued)

(58) Field of Classification Search
None
See application file for complete search history.

(56) References Cited

U.S. PATENT DOCUMENTS 5,993,858 A 11/1999 Crison et al.
6,086,915 A * 7/2000 Zeligs .................. A61K 9/1652
424/439
(Continued)

FOREIGN PATENT DOCUMENTS

EP 2478904 A1 7/2012
EP 1067913 B1 8/2012
(Continued)

OTHER PUBLICATIONS

P Knekt, A Kilkkinen, H Rissanen, J Marniemi, K Saaksjarvi, M Heliovaara. "Serum vitamin D and the risk of Parkinson's disease." Archives of Neurology, vol. 67(7), Jul. 1, 2011, Pubmed Central Version, pp. 1-9. (Year: 2011).*

(Continued)

*Primary Examiner* — Isaac Shomer
(74) *Attorney, Agent, or Firm* — Jones Day

(57) ABSTRACT

Disclosed herein are self-emulsifying compositions and formulations of Diindolylmethane ("DIM") and certain derivatives of DIM, their uses and methods of making. In particular, the disclosed compositions comprise a DIM-related indole as an active agent and a carrier, wherein the carrier comprises a solvent, one or more surfactants with an HLB of greater than 7, and one or more co-surfactants with an HLB equal to or less than 7. In certain aspects of the invention, the compositions disclosed herein show improved bioavailability.

28 Claims, 6 Drawing Sheets

Figure 1:
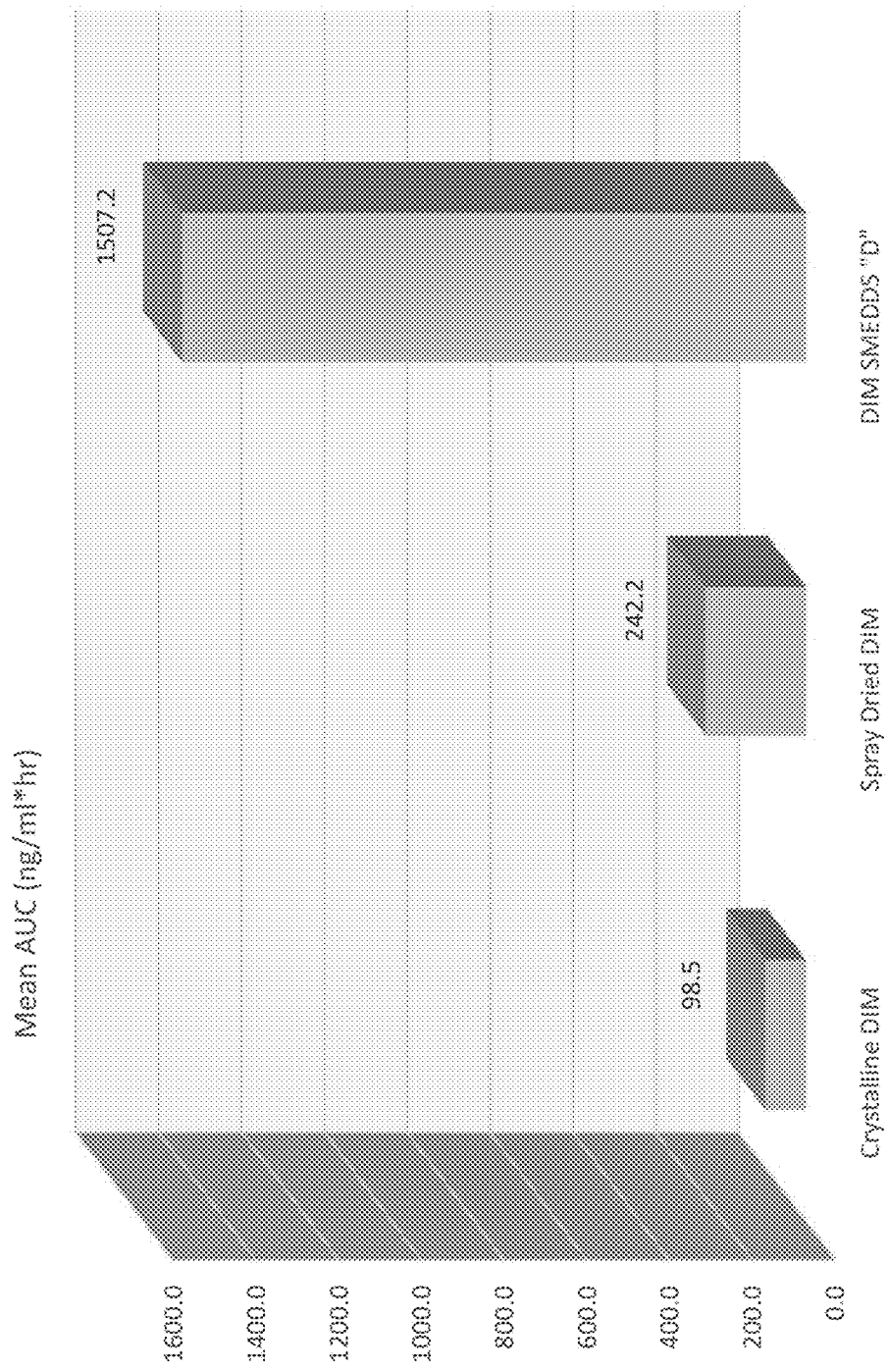

(51) Int. Cl.
  *A61K 9/14* (2006.01)
  *A61K 47/24* (2006.01)
  *A61K 47/06* (2006.01)
  *A61K 9/48* (2006.01)
  *A61K 47/10* (2017.01)
  *A61K 47/26* (2006.01)
  *A61K 47/38* (2006.01)
  *A61K 47/00* (2006.01)
  *A61K 9/10* (2006.01)
  *A61K 31/122* (2006.01)
  *A61K 31/138* (2006.01)
  *A61K 31/23* (2006.01)
  *A61K 31/275* (2006.01)
  *A61K 31/357* (2006.01)
  *A61K 31/4045* (2006.01)
  *A61K 31/59* (2006.01)
  *A61K 9/00* (2006.01)
  *A61K 31/215* (2006.01)
  *A61K 47/46* (2006.01)
  *A61K 9/107* (2006.01)
  *A61K 45/06* (2006.01)
  *A61K 47/14* (2017.01)
  *A61K 47/34* (2017.01)

(52) U.S. Cl.
  CPC .......... *A61K 9/08* (2013.01); *A61K 9/10* (2013.01); *A61K 9/107* (2013.01); *A61K 9/14* (2013.01); *A61K 9/48* (2013.01); *A61K 31/122* (2013.01); *A61K 31/138* (2013.01); *A61K 31/215* (2013.01); *A61K 31/23* (2013.01); *A61K 31/275* (2013.01); *A61K 31/357* (2013.01); *A61K 31/4045* (2013.01); *A61K 31/59* (2013.01); *A61K 45/06* (2013.01); *A61K 47/00* (2013.01); *A61K 47/06* (2013.01); *A61K 47/10* (2013.01); *A61K 47/14* (2013.01); *A61K 47/24* (2013.01); *A61K 47/26* (2013.01); *A61K 47/34* (2013.01); *A61K 47/38* (2013.01); *A61K 47/46* (2013.01); *Y02A 50/411* (2018.01)

(56) References Cited

U.S. PATENT DOCUMENTS

| | | | |
|---|---|---|---|
| 6,093,706 A | 7/2000 | Zeligs | |
| 6,323,233 B1 | 11/2001 | Wright et al. | |
| 6,369,095 B1 | 4/2002 | Firestone et al. | |
| 6,416,793 B1 | 7/2002 | Zeligs et al. | |
| 6,444,697 B2 | 9/2002 | Wright et al. | |
| 6,534,085 B1 | 3/2003 | Zeligs | |
| 6,589,975 B2 | 7/2003 | Jacobs et al. | |
| 6,656,963 B2 | 12/2003 | Firestone et al. | |
| 6,689,387 B1 | 2/2004 | Zeligs et al. | |
| 7,348,352 B2 | 3/2008 | Zeligs | |
| 7,384,971 B2 | 6/2008 | Zeligs | |
| 7,384,972 B2 | 6/2008 | Zeligs | |
| 7,709,520 B2 | 5/2010 | Safe | |
| 7,989,486 B2 | 8/2011 | Zeligs | |
| 8,080,577 B2 | 12/2011 | Zeligs | |
| 8,236,848 B2 | 8/2012 | Zeligs | |
| 8,552,052 B2 | 10/2013 | Zeligs | |
| 8,586,621 B2 | 11/2013 | Zeligs | |
| 8,697,123 B2 | 4/2014 | Kiselev et al. | |
| 8,791,150 B2 | 7/2014 | Kiselev et al. | |
| 8,835,509 B2 | 9/2014 | Kohli et al. | |
| 9,180,117 B2 | 11/2015 | Alpert | |
| 9,353,058 B2 | 5/2016 | Zeligs | |
| 9,918,965 B2* | 3/2018 | Zeligs | A61K 47/00 |
| 2002/0114830 A1 | 8/2002 | Braak | |
| 2002/0115708 A1 | 8/2002 | Safe | |
| 2003/0077297 A1 | 4/2003 | Chen et al. | |
| 2004/0043965 A1 | 3/2004 | Jong et al. | |
| 2004/0048934 A1* | 3/2004 | Gokhale | A61K 9/1075 514/786 |
| 2004/0157928 A1 | 8/2004 | Kim et al. | |
| 2004/0225004 A1 | 11/2004 | Zeligs | |
| 2004/0248901 A1 | 12/2004 | Lee et al. | |
| 2005/0037062 A1* | 2/2005 | Cote | A61K 31/135 424/450 |
| 2005/0063903 A1 | 3/2005 | Zeligs | |
| 2005/0267193 A1 | 12/2005 | Zeligs | |
| 2006/0111423 A1 | 5/2006 | Zeligs | |
| 2006/0229355 A1 | 10/2006 | Bjeldanes et al. | |
| 2006/0264497 A1* | 11/2006 | Zeligs | A61K 8/492 514/414 |
| 2006/0275358 A1* | 12/2006 | Lin | A61K 9/1075 424/451 |
| 2007/0244085 A1* | 10/2007 | Peracchia | A61K 9/0019 514/210.01 |
| 2007/0298099 A1 | 12/2007 | Peresypkin et al. | |
| 2008/0319056 A1* | 12/2008 | Liu | A61K 9/0095 514/470 |
| 2009/0060891 A1* | 3/2009 | Harris | A61K 9/1075 424/94.1 |
| 2009/0274746 A1 | 11/2009 | Gupta et al. | |
| 2009/0280199 A1* | 11/2009 | Russell | A61K 36/185 424/732 |
| 2011/0288501 A1 | 11/2011 | Gehling et al. | |
| 2012/0184590 A1 | 7/2012 | Rawjewski | |
| 2012/0289495 A1 | 11/2012 | Baloglu et al. | |
| 2013/0039979 A1* | 2/2013 | Kiselev | A61K 9/107 424/456 |
| 2013/0059883 A1 | 3/2013 | Baloglu et al. | |
| 2013/0065933 A1 | 3/2013 | Kiselev et al. | |
| 2013/0303495 A1* | 11/2013 | Dhingra | A61K 31/568 514/170 |
| 2013/0309338 A1 | 11/2013 | Yamaguchi et al. | |
| 2014/0031432 A1* | 1/2014 | Jankowski | A61K 31/122 514/681 |
| 2014/0142072 A1* | 5/2014 | Alpert | A61K 31/07 514/171 |
| 2014/0193480 A1 | 7/2014 | McWherter et al. | |
| 2014/0256740 A1 | 9/2014 | Baloglu et al. | |
| 2014/0303109 A1 | 10/2014 | Sarkar et al. | |
| 2015/0073016 A1 | 3/2015 | Gaweco et al. | |
| 2015/0087583 A1 | 3/2015 | Radhakrishnan et al. | |
| 2015/0265575 A1 | 9/2015 | Kiselev et al. | |
| 2016/0074362 A1 | 3/2016 | Alpert | |
| 2016/0101083 A1 | 4/2016 | Zeligs | |
| 2018/0280347 A1 | 10/2018 | Zeligs et al. | |

FOREIGN PATENT DOCUMENTS

| | | | | |
|---|---|---|---|---|
| WO | WO 2016/164770 A1 | 10/1916 | | |
| WO | WO-9524893 A1 * | 9/1995 | .......... | A61K 9/4858 |
| WO | WO 99/49851 | 10/1999 | | |
| WO | WO 2001/020990 A1 | 3/2001 | | |
| WO | WO 2001/020991 A1 | 3/2001 | | |
| WO | WO 2003/034992 A2 | 5/2003 | | |
| WO | WO 2004/071425 A2 | 8/2004 | | |
| WO | WO 2005/007102 A2 | 1/2005 | | |
| WO | WO 2005/107747 A2 | 11/2005 | | |
| WO | WO 2006/047716 A2 | 5/2006 | | |
| WO | WO 2006/083458 A2 | 8/2006 | | |
| WO | WO 2006/105196 A2 | 10/2006 | | |
| WO | WO 2008/057253 A2 | 5/2008 | | |
| WO | WO-2010042657 A1 * | 4/2010 | .......... | A61K 31/404 |
| WO | WO 2010/092596 | 8/2010 | | |
| WO | WO 2015/042170 A1 | 3/2015 | | |

OTHER PUBLICATIONS

V Srinivasan, DP Cardinali, US Srinivasan, C Kaur, GM Brown, DW Spence, R Hardeland, SR Pandi-Perumal. "Therapeutic potential of melatonin and its analogs in Parkinson's disease: focus on sleep and neuroprotection." Therapeutic Advances in Neurological Disorders, vol. 4(5), 2011, pp. 297-317. (Year: 2011).*

U.S. Appl. No. 15/565,381, filed Oct. 9, 2017, Zeligs et al.

(56) References Cited

OTHER PUBLICATIONS

Anderton et al., 2004, "Physiological modeling of formulated and crystalline 3,3'-diindolylmethane pharmacokinetics following oral administration in mice." Drug Metab Dispos. 32(6):632-638.
Chassaing et al., 2015, "Dietary emulsifiers impact the mouse gut microbiota promoting colitis and metabolic syndrome." Nature 519(7541):92-96.
Cherniakov et al., 2015, "Self-nano-emulsifying drug delivery systems: an update of the biopharmaceutical aspects," Expert Opin. Drug Deliv. 12(7):1121-1133.
Cho et al., 2013, "Optimized formulation of solid self-microemulsifying sirolimus delivery systems," International Journal of Nanomedicine 8:1673-1682.
Clas, 2003, "The importance of characterizing the crystal form of the drug substance during drug development." Curr Opin Drug Discov Devel. 6(4):550-560.
Cuiné et al., 2008, "Evaluation of the impact of surfactant digestion on the bioavailability of danazol after oral administration of lipidic self-emulsifying formulations to dogs." J Pharm Sci. 97(2):995-1012.
Gege et al., 2014, "Identification of the first inverse agonist of retinoid-related orphan receptor (ROR) with dual selectivity for RORβ and RORγt." Bioorg Med Chem Lett. 24(22):5265-5267.
Griffin, 1954, "Calculation of HLB values of non-ionic surfactants." J. of Society of Cosmetic Chemists 5(4):249-256.
Gursoy et al., 2004, "Self-emulsifying drug delivery systems (SEDDS) for improved oral delivery of lipophilic drugs," Biomedicine & Pharmacotherapy 58: 173-182.
Health et al., 2010, "A phase I dose-escalation study of oral BR-DIM (BioResponse 3,3'-Diindolylmethane) in castrate-resistant, non-metastatic prostate cancer." Am J Transl Res. 2(4):402-411.
Jacobs et al., 2000, "New Formulation Strategies for Bioavailability Enhancement of Two Poorly Absorbed Phytonutrient Supplements: Diindolyl Methane and Yohimbe Bark Extract," Proc Int Symp Control Rel Bioact Mater 27:1324-1325.
Javadzadeh et al., 2015, "Recrystallization of Drugs—Effect on Dissolution Rate," Chp. 6 in "Recrystallization in Materials Processing," published online by Intech, downloaded from: http://www.intechopen.com/books/recrystallization-in-materials-processing.
Lindenberg et al., 2004, "Classification of orally administered drugs on the World Health Organization Model list of Essential Medicines according to the biopharmaceutics classification system." Eur J Pharm Biopharm. 58(2):265-278.
Osborne, 1998, "Tamoxifen in the treatment of breast cancer," NEJM 339(22):1609-1618.
Paltsev, et al., 2013, "Comparative preclinical pharmacokinetics study of 3,3'-diindolylmethane formulations: is personalized treatment and targeted chemoprevention in the horizon?" The EPMA Journal 4:25, downloaded from http://www.epmajournal.com/content/4/1/25.
Patel et al. 2012, "Pharmacokinetic evaluation and In Vitro-In Vivo Correlation (IVIVC) of novel methylene-substituted 3,3' diindolylmethane (DIM)." Eur J Pharm Sci. 46(1-2):8-16.
Patel et al., 2015, "Evaluation of spray BIO-Max DIM-P in dogs for oral bioavailability and in Nu/nu mice bearing orthotopic/metastatic lung tumor models for anticancer activity." Pharm Res. 32(7):2292-2300; online publication DOI 10.1007/s11095-015-1620-7.
Patel, et al., 2013, "Pharmacokinetic and pharmacodynamic evaluation of novel dual channel spray dried enteric coated self-emulsifying capsules for anti-cancer agents in dogs." American Association for Cancer Research (AACR), Annual Meeting Apr. 6-10, 2013, Washington DC. Abstract #3361.
Pouton et al., 2006, "Formulation of poorly water-soluble drugs for oral administration: Physicochemical and physiological issues and the lipid formulation classification system," European Journal of Pharmaceutical Sciences 29: 278-287.
Samykutty et al., 2013, "Vitamin K2, a naturally occurring menaquinone, exerts therapeutic effects on both hormone-dependent and hormone-independent prostate cancer cells," Evidence-based Complementary and Alternative Medicine, vol. 2013, Article ID 287358, pp. 1-15.
Sha et al., 2012, "Self-microemulsifying drug-delivery system for improved oral bioavailability of probucol: preparation and evaluation." Int J Nanomedicine 7:705-712.
Sun et al., 2013, "Curcumin inhibits imiquimod-induced psoriasis-like inflammation by inhibiting IL-1beta and IL-6 production in mice." PLoS One 8(6):e67078.
Trevaskis et al., 2008, "Lipid-based delivery systems and intestinal lymphatic drug transport: a mechanistic update." Adv Drug Deliv Rev. 60(6):702-716.
Van Hoogevest and Wendel A., 2014, "The use of natural and synthetic phospholipids as pharmaceutical excipients." Eur J Lipid Sci Technol. 116(9):1088-1107.
Winston-McPherson et al., 2014, "Synthesis and biological evaluation of 2,3'-diindolylmethanes as agonists of aryl hydrocarbon receptor." Bioorg Med Chem Lett. 24(16):4023-4025; online publication doi: 10.106/j.bmcl.2014.06.009.
Zhang et al., 2014, "Discovery of 2-oxo-1,2-dihydrobenzo[cd]indole-6-sulfonamide derivatives as new RORγ inhibitors using virtual screening, synthesis and biological evaluation." Eur J Med Chem. 78:431-441.
Author Unknown, 2008, "Safety Assessment of Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, Poloxamer 105 Benzoate, and Poloxamer 182 Dibenzoate as Used in Cosmetics," Int. J. Toxicology 27:93-128.
International Search Report and Written Opinion, dated Jul. 26, 2016, issued for PCT Application No. PCT/US2016/026715 (published as WO 2016/164770).
Office Action dated May 17, 2017 for U.S. Appl. No. 15/094,732, with Notice of References Cited.
Office Action dated Aug. 17, 2017 for U.S. Appl. No. 15/094,732, with Notice of References Cited.

* cited by examiner

Formulation D
(X 10 magnification)

Formulation L
(X 20 magnification)

Formulation N
(X 20 magnification)

SELF-EMULSIFYING FORMULATIONS OF DIM-RELATED INDOLES

This application is a continuation of U.S. patent application Ser. No. 15/094,732, filed on Apr. 8, 2016, now U.S. Pat. No. 9,918,965, which claims the benefit of U.S. Provisional Application No. 62/146,216, filed on Apr. 10, 2015, each of the foregoing applications is incorporated by reference herein in its entirety.

1. FIELD OF INVENTION

The present invention relates to self-emulsifying compositions of Diindolylmethane (DIM) and certain DIM-related indoles, methods of making various pharmaceutical and nutraceutical formulations using such compositions, and methods of using such compositions and formulations. In particular, the present invention relates to self-emulsifying compositions of DIM (and certain DIM-related indoles) showing improved bioavailability.

2. BACKGROUND

Successful self-emulsifying formulations (e.g., lipid-based formulations (LBFs)) require that a set of materials be combined to form an interactive excipient mixture tailored to the specific physicochemical properties of an Active Pharmaceutical Ingredient (API). Such formulations that spontaneously emulsify on contact with aqueous media are referred to as self-emulsifying drug delivery systems (SEDDS). SEDDS which achieve emulsions with submicron diameter globule size upon spontaneous emulsification are referred to as self-micro-emulsifying drug delivery systems (SMEDDS). SMEDDS may be liquid or semisolid at room temperature and are typically directed at oral or topical drug delivery. To facilitate oral delivery, SEDDS and SMEDDS are filled into hard or soft gelatin capsules.

Prototype SEDDS or SMEDDS formulations are assessed by in vitro dispersion testing in biorelevant media followed by particle size determination and other characterization of the spontaneously formed emulsion. Particle size determinations by light defraction methodology characterizes the globule size of the discrete, individual complex lipid particles containing the API and this in vitro assessment can be used as one methodology to predict availability for absorption and bioavailability of the API in vivo. Performance of the emulsion with regard to API solubilization behavior is assessed by in vitro digestion testing which allows measurement of solubilized drug concentrations released from the emulsion and includes assessment of crystal formation following digestive alteration of the LBF with the controlled addition of digestive enzymes. API solubilization in each individual SEDDS component and in the combination of components is API-specific. In addition, unpredictable interactions between the range of potential solvent oils, surfactants, and co-surfactants, further complicate the SMEDDS formulation development process.

Diindolylmethane is a compound of great potential therapeutic benefit. However, poor oral bioavailability of Diindolylmethane (DIM) has been a major limitation in the successful utilization of DIM for many therapeutic indications. Pure DIM forms tightly packed geometric crystals which are lipophilic but with only modest solubility in oil. DIM possesses extremely low aqueous solubility and rapidly precipitates from solution in organic solvents and re-crystalizes when exposed to aqueous media. As a result, presence of DIM in the primarily aqueous environment within the stomach and intestines results in the persistence of highly insoluble and poorly bioavailable, crystalline DIM. Due to crystallinity, DIM is poorly absorbed throughout the aqueous environments present in the gastrointestinal (GI) tract. The problem of poor bioavailability is at times further compounded by a rapid presystemic metabolism within enterocytes and active first pass hepatic metabolism which further reduces the efficiency of such molecules being used as API's. Limitations on the usefulness of DIM as both a neutraceutical dietary supplement and as an API therefore arise from the physicochemical characteristics of DIM. For successful use as an API and in neutraceutical formulations, DIM requires special treatment and formulation to specifically address its low solubility, crystal forming behavior, and loss due to presystemic metabolism.

The present inventors had previously developed a DIM formulation method that included suspending DIM in solvent and homogenizing it in the presence of encapsulating water soluble polymers, which yields a dry, flowable powder (see U.S. Pat. No. 6,086,915 and EP Patent No. 1067913 B1). This formulation method resulted in increased gastrointestinal absorption and sustained release of DIM compared to crystalline DIM. However, the pharmacokinetics of absorption showed limitation based on the need for DIM to dissolve starting from a solid, crystalline state. Pharmacokinetic evaluation showed a clear but limited advantage derived from this formulation technology compared to crystalline DIM simply suspended in corn or sesame oil (see Anderton et al., 2004, Drug Metab Dispos. 32(6):632-8).

Some studies have reported the use of chemically modified DIM derivatives, which were developed to enhance the anti-cancer activity of DIM at the cellular level in order to increase the potency in dose response relationships (see U.S. Pat. No. 7,709,520). Such chemical modifications of the DIM molecule alter the physicochemical characteristics of the API, and thus, alter formulation requirements. Such modified DIM APIs remain in the class of poorly soluble APIs. However, because the physicochemical characteristics of chemically modified DIM derivatives differ from those of DIM, particularly with regard to lipid solubility, APIs consisting of chemically modified DIM differ from DIM in their formulation requirements. One chemically modified DIM derivative is P-DIM which has been well characterized as to its physicochemical characteristics which are different from those of DIM. P-DIM has a log P of 7 which demonstrates clearly higher lipid solubility compared to DIM (see Patel et al, 2012, Eur J Pharm Sci. 12; 46(1-2):8-16). P-DIM is a C-substituted di-indole methane with additional phenyl rings, which unlike DIM shows instability in the presence of acid. As such, DIM is distinctly different from P-DIM. Since P-DIM lacks stability in acid, this makes P-DIM a poor candidate for formulation strategies which expose the API to the gastric environment where SMEDDS spontaneously emulsify since there is loss of 20% activity of the API due to the acid induced decomposition (see Patel et al., 2015, Pharm Res. Published Online, DOI 10.1007/s11095-015-1620-7). In view of this, Patel et al. reported utilizing spray drying methodology for P-DIM which, like U.S. Pat. No. 6,086,915, includes the use of TPGS, but in addition includes a polymer-based enteric coating to prevent dispersion and breakdown of the API in the stomach. This formulation also included Enova oil, Cremophor EUL as solvent, and Eudragit LD30 D55 as the polymer for enteric coating (see Patel et al., 2015, Pharm Res. Published Online, DOI 10.1007/s11095-015-1620-7).

Another approach to formulation was developed for 2,10-dicarbethoxy-6-methoxy-5,7-dihydro-indolo-(2,3-b)carbazole, which utilized pharmaceutically acceptable excipients consisting of hydroxyl-fatty acid PEG monoester and/or diesters (see U.S. Patent Publication No. 20120184590).

Other approaches to absorption-enhancing formulations of DIM for oral delivery include liquid formulations based on the use of cod liver oil and include a predominant percentage of Polysorbate 80 emulsifier to create a liquid formulation stable in hard gelatin capsules (see U.S. Pat. No. 8,697,123). However, this approach does not relate to self-emulsifying SEDDS or SMEDDS technology and depends on high formulation percentage use of Polysorbate 80. Such high formulation concentration and exposure level to Polysorbate 80 may present tolerability issues during chronic use (see Chassaing et al., 2015, Nature 519(7541):92-6). A separate approach by this group resulted in solid and powdered formulations based on formulation steps which included co-solubilization of DIM in alcohol with a subset of oxyethylene and oxypropylene block co-polymers, followed by evaporation of the alcohol, lyophilization of the mixture, or spray drying of the mixture to remove the water and alcohol (see U.S. Pat. No. 8,791,150 B2). This approach also does not rely on self-emulsifying SEDDS or SMEDDS technology, and instead relies on complex productions steps and high formula weights of oxyethylene and oxypropylene block co-polymers.

Specialized approaches to formulating DIM for topical application have included formulations unrelated to self-emulsifying SEDDS/SMEDDS technology (see U.S. Patent Publication No. 20140193480; U.S. Patent Publication No. 20090274746).

Despite previous efforts to formulate DIM and DIM derivatives for enhanced oral and topical absorption, the need still exists for practical formulation methodology which will better accommodate the specific limitations DIM presents as an API and nutraceutical active ingredient. There is a need for new formulations of DIM capable of self-emulsification and limited or no crystallization in the gastrointestinal environment to realize DIM's therapeutic and nutraceutical potential.

3. BRIEF SUMMARY OF INVENTION

The present invention is the result of the discovery of combinations of excipients that dissolve crystalline Diindolylmethane (DIM). The compositions of the invention encompass those that accommodate a high percentage of DIM. Upon contact with intestinal fluid that occurs after ingestion, such compositions spontaneously emulsify to form an oil-in-water dispersion with fine globule or particle size, increasing the gastrointestinal exposure and systemic absorption of DIM. Development of such combinations of excipients required investigation of the solubility of DIM in each of the tested excipients and in combinations of excipients. The self-emulsifying compositions and formulations of DIM-related indoles provided herein yield increased oral bioavailability of DIM compared to crystalline DIM. The disclosed compositions can be used for pharmaceutical and nutraceutical/nutritional purposes to provide DIM (and certain derivatives of DIM) in a well-tolerated, shelf-stable and highly bioavailable state.

In particular, provided herein are compositions comprising a DIM-related indole and a carrier, wherein the carrier comprises a solvent, one or more surfactants with an HLB of greater than 7, and one or more co-surfactants with an HLB equal to or less than 7. The DIM-related indoles encompassed by the present invention have log P from 3 to 5.5 (which can be an experimentally-determined log P value or a calculated log P value, e.g., log P calculated using software known in the art such as ChemDraw Ultra 12.0 software (CambridgeSoft)). In some embodiments, the DIM-related indole has log P from 3.2 to 5.2. Accordingly, in certain embodiments, provided herein are compositions comprising a DIM-related indole having log P from 3 to 5.5 as the biologically active agent and a carrier of said active agent, wherein the carrier comprises a solvent (e.g., an oil, a lipid or another solvent), one or more surfactants with an HLB of greater than 7, and one or more co-surfactants with an HLB equal to or less than 7. In most preferred embodiments, the DIM-related indole is 3,3'-diindolylmethane (DIM). In some embodiments, the DIM-related indole is 2-(indol-3-ylmethyl)-3,3'-diindolylmethane (LTR).

In certain embodiments, the carrier is a solution or a suspension. In some embodiments, the carrier may be in a liquid form. In some embodiments, the carrier may be in a semi-solid form. In one embodiment, the carrier may be in a form of a gel. In certain embodiments, the composition of the invention is in a form of a solution or a suspension. In some embodiments, the composition of the invention may be in a liquid form. In some embodiments, the composition of the invention may be in a semi-solid form. In one embodiment, the composition of the invention may be in a form of a gel.

In certain embodiments, provided herein are compositions wherein the DIM-related indole has a very high degree of solubility in the carrier. In some embodiments, the DIM-related indole has at least or more than 80%, 85%, 90%, 95%, 97%, 98%, 99% solubility in the carrier (such as up to the limits of its solubility in the carrier). In some embodiments, the DIM-related indole has at least 95% or 100%, or from 95% to 100% solubility in the carrier (such as up to the limits of its solubility in the carrier). In certain embodiments, the DIM-related indole is dissolved in the carrier (i.e., displays at least 98% and up to 100% solubility in the carrier). In most preferred embodiments, the DIM-related indole is 100% dissolved in the carrier (i.e., displays 100% solubility in the carrier). In some embodiments, the DIM-related indole displays at least or more than 10% solubility in the solvent used in the compositions described herein (such as oil, lipid or another solvent, e.g., a diethylene glycol monoethyl ether or a caprylocaproyl polyoxyl-8 glyceride). In some embodiments, the DIM-related indole has at least or more than 12%, 13%, 14%, 15%, 16%, 17%, 18%, 19%, 20% or 25% solubility in the solvent (e.g., at least or more than 15% or 18% solubility in the solvent). In some embodiments, the DIM-related indole displays at least or more than 8%, 9%, 10%, 11%, 12%, 13%, 14%, or 15% solubility in the surfactant with an HLB greater than 7 used in the compositions described herein. In some embodiments, the DIM-related indole displays at least or more than 5%, 6%, 7%, 8%, 9%, 10%, 12% or 15% solubility in the co-surfactant with an HLB equal to or less than 7 used in the compositions described herein. In some embodiments, the DIM-related indole displays at least or more than 3%, 4% or 5% solubility in the triglyceride (or a derivative thereof) used in the compositions described herein. The solubility can be assessed by any method known in the art. For example, the solubility can be assessed by addition of solids until they would not go into the solution without giving cloudiness. In another example, the solubility can be assessed by adding an API and then filtering the solids and determining how much of the API was in solution by dilution in solvent and concentration measurement by HPLC.

In certain embodiments, provided herein are compositions wherein the excipients in the compositions (for example, a solvent, one or more surfactants with an HLB greater than 7, one or more co-surfactants with an HLB equal to or less than 7, a triglyceride or a derivative thereof, an agent that inhibits recrystallization of a DIM-related indole (e.g., a poloxamer), a lecithin, or any other excipient) are pharmaceutically acceptable or acceptable when present in food.

In certain embodiments, provided herein are compositions wherein the solvent is pharmaceutically acceptable or acceptable when present in food. In certain embodiments, the solvent is a caprylocaproyl polyoxyl-8 glyceride, diethylene glycol monoethyl ether, propylene glycol, or an essential oil. In one embodiment, the solvent is a caprylocaproyl polyoxyl-8 glyceride. In one embodiment, the solvent is a diethylene glycol monoethyl ether. In one embodiment, the solvent is propylene glycol. In some embodiments of pharmaceutical compositions and formulations described herein, the solvent is Caprylocaproyl polyoxyl-8 glyceride or diethylene glycol monoethyl ether. In specific embodiments of pharmaceutical compositions and formulations described herein, the solvent is a caprylocaproyl polyoxyl-8 glyceride, a diethylene glycol monoethyl ether or propylene glycol. In some embodiments, the solvent is a lipid or an oil. In particular embodiments, the solvent is an oil such as an essential oil, e.g., peppermint oil, orange oil, lemon oil, limonene, tea tree oil, wintergreen oil, lavender oil, ginger oil, nutmeg oil, fennel oil, eucalyptus oil, rosemary oil, borage oil, pomegranate (Punica granatum Linn., Punicaceae) seed oil, black cumin oil, rice germ oil, rice bran oil, sunflower oil, krill oil, or green-lipped muscle oil. In some embodiments, the solvent is an oil but not olive oil or sunflower oil. In one embodiment, the solvent is an oil, and the oil is peppermint oil. In one embodiment, the solvent is an oil, and the oil is rosemary oil. In particular embodiments of nutritional or nutraceutical compositions and formulations described herein, the solvent is an essential oil. In some embodiments of nutritional or nutraceutical compositions and formulations described herein, the solvent is an oil, such as peppermint oil or rosemary oil. In other particular embodiments of nutritional or nutraceutical compositions and formulations described herein, the solvent is propylene glycol. In other embodiments, provided herein are compositions wherein the solvent is not a lipid or an oil, or not an essential oil. In some embodiments, the solvent is in an amount greater than or equal to 4% or 5% by weight in the compositions described herein. In certain embodiments, the solvent is in an amount from 4% to 50% by weight or from 5% to 50% by weight in the compositions described herein. In some embodiments, the solvent is in an amount from 10% to 40% by weight, or, more specifically, from 20% to 30% by weight in the compositions described herein (e.g., for pharmaceutical compositions described herein). In particular embodiments of nutritional or nutraceutical compositions described herein, the solvent is in an amount from 3% to 15% by weight, or, more specifically, from 5% to 10% by weight in the compositions described herein.

In certain embodiments, provided herein are compositions wherein the one or more surfactants with an HLB of greater than 7 comprise polyoxyethylelene sorbitan monooleate, Lauroyl polyoxyl 32 glyceride or a polyoxyethyl hydroxyl stearate. In one embodiment, provided herein are compositions wherein the surfactant with an HLB of greater than 7 is a lauroyl polyoxyl-32 glyceride. In specific embodiments, provided herein are compositions wherein the surfactant with an HLB of greater than 7 is a polyoxyethyl hydroxyl stearate, or a mixture of monoesters and diesters of 12-hydroxystearic acid and macrogols. In one embodiment, provided herein are compositions wherein the surfactant with an HLB of greater than 7 is a mixture of monoesters and diesters of 12-hydroxystearic acid and macrogols. In one embodiment, provided herein are compositions wherein the surfactant with an HLB of greater than 7 is polyoxyethylene sorbitan monooleate (such as Polysorbate 80). In some embodiments, the compositions provided herein comprise at least two surfactants with HLB greater than 7 (such as any of the surfactants with HLB greater than 7 described herein or known in the art, e.g., a lauroyl polyoxyl-32 glyceride and a mixture of monoesters and diesters of 12-hydroxystearic acid and macrogols, or a lauroyl polyoxyl-32 glyceride and Polysorbate 80). In certain embodiments, the surfactant with an HLB of greater than 7 is in an amount of at least or more than 10% by weight in the compositions described herein. In some embodiments, the surfactant with an HLB of greater than 7 is in an amount from 10% to 50% by weight in the compositions described herein. In particular embodiments, the surfactant with an HLB of greater than 7 is in an amount from 15% to 25% by weight in the compositions described herein.

In certain embodiments, provided herein are compositions wherein the one or more co-surfactants with an HLB equal to or less than 7 comprise Propylene Glycol Caprylate or a phosphatidic acid derivative thereof. In one embodiment, provided herein are compositions wherein the co-surfactant with an HLB equal to or less than 7 is propylene glycol caprylate (such as propylene glycol monocaprylate). In certain embodiments, provided herein are compositions wherein the one or more co-surfactants with an HLB equal to or less than 7 comprise a lecithin. In some embodiments, the lecithin is phosphatidyl choline or lysophosphatidyl choline. In a preferred embodiment, the lecithin is phosphatidyl choline or an excipient enriched in phosphatidyl choline. In some embodiments, the compositions provided herein comprise at least two co-surfactants with an HLB equal to or less than 7 (such as any of the co-surfactants with an HLB equal to or less than 7 described herein or known in the art, e.g., a lecithin and propylene glycol caprylate). In some of these embodiments, at least one of the two or more co-surfactants with an HLB equal to or less than 7 is a lecithin. In one embodiment, at least one of the two or more co-surfactants with an HLB equal to or less than 7 is phosphatidyl choline. In certain embodiments, the co-surfactant with an HLB equal to or less than 7 is in an amount of at least or more than 3% by weight in the compositions described herein. In certain embodiments, the co-surfactant with an HLB equal to or less than 7 is in an amount of at least or more than 5% by weight in the compositions described herein. In some embodiments, the co-surfactant with an HLB equal to or less than 7 is in an amount from 3% to 12% by weight in the compositions described herein. In particular embodiments, the co-surfactant with an HLB equal to or less than 7 is in an amount from 5% to 10% by weight in the compositions described herein. In certain embodiments, the lecithin is in an amount of at least or more than 4% by weight in the compositions described herein. In one embodiment, the lecithin is in an amount of at least or more than 6% by weight in the compositions described herein. In some embodiments, the lecithin is in an amount from 4% to 10% by weight in the compositions described herein. In particular embodiments, the lecithin is in an amount from 6% to 9% by weight in the compositions described herein.

Compositions and formulations described herein can, upon contact with water or intestinal fluids, emulsify to form a dispersion of oil-in-water globules. As described in this application, and without being bound by any theory, lecithin (such as phosphatidyl choline) can be optionally used in the compositions of the invention to reduce the size of oil-in-water emulsion globules formed when the compositions and formulations described herein are dispersed in water or ingested by a subject. In some embodiments, the compositions provided herein comprise an amount of lecithin (such as phosphatidyl choline) capable of reducing the size of oil-in-water emulsion globules formed when the compositions and formulations described herein are dispersed in water or ingested by a subject (e.g., as compared to the same composition without lecithin). In one embodiment, the compositions provided herein comprise an amount of lecithin (such as phosphatidyl choline) capable of reducing the size of oil-in-water emulsion globules formed when the compositions and formulations described herein are dispersed in water or ingested by a subject such that at least 50% of the globules is less than 1.5 µm, 1 µm, 0.75 µm, 0.5 µm or 0.3 µm in size (in diameter). In specific embodiments, the compositions provided herein comprise an amount of lecithin (such as phosphatidyl choline) capable of reducing the size of oil-in-water emulsion globules formed when the compositions and formulations described herein are dispersed in water or ingested by a subject such that at least 50% or at least 90% of the globules is less than 1 µm or less than 400 nm in size (in diameter). In other specific embodiments, the compositions provided herein comprise an amount of lecithin (such as phosphatidyl choline) capable of reducing the size of oil-in-water emulsion globules formed when the compositions and formulations described herein are dispersed in water or ingested by a subject such that at least 50% or at least 90% of the globules is less than 0.5 µm in size (in diameter). In some specific embodiments, the compositions provided herein comprise an amount of lecithin (such as phosphatidyl choline) capable of reducing the size of oil-in-water emulsion globules formed when the compositions and formulations described herein are dispersed in water or ingested by a subject such that at least 50% or at least 90% of the globules is from 0.05 to 1 µm, preferably, from 0.07 to 0.5 µm or, in some most preferred embodiments, from 0.05 to 0.2 µm in size or from 0.01 to 0.2 µm in size (in diameter). In some embodiments, the compositions provided herein comprise an amount of lecithin (such as phosphatidyl choline) capable of reducing the size of oil-in-water emulsion globules formed when the compositions and formulations described herein are dispersed in water or ingested by a subject such that the globules have a (surface weighted) mean particle size from 0.01 to 1 µm, from 0.02 to 1 µm, from 0.03 to 1 µm, from 0.05 to 1 µm, from 0.01 to 0.5 µm, from 0.02 to 0.5 µm, from 0.03 to 0.5 µm, from 0.02 to 0.1 µm, from 0.02 to 0.2 µm, from 0.02 to 0.3 µm, from 0.02 to 0.4 µm, from 0.02 to 0.8 µm, from 0.07 to 0.5 µm, or from 0.09 to 0.3 µm (in diameter). In some embodiments, the compositions provided herein comprise an amount of lecithin (such as phosphatidyl choline) capable of reducing the size of oil-in-water emulsion globules formed when the compositions and formulations described herein are dispersed in water or ingested by a subject such that the globules have a (surface weighted) mean particle size less than 1 µm, less than 0.5 µm, less than 0.4 µm, less than 0.3 µm, less than 0.2 µm, or less than 0.1 µm (in diameter).

In certain embodiments, provided herein are compositions wherein the carrier comprises one or more triglycerides or polyoxyethylene derivatives of a triglyceride. For example, the triglyceride or polyoxyethylene derivative of a triglyceride in the compositions provided herein can be a Caprylic/Capric triglyceride or an oleoyl polyoxyl-6 glyceride. In certain embodiments, provided herein are compositions wherein the one or more triglycerides or polyoxyethylene derivatives of a triglyceride comprise a medium chain triglyceride, a long chain triglyceride, or olive oil. In certain embodiments, provided herein are compositions wherein the one or more triglycerides or polyoxyethylene derivatives of a triglyceride comprise a medium chain triglyceride or a long chain triglyceride. In one embodiment, provided herein are compositions wherein the triglyceride or a polyoxyethylene derivative of a triglyceride is a medium chain triglyceride. In a preferred embodiment, provided herein are compositions wherein the triglyceride or a polyoxyethylene derivative of a triglyceride is a long chain fatty acid such as an oleoyl polyoxyl-6 glyceride. In one embodiment, provided herein are compositions wherein the triglyceride or a polyoxyethylene derivative of a triglyceride is an oleoyl polyoxyl-6 glyceride. In some embodiments, the compositions provided herein comprise at least two triglycerides or polyoxyethylene derivatives of a triglyceride (such as any of the triglycerides or polyoxyethylene derivatives of a triglyceride described herein or known in the art, e.g., a medium chain triglyceride and an oleoyl polyoxyl-6 glyceride). In some embodiments, the triglycerides or polyoxyethylene derivatives of a triglyceride used in the compositions described herein are also co-surfactants with HLB equal to or less than 7. In some embodiments, the compositions provided herein comprise at least one triglyceride or polyoxyethylene derivative of a triglyceride (which also may be a co-surfactant with HLB equal to or less than 7) and at least one co-surfactant with HLB equal to or less than 7 which is not a triglyceride or polyoxyethylene derivative of a triglyceride. In particular embodiments, the triglycerides or polyoxyethylene derivatives of a triglyceride used in the compositions described herein are oil-like triglycerides. In some embodiments, the triglycerides or polyoxyethylene derivatives of a triglyceride used in the compositions described herein are utilized to reduce the crystal size or re-crystallization (e.g., slow down re-crystallization) of a DIM-related indole (upon dispersion in water, intestinal fluids or upon ingestion by a subject). In some embodiments, the triglycerides or polyoxyethylene derivatives of a triglyceride used in the compositions described herein are used to improve absorption of a DIM-related indole. In some embodiments, the triglycerides or polyoxyethylene derivatives of a triglyceride are used in an amount effective to reduce the crystal size, reduce the rate of crystallization and/or improve absorption of a DIM-related indole. For example, the triglycerides or polyoxyethylene derivatives of a triglyceride can be used to reduce the crystal size, reduce the rate of re-crystallization or improve absorption of a DIM-related indole by at least or more than 10%, 20%, 30%, 40%, 50%, 60%, 70%, 80%, 90% or 100% (as compared to the same composition without the triglyceride). In one embodiment, the triglycerides or polyoxyethylene derivatives of a triglyceride can be used in an amount effective to reduce recrystallization or improve absorption of a DIM-related indole by at least or more than 25% (wherein the recrystallization and absorption are assessed by any criteria or method described herein or known in the art). In certain embodiments, the triglycerides or polyoxyethylene derivatives of a triglyceride is in an amount of at least or more than 0.5% by weight in the compositions described herein. In some embodiments, the triglycerides or polyoxyethylene derivatives of a triglyceride is in an amount from 1% to 20% by weight in the compositions described herein. In particular embodiments, the triglycerides or polyoxyethylene derivatives of a triglyceride are in an amount from 6% to 12% by weight in the compositions described herein.

In certain embodiments, provided herein are compositions wherein a DIM-related indole (e.g., DIM) is present in the compositions in a concentration from 10 mg/ml to 300 mg/ml, or more specifically, in a concentration from 10 mg/mL to 200 mg/mL, 30 mg/ml to 150 mg/ml, 70 mg/ml to 130 mg/ml, or 90 mg/ml to 125 mg/ml. For example, a DIM-related indole (e.g., DIM) can be present in the compositions and formulations described herein in the concentration between 30 mg/ml and 150 mg/ml. In another example, a DIM-related indole (e.g., DIM) can be present in the compositions and formulations described herein in the concentration between 70 mg/ml and 130 mg/ml. In some embodiments, the compositions provided herein comprise the DIM-related indole (e.g., DIM) in an amount of at least or more than 5% or 7.5% by weight. In specific embodiments, the compositions provided herein comprise the DIM-related indole (e.g., DIM) in an amount of at least or more than 10% or 12% by weight. In one embodiment, the compositions provided herein comprise the DIM-related indole (e.g., DIM) in an amount of at least or more than 10% by weight. In particular embodiments, the compositions provided herein comprise the DIM-related indole (e.g., DIM) in an amount from 2% to 20%, 5% to 20%, 7.5% to 15%, 8% to 20%, 8% to 14%, 9% to 13%, or 10% to 12%, or 12 to 14% by weight. In a specific embodiment, the compositions provided herein comprise the DIM-related indole (e.g., DIM) in an amount from 10% to 20% by weight. In certain embodiments, the compositions and formulations provided herein comprise from 20 to 150 mg of the DIM-related indole (e.g., DIM) per dose (e.g., capsule). In preferred embodiments, the compositions and formulations provided herein comprises from 25 to 100 mg of the DIM-related indole (e.g., DIM) per dose (e.g., capsule). In specific embodiments, the compositions and formulations provided herein comprise 25 mg, 30 mg, 40 mg, 50 mg, 60 mg, 70 mg, 75 mg, 80 mg, 90 mg or 100 mg of the DIM-related indole per dose (e.g., per capsule).

In certain embodiments, provided herein are compositions wherein the carrier further comprises a derivatized cellulose that is soluble in the composition, a polyoxythene/polyoxypropylene copolymer (known as poloxamer), polyvinyl acetate phthalate, or polyvinyl pyrolidone. In preferred embodiments, the carrier comprises a polyethylene oxide polypropylene oxide block copolymer. In specific embodiments, the carrier comprises block copolymers of polyoxypropylene and polyoxyethylene, wherein a central block of the polyoxypropylene is flanked by blocks of the polyethylene oxide on both ends (which can be described as having the following chemical formula: $HO(C_2H_4O)_a(C_3H_6O)_b(C_2H_4O)_aH$). In some embodiments, the compositions described herein (e.g., the carrier in the compositions) comprise a poloxamer wherein the molecular mass of the hydrophobic block of the poloxamer (i.e., the $C_3H_6O$ or polyoxypropylene blocks) is more than 50% (e.g., more than 52%) of the total molecular mass of the poloxamer. In some embodiments, the compositions described herein (e.g., the carrier in the compositions) comprise a poloxamer wherein the molecular mass of the hydrophilic block of the poloxamer (i.e., the $C_2H_4O$ or polyethylene oxide blocks) is less than 2250 Daltons (e.g., less than 2000 Daltons, less than 1500 Daltons, or less than 1200 Daltons). In particular embodiments, the carrier comprises a poloxamer, for example, a poloxamer wherein the molecular mass of the hydrophobic block of the poloxamer is greater than 50% (e.g., greater than 52%) of the total molecular mass of the poloxamer and the molecular mass of the hydrophilic block of the poloxamer is less than 2250 Daltons (e.g., less than 2000 Daltons, less than 1500 Daltons, or less than 1200 Daltons). In one embodiment, the poloxamer is Poloxamer 124. In certain embodiments, the poloxamer is in an amount of at least or more than 5% by weight in the compositions described herein. In some embodiments, the poloxamer is in an amount from 5% to 30% by weight in the compositions described herein. In particular embodiments, the poloxamer is in an amount from 15% to 25% by weight in the compositions described herein.

In particular embodiments, the compositions described herein (e.g., the carrier in the compositions) comprise a polyoxythene/polyoxypropylene copolymer wherein the molecular mass of the hydrophobic block of the copolymer (i.e., the $C_3H_6O$ or polyoxypropylene blocks) is greater than 50% (e.g., greater than 52%) of the total molecular mass of the copolymer, and/or the molecular mass of the hydrophilic block of the copolymer (i.e., the $C_2H_4O$ or polyethylene oxide blocks) is less than 2250 Daltons (e.g., less than 2000 Daltons, less than 1500 Daltons, or less than 1200 Daltons). In certain embodiments, the polyoxythene/polyoxypropylene copolymer is in an amount of at least or more than 5% by weight in the compositions described herein. In some embodiments, the polyoxythene/polyoxypropylene copolymer is in an amount from 5% to 30% by weight in the compositions described herein. In particular embodiments, the polyoxythene/polyoxypropylene copolymer is in an amount from 15% to 25% by weight in the compositions described herein.

In some embodiments, the compositions described herein (e.g., the carrier in the compositions) do not comprise a polyoxythene/polyoxypropylene copolymer (such as poloxamer) wherein the molecular mass of the hydrophobic block of the copolymer (i.e., the $C_3H_6O$ or polyoxypropylene blocks) is equal to or less than 50% of the total molecular mass of the copolymer. In some embodiments, the compositions described herein (e.g., the carrier in the compositions) do not comprise a polyoxythene/polyoxypropylene copolymer (such as poloxamer) wherein the molecular mass of the hydrophilic block of the copolymer (i.e., the $C_2H_4O$ or polyethylene oxide blocks) is equal to or more than 2250 Daltons. In some specific embodiments, the compositions described herein (e.g., the carrier in the compositions) do not comprise a poloxamer wherein the molecular mass of the hydrophobic block of the poloxamer is equal to or less than 50% of the total molecular mass of the poloxamer, and wherein the molecular mass of the hydrophilic block of the poloxamer is equal to or more than 2250 Daltons.

In some embodiments, the compositions and formulations described herein (e.g., the carrier in the compositions described herein) do not comprise polyethylene oxides.

In some preferred embodiments, the compositions and formulations described herein (e.g., the carrier in the compositions described herein) do not comprise monomer polyvinyl caprolactam (such as Soluplus®), or the polymer used in such compositions or formulations is not monomer polyvinyl caprolactam (such as Soluplus®). In some preferred embodiments, the compositions and formulations described herein (e.g., the carrier in the compositions described herein) do not comprise polyvinyl caprolactam-polyvinyl acetate-polyethylene glycol graft copolymer (such as Soluplus®), or the polymer used in such compositions or formulations is not polyvinyl caprolactam-polyvinyl acetate-polyethylene glycol graft copolymer (such as Soluplus®). In some preferred embodiments, the compositions and formulations described herein (e.g., the carrier in the compositions described herein) do not comprise a polyethylene glycol, polyvinyl acetate and polyvinylcaprolactame-based graft copolymer (such as Soluplus®), or the polymer used in such compositions or formulations is not a polyethylene glycol, polyvinyl acetate and polyvinylcaprolactame-based graft copolymer (such as Soluplus®).

In some embodiments, the carrier comprises derivatized cellulose. For example, the derivatized cellulose can be hydroxypropylmethyl cellulose, hydroxypropyl methyl cellulose acetate phthalate, or hydroxypropyl methyl cellulose acetate succinate.

In certain embodiments, provided herein are compositions wherein the carrier further comprises an agent that inhibits crystallization of the DIM-related indole on dispersion of the composition in water or intestinal fluids (or ingestion by a subject). In specific embodiments, the ability of an agent to inhibit crystallization of the DIM-related indole is assessed by in vitro digestion testing (e.g., using in vitro digestion tests described herein). Such agent can be, without limitation, a derivatized cellulose that is soluble in the composition, a polyoxythene/polyoxypropylene copolymer (known as poloxamer), polyvinyl acetate phthalate, or polyvinyl pyrolidone. In one preferred embodiment, such agent is a poloxamer, for example, a poloxamer wherein the molecular mass of the hydrophobic block of the poloxamer is greater than 50% of the total molecular mass of the poloxamer and, optionally, the molecular mass of the hydrophilic block of the poloxamer is less than 2250 Daltons (e.g., Poloxamer 124). In one preferred embodiment, such agent is a poloxamer, for example, a poloxamer wherein the molecular mass of the hydrophobic block of the poloxamer is greater than 50% of the total molecular mass of the poloxamer and the molecular mass of the hydrophilic block of the poloxamer is less than 2250 Daltons (e.g., Poloxamer 124). In another embodiment, such agent is a derivatized cellulose. For example, the derivatized cellulose can be hydroxypropylmethyl cellulose, hydroxypropyl methyl cellulose acetate phthalate, or hydroxypropyl methyl cellulose acetate succinate. In another embodiment, such agent is a triglyceride or a derivative thereof. In certain embodiments, the carrier comprises a polyethylene oxide polypropylene oxide block copolymer (such as $HO(C_2H_4O)_a(C_3H_6O)_b(C_2H_4O)_aH$).

In specific embodiments, provided herein are compositions and formulations that do not comprise TPGS. In additional specific embodiments, provided herein are compositions and formulations that do not comprise cod liver oil.

In certain embodiments, provided herein are compositions and formulations which, upon dispersion in water or intestinal fluids (which occurs upon ingestion by a subject), emulsify to form a dispersion of oil-in-water emulsion globules (e.g., lipid-based globules). In some embodiments, at least 50% of such globules are less than 1.5 µm, 1 µm, 0.75 µm, 0.5 µm or 0.3 µm in size (in diameter). In particular embodiments, at least 50% of such globules are less than 1 µm in diameter. In preferred embodiments, at least 50% of such globules are less than 0.3 µm in size, most preferably less than 0.1 µm in size (in diameter). In some embodiments, at least 50% of such globules are between 0.05 and 1 µm, between 0.07 and 0.5 µm, between 0.05 and 0.2 µm in size, between 0.01 and 0.5 µm in size, or between 0.01 and 0.2 µm in size (in diameter). In some embodiments, the globules have a (surface weighted) mean particle size between 0.05 and 1 µm, between 0.07 and 0.5 µm, between 0.09 and 0.3 µm, between 0.1 and 0.2 µm, or between 0.05 and 0.2 µm. In some embodiments, the globules have a mean particle size between from 0.01 to 1 µm, from 0.02 to 1 µm, from 0.03 to 1 µm, from 0.05 to 1 µm, from 0.01 to 0.5 µm, from 0.02 to 0.5 µm, from 0.03 to 0.5 µm, from 0.02 to 0.1 µm, from 0.02 to 0.2 µm, from 0.02 to 0.3 µm, from 0.02 to 0.4 µm, from 0.02 to 0.8 µm, from 0.07 to 0.5 µm, or from 0.09 to 0.3 µm (in diameter). In preferred embodiments, the globules have a mean particle size of less than 1 micron, more preferably, less than 0.5 µm. In specific embodiments, the globules have a mean particle size of less than 0.4 µm, less than 0.3 µm, or less than 0.1 µm (in diameter). The size of the globules or particles can be determined by any method known in the art or described herein. In one embodiment, the size of the globules or particles is determined by in vitro dispersion testing.

In certain embodiments, provided herein are compositions and formulations which, 2 hours after ingestion by a subject, provide the DIM-related indole in a plasma of the subject in a concentration of at least or more than 150 ng/ml, 200 ng/ml, 250 ng/ml or 300 ng/ml, or between 200 ng/ml and 600 ng/ml, between 250 ng/ml and 500 ng/ml, or between 300 ng/ml and 400 ng/ml. In particular embodiments, the compositions and formulations described herein, upon ingestion by a subject, provide Cmax of the DIM-related indole of at least or more than 150 ng/ml, 200 ng/ml, 250 ng/ml or 300 ng/ml (in a plasma of the subject). In certain embodiments, provided herein are compositions and formulations which, upon ingestion by a subject, achieve mean or average AUC (ng/ml*hr) of the DIM-related indole of at least or more than 500 ng/ml*hr, 750 ng/ml*hr, 1000 ng/ml*hr, 1250 ng/ml*hr or 1500 ng/ml*hr, or between 750 ng/ml*hr and 2000 ng/ml*hr, or between 1000 ng/ml*hr and 2000 ng/ml*hr, or between 1250 and 1750 ng/ml*hr (in a plasma of the subject). In preferred embodiments, the subject is a human.

The compositions provided herein can be formulated in a form suitable for administration to a subject (e.g., a human). For example, the compositions provided herein can be formulated as pharmaceutical compositions. Such compositions can be formulated with excipients (e.g., solvents, surfactants with an HLB greater than 7, or cos-surfactants with HLB equal to or less than 7) that are known to be or determined to be pharmaceutically acceptable. In other embodiments, the compositions provided herein can be formulated as nutritional or nutraceutical compositions. Such compositions can be formulated with excipients that are known to be or determined to be acceptable when used in food. The terms "compositions" and "formulations" are used throughout this application interchangeably. The Examples section of this application refers to the compositions of the invention as "formulations," and describes certain embodiments of the compositions of the invention. The compositions provided herein can also be characterized as self-emulsifying (or, in some embodiments, self-microemulsifying, i.e., producing globules of less than 1 micron in size) excipient formulations for delivery of a DIM-related indole (which can increase the bioavailability of the DIM-related indole), and optionally, an additional API. The term "formulations" is also used to refer to the forms of the compositions of the invention that are suitable for pharmaceutical and/or nutritional/nutraceutical uses (e.g., capsules and drug delivery vehicles that can be administered to a subject). The compositions provided herein can provide a self-emulsifying drug delivery system for pharmaceutical or nutraceutical/nutritional uses.

In certain embodiments, the compositions provided herein are formulated for oral delivery. In some embodiments, the compositions provided herein are formulated in a form of a capsule such as a gelatin capsule (for oral administration). In specific embodiments, the compositions provided herein are formulated in a form of a soft shell gelatin capsule or a hard shell gelatin capsule. In some embodiments, the compositions provided herein are formulated in a form of a food (e.g., in a form of a food bar or treat). In some embodiments, the compositions provided herein are used to manufacture a blister pack for oral administration. In other embodiments, the compositions provided herein are formulated for topical delivery. Such topical delivery are to surfaces and in forms capable of emulsification of the composition. For example, the compositions provided herein can be formulated for administration to a wet surface (e.g., a mucosal surface or a bleeding wound), or formulated for use with water (e.g., a shampoo, a face scrub, or a face wash). In certain embodiments, the compositions provided herein are formulated for topical delivery to a mucosal surface. In specific embodiments, the compositions provided herein are formulated for topical delivery to cervico-vaginal or rectal epithelium and/or mucosa. In one embodiment, the compositions provided herein can be formulated for topical delivery to a wound (such as an open, bleeding wound). In some embodiments, the compositions provided herein are diluted with a solvent for processing onto delivery devices. The dilution of the compositions described herein can be from 2% or 3% to 30% or 40%. In some embodiments, the compositions provided herein are diluted with solvent by at least 5%, 10%, 15%, 20%, 30%, or 35% for processing onto delivery devices. In some embodiments, the compositions provided herein are diluted with solvent from 2% to 40%, from 5% to 40%, from 10% to 40%, from 15% to 40%, from 20% to 40%, from 2% to 30%, from 5% to 30%, from 10% to 30%, from 2% to 25%, from 5% to 25%, from 10% to 25%, from 2% to 20%, from 5% to 20%, from 10% to 20%, from 2% to 15%, or from 5% to 15%, for processing onto delivery devices. Such delivery devices can then be administered to a subject. The delivery devices include, without limitation, a tampon, a food or a food supplement for veterinary or human use (e.g., a nutritional health bar, a drink mix, etc.), a wound dressing, a rectal suppository, and a formulation for personal hygiene use (for mixing with water and applying, e.g., a face scrub, a face wash, or a shampoo). In one embodiment, the delivery device is a tampon (e.g., for vaginal use). In one embodiment, the delivery device is a suppository (e.g., for rectal use). In some embodiments, the delivery device is a solution or a suspension formulated as a cosmetic or a hygiene product (e.g., a shampoo, a face scrub or a face wash). In certain embodiments, the compositions and their formulations provided herein are shelf-life stable (e.g., stable for at least or more than 6 months, 1 year, 2 years, or 5 years). In one embodiment, the compositions and their formulations provided herein are shelf-life stable for at least 1 year. The stability can be characterized, for example, by lack of re-crystallization of the DIM-related indole (e.g., DIM) in the composition.

In some embodiments, the compositions and formulations provided herein comprise one biologically active agent (a DIM-related indole, e.g., DIM). In other embodiments, the compositions and formulations provided herein comprise two or more biologically active agents (a DIM-related indole and one or more additional biologically active agents). In some embodiments, the additional biologically active agent in the compositions and formulations provided herein is a retinoid agent (e.g., retinyl palmitate), Vitamin D, melatonin, Vitamin K, bicalutamide, artemether, tamoxifen, plumbagin, curcumin or ursolic acid. In specific embodiments, the compositions and formulations provided herein further comprise Retinyl Palmitate (in addition to a DIM-related indole). In some embodiments, the compositions and formulations provided herein further comprise Vitamin D (in addition to a DIM-related indole). In other specific embodiments, the compositions and formulations provided herein further comprise Retinyl Palmitate and Vitamin D (in addition to a DIM-related indole). In particular embodiments, Retinyl Palmitate is in an amount from 2.75 to 10 mg per dose in the compositions and formulations provided herein. In other embodiments, the compositions and formulations provided herein further comprise melatonin (in addition to a DIM-related indole). In additional embodiments, the compositions and formulations provided herein further comprise Vitamin K (in addition to a DIM-related indole). In preferred embodiments, Vitamin K is Vitamin K2, e.g., in the amount from 25 µg to 1600 µg per dose (e.g., capsule) in the compositions and formulations provided herein. In other embodiments, Vitamin K is in an amount from 175 mg to 250 mg per dose (e.g., capsule) in the compositions and formulations provided herein. In sadditional embodiments, the compositions and formulations provided herein further comprise biculatamide (Casodex) (in addition to a DIM-related indole). In other additional embodiments, the compositions and formulations provided herein further comprise artemether (in addition to a DIM-related indole). In other embodiments, the compositions and formulations provided herein further comprise tamoxifen (in addition to a DIM-related indole). In particular embodiments, a DIM-related indole, such as DIM, is in an amount from 25 to 100 mg per dose (e.g., capsule) in the compositions and formulations provided herein (when used either as the only biologically active agent or together with one or more additional biologically active agents in the compositions and formulations described herein).

The compositions and formulations described herein can be used, without limitation, for: (i) treating or preventing a skin condition such as acne (wherein the compositions described herein may comprise a retinoid agent (such as Retinyl palmitate or another retinoid agent described herein or known in the art) and/or Vitamin D as a second API); (ii) promoting sleep, reducing sleep latency, improving sleep quality, or reducing the number of night-time awakenings in a subject (wherein the compositions described herein may comprise melatonin as a second API); (iii) promoting bone health and/or heart health (wherein the compositions described herein may comprise Vitamin K as a second API); (iv) treating prostate cancer (wherein the compositions described herein may comprise biculatamide (casodex) as a second API); (v) treating breast cancer (wherein the compositions described herein may comprise tamoxifen as a second API); or (vi) treating parasitic diseases, such as malaria (wherein the compositions described herein may comprise artemether as a second API). In some embodiments, the compositions and formulations described herein are used for treating or preventing atopic dermatitis in a subject (such as a mammalian subject, e.g., a human, a dog, or a cat). The methods of treatment, dosages and treatment regimens contemplated herein are further described in the detailed description.

3.1 Terminology

Active Pharmaceutical Ingredient (API):

Active chemical entity utilized in compositions and formulations of the present invention. API is synonymous with Active Nutraceutical Ingredient in the context of the present invention.

Partition Coefficient (Log P):

This factor describes the lipophilicity of a molecule corresponding to the partition coefficient of a compound between a lipophilic and a hydrophilic phase, usually 1-octanol and water. The partition coefficient is the concentration of the drug in the organic layer divided by that in the aqueous one. Log P is defined as the decadic logarithm of P. Higher log P values indicate non-polar solubility requirements and lipophilicity. The meaning of the term "partition coefficient" or "log P" used herein is the same as that known in the art.

Self-Emulsifying Drug Delivery Systems (SEDDS) and Self-Micro-Emulsifying Drug Delivery Systems (SMEDDS):

SEDDS and SMEDDS are physically stable isotropic mixtures of a solvent (e.g., oil), surfactants, co-surfactants and solubilized drug substance that can be administered, for example, orally in soft or hard gelatin capsules. SEDDS and SMEDDS readily disperse in the GI-tract, where the motility in the stomach and intestine allow for emulsification. Self-emulsifying properties are conferred by proper selection of the solvent/surfactant system combinations. In order to reach the optimum HLB value required for the emulsification, appropriate combinations of different solvents and surfactants must be found for any specific active pharmaceutical or nutraceutical ingredient. SMEDDS formulations, when contacted with an aqueous medium, form a spontaneous emulsion with a mean particle or globule size in diameter of close to or less than 1 micron, and thus, are called self "micro-emulsifying" drug delivery systems or SMEDDS.

Self-Emulsifying DIM Compositions of the Invention are DIM SEDDS and DIM SMEDDS compositions.

DIM SEDDS and DIM SMEDDS of the present invention describe compositions and formulations which, when contacted with an aqueous medium (such as mixed with water or gastrointestinal fluids), produce a fine oil-in-water emulsion. Particularly, the DIM SMEDDS of the present invention, when contacted with an aqueous medium, form an emulsion with a mean particle or globule size in diameter of less than 1 micron, and in preferred embodiments, less than 400 nm, more preferably less than 200 nm, and most preferably less than 100 nm. Whereas DIM SEDDS compositions are self-emulsifying compositions that encompass compositions which form an emulsion having a mean particle or globule size in diameter of less than 1 micron (i.e., DIM SMEDDS) and compositions which form an emulsion having a mean particle or globule size equal to or more than 1 micron.

Hydrophilic-Lipophilic Balance (HLB):

The HLB is an empirical formula that is used to characterize surfactants and to select those appropriate for preparation of microemulsions. The term "HLB" is an abbreviation for Hydrophilic-Lipophilic-Balance and describes solvent capacity of surfactants. Both non-ionic and ionic surfactants are utilized in the present invention in specific combinations constituting the "surfactant system" selected to be less affected by pH, ionic strength changes, and digestive enzymes. The HLB value of each lipid vehicle is calculated according to the following formula: HLB=20(1−S/A), where S is the saponification number of the ester and A is the acid number of the fatty acid. For formulas for calculating HLB values, and for HLB values of certain surfactants and co-surfactants, see also Griffin, W M, 1954, Journal of the Society of Cosmetic Chemists 5 (4): 249-56, which is incorporated by reference herein in its entirety.

Surfactant System:

A combination of complementary surfactants and co-surfactants with different HLB values and, optionally, additional emulsification enhancers for specific combined solubilizing capacity for the APIs of the present invention.

Globule Size Determinants:

The globule or particle size of the dispersed phase of mixtures of solvents and surfactants with the dissolved active ingredient is determined by a number of factors including the method of preparation, the concentration and identity of the solvent/surfactant system and the relative amounts of the individual components. The median globule size as reported is often a normal distribution.

Area Under the Curve (AUC):

In the field of pharmacokinetics, the area under the curve (AUC) is the area under the curve in a plot of concentration of drug in blood plasma over time. Typically, the area is computed starting at the time the drug is administered and ending when the concentration in plasma is negligible. The AUC (from zero to infinity) represents the total drug exposure over time. Bioavailability generally refers to the fraction of drug absorbed systemically. This is often measured by quantifying the AUC. The AUC is useful, for example, when trying to determine whether two formulations providing the same dose of a drug release the same quantity of the drug into the blood stream.

Maximal Concentration (Cmax):

Cmax is a term used in pharmacokinetics to refer to the maximum (or peak) serum concentration that a drug achieves in a specified compartment, like blood plasma, after the drug has been administrated.

As used herein, the term "subject" and "patient" are used interchangeably to refer to an animal (e.g., cow, horse, sheep, pig, chicken, turkey, quail, cat, dog, mouse, rat, rabbit, guinea pig, etc.). In some embodiments, the subject is a mammal such as a non-primate and a primate (e.g., monkey and human). In specific embodiments, the subject is a human.

As used herein, the term "effective amount" in the context of the amount of one API (a DIM-related indole) or an amount of a combination of APIs used in the compositions and formulations described herein refers to the amount of API(s) that results in a beneficial or therapeutic effect. In specific embodiments, an "effective amount" is an amount of the API (i.e., a DIM-related indole alone, or a DIM-related indole in combination with one or more additional APIs) which is sufficient to achieve at least one, two, three, four or more of the following effects: (i) reduction or amelioration of the severity of a disease or condition in the subject or population of subjects or a symptom associated therewith; (ii) reduction of the duration of a disease or condition in the subject or population of subjects or a symptom associated therewith; (iii) prevention of the progression of a disease or condition in the subject or population of subjects or a symptom associated therewith; (iv) regression of a disease or condition in the subject or population of subjects or a symptom associated therewith; (v) prevention of the development or onset of a disease or condition in the subject or population of subjects or a symptom associated therewith; (vi) prevention of the recurrence of a disease or condition in the subject or population of subjects or a symptom associated therewith; (vii) prevention or reduction of the spread of a disease from the subject or population of subjects to another subject or population of subjects; (viii) elimination of a disease or condition in the subject or population of subjects; (ix) enhancement or improvement of the prophylactic or therapeutic effect(s) of another therapy in the subject or population of subjects; (x) reduction of the number and/or severity of symptoms of a disease or condition in the subject or population of subjects; (xi) the clearance of an infection with a pathogen (e.g., a parasite); (xii) the eradication of one or more symptoms associated with an infection; (xiii) the reduction of time required to clear an infection; (xiv) the reduction or amelioration of the severity of an infection and/or one or more symptoms associated therewith; (xi) the reduction or elimination of a pathogen as measured by, e.g., parasite count; (xvi) the prevention of an increase in the pathogen numbers as measured by, e.g., parasite count; (xvii) the prevention of the development or onset of an infection or one or more symptoms associated therewith; (xviii) the inhibition of the progression of a cancer and/or one or more symptoms associated therewith; (xix) a reduction in the growth of a tumor or neoplasm, e.g., a decrease in tumor size (e.g., volume or diameter); (xx) eradication, removal, or control of cancer; and/or (xxi) a decrease in the number or size of metastases; (xxii) an increase in tumor-free survival rate of patients, (xxiii) increase in relapse free survival, or (xxiv) an increase in the number of patients in remission.

4. BRIEF DESCRIPTION OF DRAWINGS

FIG. 1: Bar Chart showing Area Under the Curve (AUC) comparison of unformulated Crystalline DIM, spray dried BR-DIM, and DIM SMEDDS Pharmaceutical Formulation "D". Mean AUC (ng/ml*hr) for various Diindolylmethane (DIM) formulations is shown.

Figure 2:
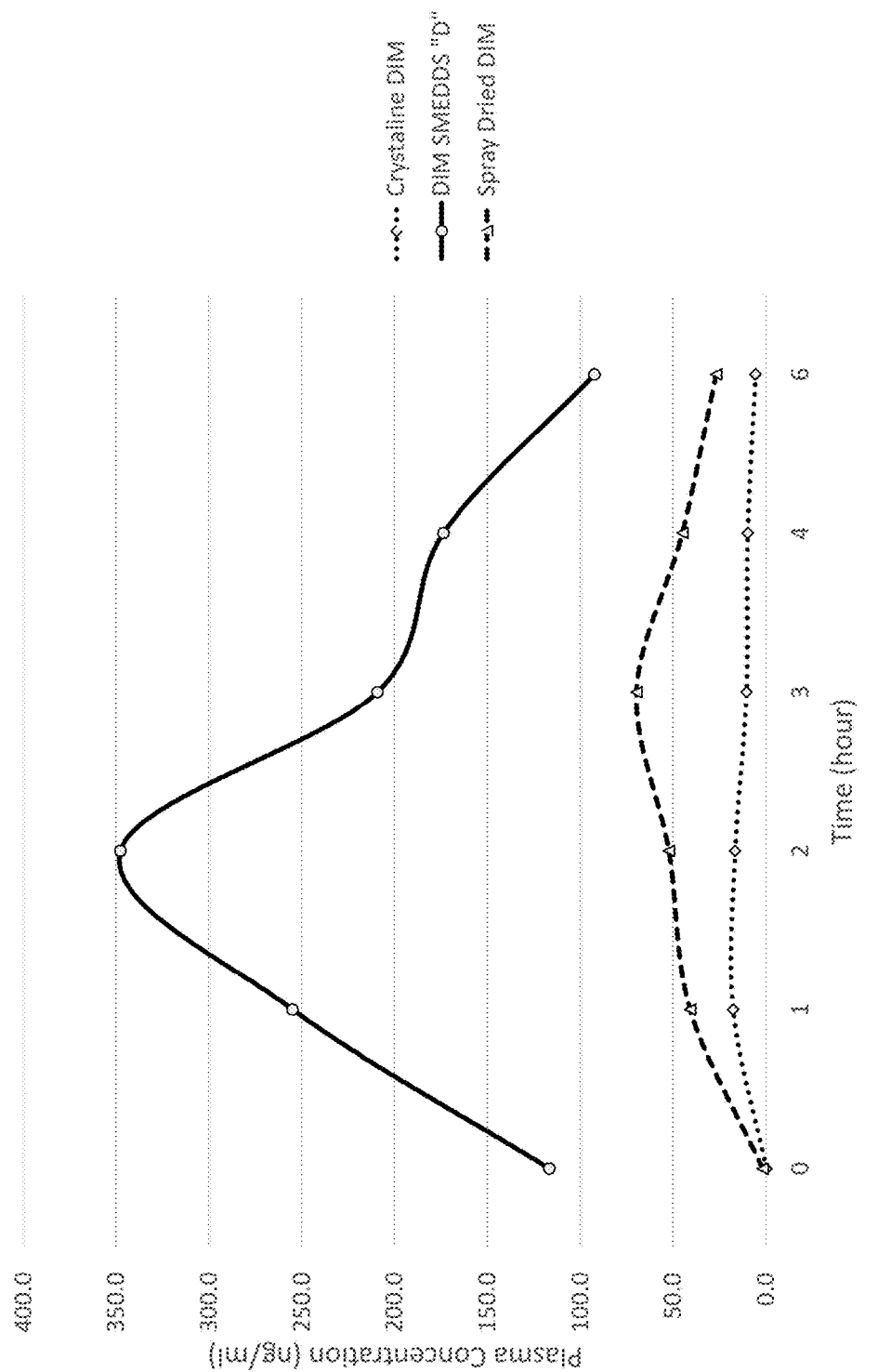

FIG. 2: Diindolylmethane (DIM) Plasma Concentrations vs. Time for various DIM formulations during Human Use. Composite Chart of human studies of DIM plasma levels versus time for 6 hour testing period of Crystalline DIM, spray dried BR-DIM, and DIM SMEDDS Pharmaceutical Formulation "D".

Figure 3:
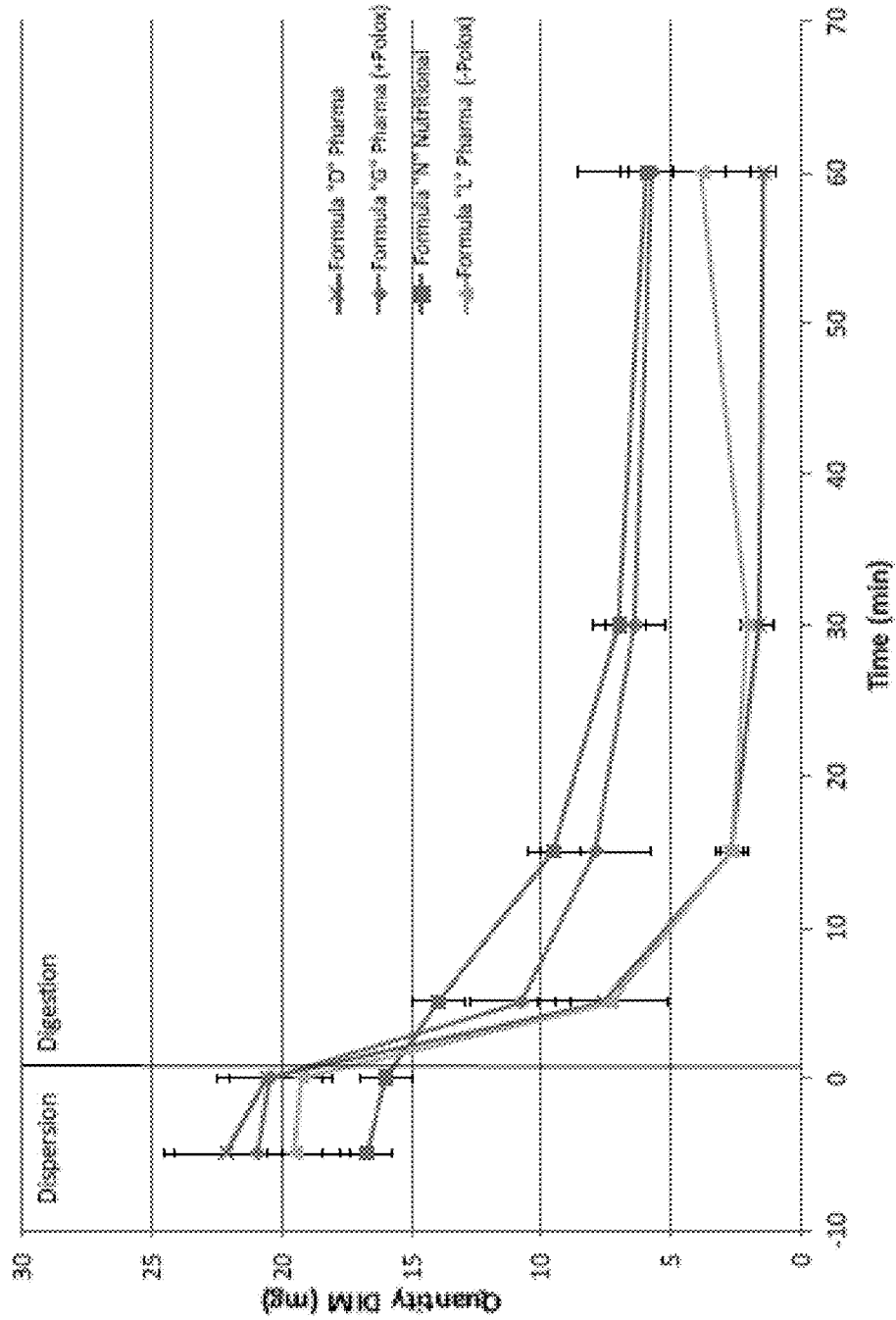

FIG. 3: Comparison of the quantity of dissolved DIM in the aqueous phase determined by HPLC during 4 separately conducted In Vitro Digestion Assays including dispersion and digestion test periods.

Figure 4A:
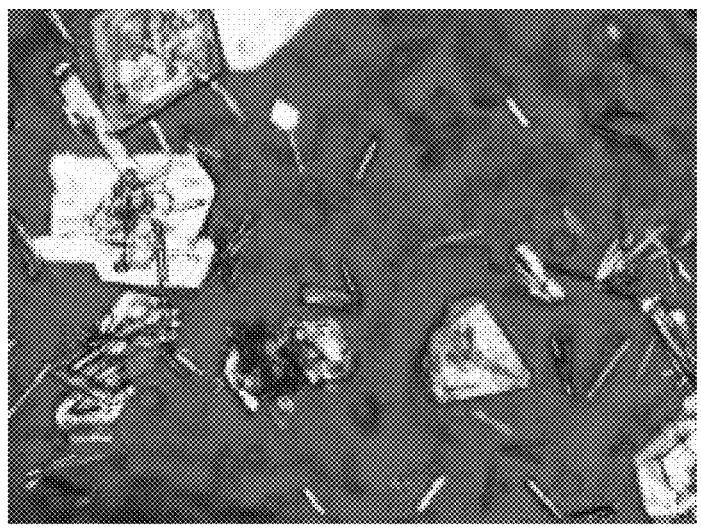
Figure 4B:
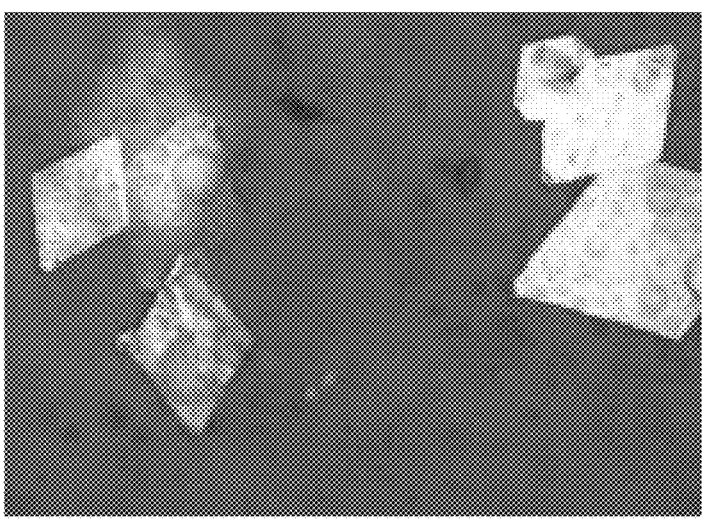
Figure 4C:
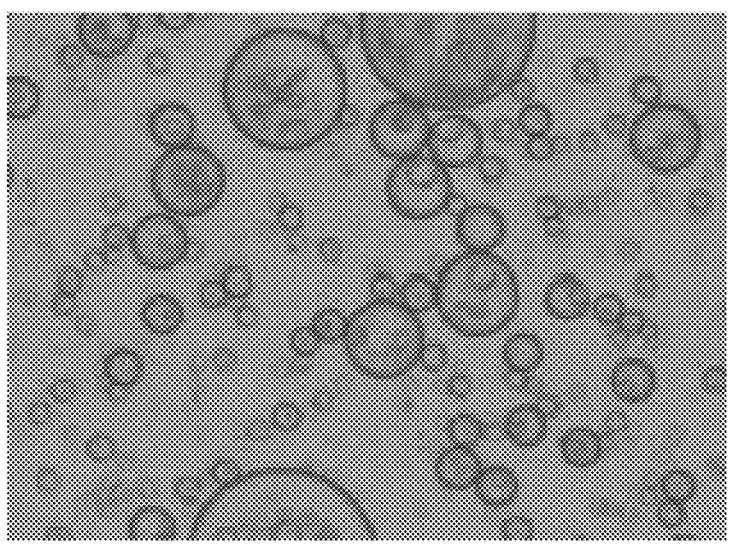

FIGS. 4A, 4B and 4C: Polarized-light micrographs of DIM SMEDDS formulation dispersed in water. (FIG. 4A) Pharmaceutical Formulation "D" at magnification ×10. (FIG. 4B) Pharmaceutical Formulation "L" at magnification ×20. (FIG. 4C) Nutritional Formulation "N" at magnification ×20.

Figure 5A:
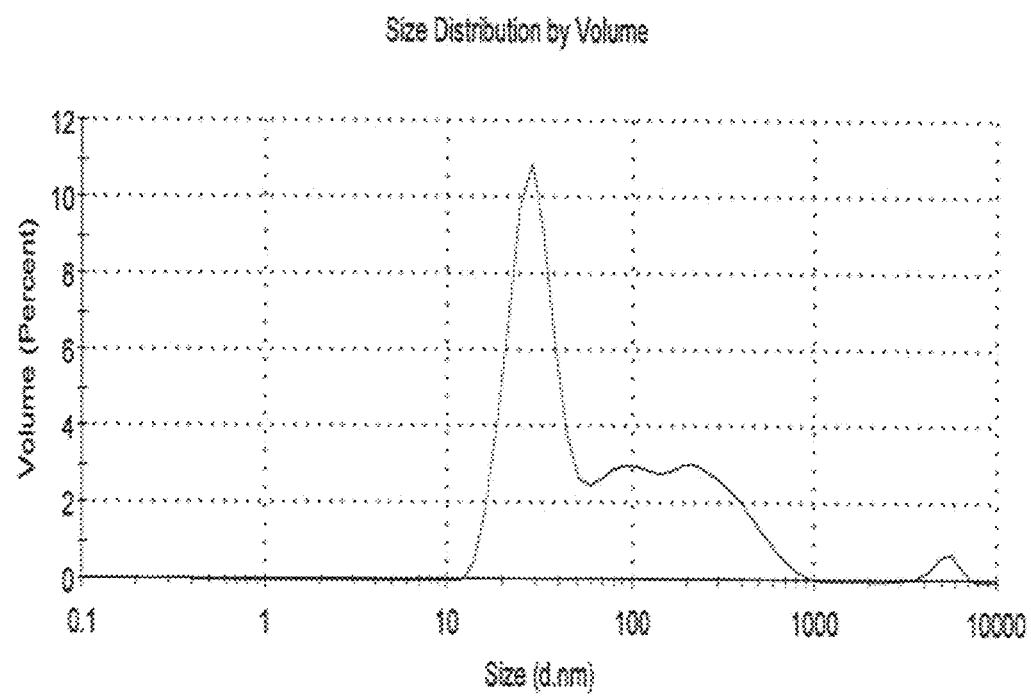
Figure 5B:
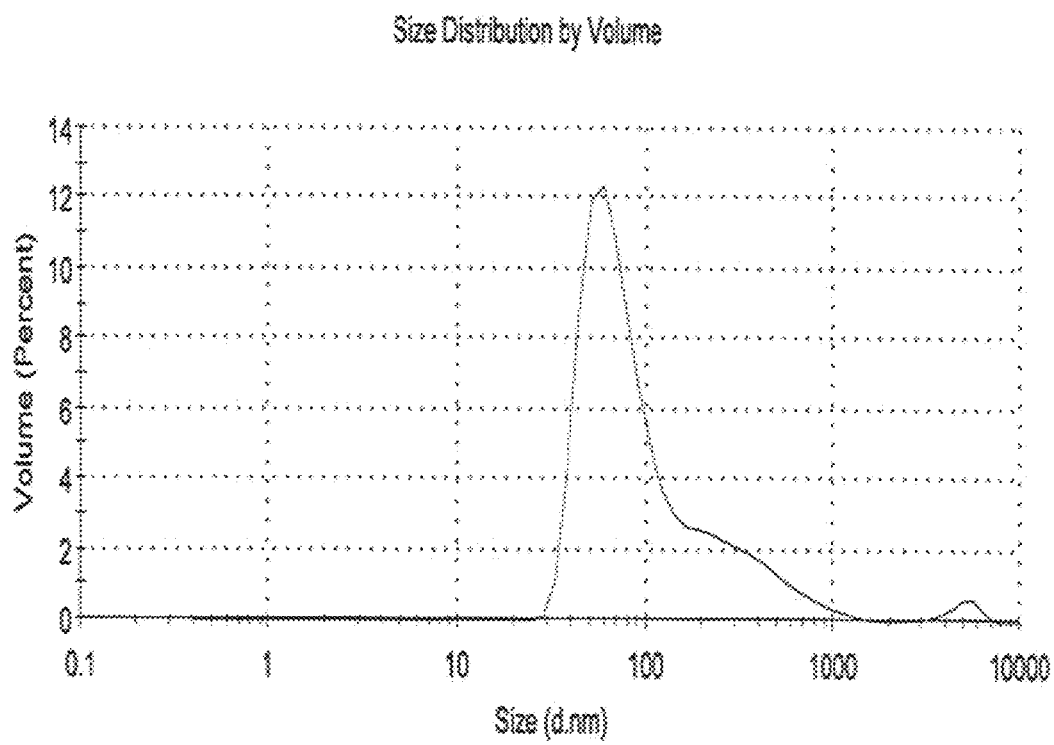

FIGS. 5A and 5B: Pharmaceutical DIM SMEDDS Oil in Water Dispersion Globule Volume. Globule Size Distribution Charts comparing DIM Pharmaceutical SMEDDS Formulation "G" with poloxamer and with phosphatidyl choline (PC) with DIM Pharmaceutical SMEDDS Formulation "M" with poloxamer and without PC, showing contribution of PC to smaller globule diameter in nanometers (d.nm). (FIG. 5A) Pharmaceutical Formulation "G" with phosphatidyl choline (PC), globule diameter (d.nm). (FIG. 5B) Pharmaceutical Formulation "M" without phosphatidyl choline (PC), globule diameter (d.nm).

Figure 6A:
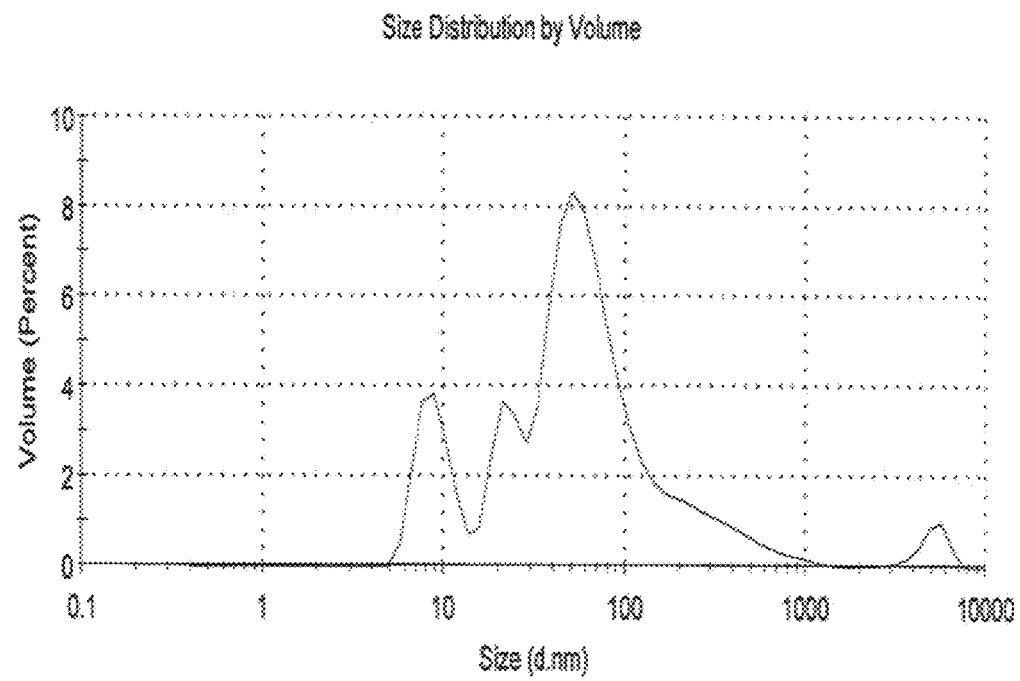
Figure 6B:
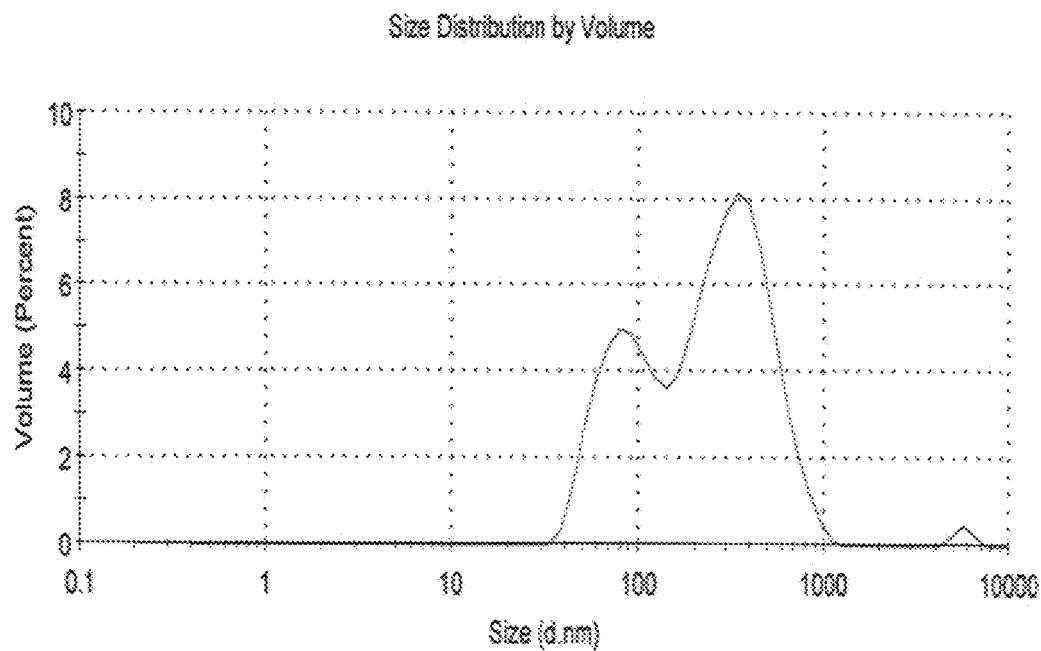

FIGS. 6A and 6B: Nutritional DIM SMEDDS Oil in Water Dispersion Globule Volume. Globule Size Distribution Charts comparing Nutritional DIM SMEDDS Formulation "N" with PC to Nutritional DIM SMEDDS Formulation "P" without PC showing contribution of PC to smaller globule diameter in nanometers (d.nm). (FIG. 6A) Nutritional Formulation "N" with phosphatidyl choline (PC), globule diameter (d.nm). (FIG. 6B) Nutritional Formulation "P" without phosphatidyl choline (PC), globule diameter (d.nm).

5. DETAILED DESCRIPTION

To develop DIM compositions with improved bioavailability and sustained absorption, the inventors developed self-emulsifying DIM compositions (SEDDS or SMEDDS DIM compositions), which required testing multiple excipients and combination of excipients and identifying mixtures of excipients that are highly miscible and specifically matched to the solubilization requirements of DIM as an API. Development of such compositions providing DIM in a dissolved state and resulting in self-emulsification and limited re-crystallization in the gastro-intestinal environment yielded DIM compositions and formulations having improved bioavailability, in particular, improved oral bioavailability.

In particular, the present invention is the result of the discovery of specific combinations of carrier excipients (including carrier solvents, surfactants and co-surfactants) that dissolve crystalline 3,3' diindolylmethane (DIM) forming pre-concentrates that can accommodate a high percentage of DIM. Upon ingestion and exposure to the intestinal mileau, the pre-concentrate spontaneously emulsifies to form a dispersion of fine oil-in-water emulsion globules increasing the gastrointestinal exposure and systemic absorption of DIM.

Arriving at the desired self-emulsifying DIM compositions, including their individual components and the mixture of the components, required investigation of the physicochemical characteristics of DIM, specifically, the solubility of DIM in various components and the mutual miscibility of the components. The compositions described herein yield DIM formulations that achieve markedly increased oral bioavailability of DIM compared to that of crystalline DIM.

In order to develop the compositions described herein, the inventors first assessed the relevant physicochemical characteristics of DIM and certain DIM-related indoles. These physicochemical properties were not predictable from those of Indole-3-carbinol, the monomeric indolylic precursor to DIM which is water soluble and highly unstable in acid.

The inventors found that, when tested in water, DIM demonstrated a maximal solubility of 0.7 µg/ml. When tested in an aqueous acid environment of pH 2, which is similar to the human gastric environment, DIM's solubility was essentially unchanged with a maximal solubility of 0.6 µg/ml. Further, DIM has demonstrated stability in neutral and acidic media and a middle range of lipid solubility.

Evaluation of the log P of DIM was necessary to guide the choice of potential excipients from which to develop prototype self-emulsifying DIM formulations. The inventors further determined that the experimental log P of DIM is 3.583. Based on a Log P of 3.583, DIM is a molecule of uncertain formulation requirements since the log P is not greater than 5. A log P of greater than 5 is generally required for an API to be amenable to increased lymphatic based absorption (see Trevaskis et al., 2008, Lipid-based delivery systems and intestinal lymphatic drug transport: a mechanistic update, Adv Drug Deliv Rev. 60(6):702-16). A log P of 3.583 and in the range of 3 and greater also indicates poor water solubility and difficulty for formulations to increase water solubility sufficiently to enter hepatic portal venous blood. A log P of 3.583 for DIM further indicates intermediate lipid solubility for DIM.

Based on the physicochemical characteristics of DIM, the inventors identified a group of DIM-related indoles which, based on their calculated log P values, are expected to possess physicochemical and solubility properties similar to those of DIM, and thus, are expected to have the same formulation requirements as DIM. Accordingly, the compositions or formulations described herein encompass compositions comprising, as an active ingredient, a DIM-related indole with log P between 3 and 5.5 or between 3.2 and 5 (which may be an experimentally-determined log P or a calculated log P). Such DIM-related indoles include, without limitation, 2,2-bis(3,3'indolyl)acetaldehyde and 2-indol-3-ylmethyl)-3,3'-Diindolylmethane (LTR).

Further, the inventors of the present invention identified through experimentation compatible carrier excipients (including carrier solvents, surfactants and co-surfactants) for self-emulsifying compositions of DIM-related indoles. This was accomplished by determining how DIM dissolves in the tested excipients from each class of excipients (i.e., carrier solvents, surfactants and co-surfactants) individually. Only a small subset of potential excipients showed both ability to dissolve DIM and also demonstrated mutual compatibility forming miscible stable mixtures. The inventors of the present invention also identified preferred mixtures of excipients (including preferred carrier solvents, surfactants and co-surfactants, and their combinations) from the excipients deemed to be the most compatible and interactive by the inventors, based on the solubility and stability of dissolved DIM in the mixtures. Preferred mixtures yielded DIM compositions characterized by continued solubility of DIM without recrystallization of DIM (or with reduced or minimal recrystallization of DIM) in the mixture of excipients (or upon dispersion in water or contact with intestinal fluids).

The inventors of the present invention further determined the most successful prototype self-emulsifying DIM compositions which retain solubilizing activity and produce the smallest oil-in-water emulsion globule size following spontaneous emulsification (e.g., on dispersion testing in aqueous media). The inventors of the present invention unexpectedly discovered that certain additives enhance DIM's solubility, thus, identifying additives with particularly advantageous DIM solubilizing characteristics. In particular, lecithin fractions rich in phosphatidyl choline in the mixture were found to confer advantages in self-emulsifying activity and reducing globule size.

The inventors of the present invention also developed particularly advantageous mixtures of carrier excipients that are capable of dissolving the most DIM per weight of the formulation, and thus, capable of maximizing drug loading capacity of the formulation.

The inventors of the present invention also unexepectedly discovered that the use of certain additives advantageously changes the behavior of the formulation to minimize re-crystallization on simulated digestion testing. In particular, long chain fatty acid triglycerides and poloxamer polymers were found to reduce globule size and minimize crystal formation Particularly advantageous among additives were poloxymer polymers (for example, at low concentration in the formulation).

The inventors of the present invention further identified food grade excipients, including Peppermint oil, a lauroyl polyoxyl-32 glyceride, propylene glycol monocaprylate, Polysorbate 80, and phosphatidyl choline, that can be used in the compositions and formulations described herein. The use of such food grade excipients in pharmaceutical and nutraceutical formulations contemplated herein can widen the scope of regulatory acceptance of such formulations.

The present invention encompasses self-emulsifying DIM compositions (such as those described herein) which show stability overtime without evidence of recrystallization of DIM in the formulation during shelf-life aging.

The inventors of the present invention also assessed whether the self-emulsifying DIM formulations described herein demonstrate compatibility with appropriate capsule forming materials including soft and hard shell gelatin capsules. They were found to be compatible.

Furthermore, the inventors of the present invention demonstrated that the self-emulsifying formulations developed for DIM demonstrate advantageous absorption, Cmax concentration levels, AUC exposure, and tolerability in animal and human testing. The inventors found that the self-emulsifying DIM compositions described herein do, in fact, show increased absorption Cmax concentration levels and AUC exposure in comparison to other absorption enhancing formulations and crystalline suspensions of DIM. Higher Cmax concentration levels and AUC exposure correlate with greater bioavailability, and thus, the self-emulsifying DIM formulations described herein possess greater bioavailability over other absorption enhancing formulations and crystalline suspensions of DIM. Because of these properties of the compositions and formulations of the invention, their use for pharmaceutical and nutraceutical purposes is expected to result in improved therapeutic responses relative to the use of other absorption enhancing formulations and crystalline suspensions of DIM.

Overall, the preferred DIM compositions developed by the inventors resulted in loading of the formulation with higher percentage of DIM, smaller globule size following spontaneous emulsification, modification of recrystallization of DIM during digestion and increased oral bioavailability of DIM compared to crystalline DIM and other absorption-enhanced non-SEDDS/non-SMEDDS formulations of DIM.

The present invention further encompasses methods of making pharmaceutical and nutraceutical formulations using self-emulsifying compositions of DIM and certain DIM-related indoles described herein. Such methods may comprise formulation steps that utilize volatile, non-toxic solvents to dilute the self-emulsifying compositions described herein while preserving the capacity to keep DIM in solution. In some embodiments, such diluted self-emulsifying DIM formulations are then applied to an absorbent delivery device or material and dried allowing the self-emulsifying formulation to be reconstituted.

In particular, provided herein are compositions comprising a DIM-related indole having log P from 3 to 5.5 and a carrier, wherein the carrier comprises a solvent, one or more surfactants with an HLB of greater than 7, and one or more co-surfactants with an HLB equal to or less than 7. Optionally, the carrier may also comprise one or more additional agents. Such one or more additional agents can comprise an agent that inhibits crystallization of the DIM-related indole, an agent that decreases the size of oil-in-water emulsion globules or particles (produced by the compositions described herein upon contact with intestinal fluid (which occurs upon ingestion) or dispersion in water), and/or an agent that increases oral bioavailability of a DIM-related indole (upon oral administration to a subject). Such one or more additional agents can, for example, comprise a triglyceride or a derivative thereof. Such one or more additional agents can, for example, comprise a polyethylene oxide polypropylene oxide block copolymer (such as $HO(C_2H_4O)_a(C_3H_6O)_b(C_2H_4O)_aH$). In specific embodiments, such one or more additional agents can comprise a poloxamer. In additional embodiments, such one or more additional agents can comprise a lecithin (e.g., phosphatidyl choline (PC)). Lecithins are co-surfactants with an HLB less than 7, and thus can be used as the "co-surfactant with an HLB of equal or less than 7" component of the compositions described herein, as well as an additional agent, in addition to one or more other co-surfactants with an HLB of equal or less than 7. Without being bound by any theory, triglycerides, poloxamers and/or lecithins may be used in the compositions described herein to reduce the size of oil-in-water emulsion globules carrying the API (such as DIM), prevent or reduce re-crystallization of the API (such as DIM), and increase oral bioavailability of the API (such as DIM). The individual components and properties of the compositions provided herein, as well as the dosing regimens and uses of such compositions, are described in more detail below.

5.1 DIM-Related Indoles for Use in the Compositions of the Invention

The DIM-related indoles for use in the compositions described herein have log P from 3 to 5.5 (which can be an experimentally-determined log P value or a calculated log P value, e.g., log P calculated using software known in the art such as ChemDraw Ultra 12.0 software (CambridgeSoft)). In some embodiments, a DIM-related indole used in the compositions described herein has log P from 3.0 to 5.2. In some embodiments, a DIM-related indole used in the compositions described herein has log P from 3.2 to 5.2. In some embodiments, a DIM-related indole used in the compositions described herein has log P from 3.2 to 5.5. In specific embodiments, a DIM-related indole used in the compositions described herein has log P from 3.2 to 5.0.

As used herein, "DIM-related compound," "DIM-related indole," and "DIM derivative" are used interchangeably, and refer to both natural metabolites and analogs of DIM, and also to "structurally-related, synthetically-derived, substituted diindolylmethane compounds" and "synthetic derivatives of DIM", such as those disclosed herein and known in the art. Such DIM-related compounds encompassed herein are those DIM-related compounds that have log P from 3.0 to 5.5. One of ordinary skill in the art will recognize that in any of the compositions of the invention where DIM is used, a DIM-related compound, including a structurally-related, synthetically-derived, substituted diindolylmethane compound or synthetic derivative of DIM, can be used as long as its log P is from 3.0 to 5.5. The DIM-related indoles useful in the compositions of the invention include DIM (3,3'-diindolylmethane) and the related linear DIM trimer (2-(indol-3-ylmethyl)-3,3'-diindolylmethane [also written: 2 (Indol-3-ylmethyl)-indol-3-yl]indol-3-ylmethane] (LTR).

The chemical structure of a DIM is as follows (where each of the R groups is H):

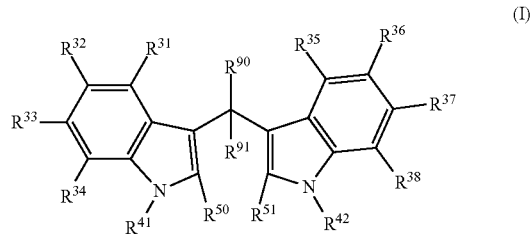

(I)

In particular embodiments, the DIM-related indole is a compound of formula I, wherein $R^{42}$, $R^{51}$, $R^{35}$, $R^{36}$, $R^{37}$, $R^{38}$, $R^{90}$, $R^{41}$, $R^{50}$, $R^{31}$, $R^{32}$, $R^{33}$, $R^{34}$ and $R^{91}$ individually and independently, are hydrogen or a substituent selected from the group consisting of a halogen, a hydroxyl, a nitro, —$OR^{100}$, —CN, —$NR^{100}R^{101}$, —$NR^{100}R^{101}R^{102+}$, —$COR^{100}$, $CF_3$, —S(O)n$R^{100}$ (n=02), —$SO_2NR^{100}R^{101}$, —$CONR^{100}R^{101}$, —$NR^{100}R^{101}$, —$NR^{100O}COR^{101}$, —$NR^{100}C(O)NR^{101}R^{102}$, —$P(O)(OR^{100})_n$ (n=1-2), optionally substituted alkyl, halovinyl, alkenyl, alkynyl, aryl, heteroalkyl, heteroaryl, or optionally substituted cycloalkyl or cycloakenyl, all of one to ten carbons and optionally containing 1-3 heteroatoms O or N, wherein $R^{100}$, $R^{101}$ and $R^{102}$ are optionally substituted alkyl, alkenyl, alkynl, aryl, heteroalkyl, heteroaryl of one to ten carbons, and $R^{90}$ and $R^{91}$ may further be O to create a ketone. In particular embodiments, the compound includes at least one such substituent, preferably at a position other than, or in addition to $R^{42}$ and $R^{41}$, the linear or branched alkyl or alkoxy group is one to five carbons, and/or the halogen is selected from the group consisting of chlorine, iodine, bromine and fluorine.

In particular embodiments, the indolyl moieties are symmetrically substituted, wherein each moiety is similarly mono-, di-, tri-, para-, etc. substituted. In other particular embodiments, $R^{42}$, $R^{51}$, $R^{35}$, $R^{37}$, $R^{38}$, $R^{90}$, $R^{41}$, $R^{50}$, $R^{31}$, $R^{33}$, $R^{34}$ and $R^{91}$ are hydrogen, and $R^{36}$ and $R^{32}$ are a halogen selected from the group consisting of chlorine, iodine, bromine and fluorine. Representative compounds include, but are not limited to, 3,3'-diindolylmethane, 5,5'-dichloro-diindolylmethane; 5,5'-dibromo-diindolylmethane; and 5,5'-difluoro-diindolylmethane. Additional DIM derivatives include compounds wherein $R^{42}$, $R^{51}$, $R^{35}$, $R^{37}$, $R^{38}$, $R^{90}$, $R^{41}$, $R^{50}$, $R^{31}$, $R^{33}$, $R^{34}$ and $R^{91}$ are hydrogen, and $R^{36}$ and $R^{32}$ are an alkyl or alkoxyl having from one to ten carbons, and preferably one to five carbons. Representative compounds include, but are not limited to, 5,5'-dimethyl-diindolylmethane, 5,5'-diethyl-diindolylmethane, 5,5'-dipropyl-diindolylmethane, 5,5'-dibutyl-diindolylmethane, 5,5'-dipentyl-diindolylmethane, 5,5'-dimethoxy-diindolylmethane, 5,5'-diethoxy-diindolylmethane, 5,5'-dipropyloxy-diindolylmethane, 5,5'-dibutyloxy-diindolylmethane, and 5,5'-diamyloxy-diindolylmethane.

Additional DIM derivatives include compounds wherein $R^{51}$, $R^{35}$, $R^{36}$, $R^{37}$, $R^{38}$, $R^{90}$, $R^{50}$, $R^{31}$, $R^{32}$, $R^{33}$, $R^{34}$ and $R^{91}$ are hydrogen, and $R^{42}$ and $R^{41}$ are an alkyl or alkoxyl having from one to ten carbons, and preferably one to five carbons. Representative compounds include, but are not limited to, N,N'-dimethyl-diindolylmethane, N,N'-diethyl-diindolylmethane, N,N'-dipropyl-diindolylmethane, N,N'-dibutyl-diindolylmethane, and N,N'-dipentyl-diindolylmethane. In yet another embodiment $R^{42}$, $R^{35}$, $R^{36}$, $R^{37}$, $R^{38}$, $R^{90}$, $R^{41}$, $R^{31}$, $R^{32}$, $R^{33}$, $R^{34}$ and $R^{91}$ are hydrogen, and $R^{51}$ and $R^{50}$ are alkyl of one to ten carbons, and preferably one to five carbons. Representative compounds include, but are not limited to, 2,2'-dimethyl-diindolylmethane, 2,2'-diethyl-diindolylmethane, 2,2'-dipropyl-diindolylmethane, 2,2'-dibutyl-diindolylmethane, and 2,2'-dipentyl-diindolylmethane. In another embodiment, $R^{42}$, $R^{51}$, $R^{35}$, $R^{37}$, $R^{38}$, $R^{90}$, $R^{41}$, $R^{50}$, $R^{31}$, $R^{33}$, $R^{34}$ and $R^{91}$ are hydrogen, and $R^{36}$ and $R^{32}$ are nitro.

In an alternative embodiment, active DIM derivatives with $R^{32}$ and $R^{36}$ substituents made up of ethoxycarbonyl groups, and $R^{50}$, $R^{51}$ are either hydrogen or methyl, are utilized.

In another embodiment, active substituted DIM derivatives including methylated and chlorinated compounds, exemplified by those that include 5,5'-dimethylDIM (5-Me-DIM), 2,2'-dimethylDIM (2-Me-DIM), and 5,5'-dichloroDIM (5-Cl-DIM) are described in U.S. Patent Application Publication No. 20020115708 by Safe, published Aug. 22, 2002, incorporated herein by reference in its entirety, are utilized in the present invention. In another embodiment, active DIM derivatives include imidazolelyl-3,3'-diindolylmethane, including nitro substituted imidazolelyl-3,3'-diindolylmethanes, and additional DIM-related compounds described in U.S. Patent Application Publication No. 2004/0043965 by Jong, Ling, published Mar. 4, 2004, incorporated herein by reference in its entirety, are utilized. In a further embodiment, active DIM derivatives described in U.S. Pat. Nos. 6,656,963, 6,369,095 and U.S. Patent Application Publication No. 20060229355 by Bjeldanes et al., published Oct. 12, 2006, incorporated herein by reference in its entirety, are utilized.

The chemical structure of LTR is as follows (where each of the R groups is H):

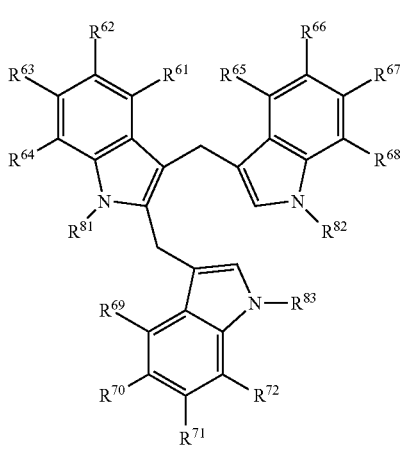

(II)

In certain embodiments, an active hydroxylated or methyoxylated metabolite of LTR, i.e., a compound of formula II, wherein $R^{62}$, $R^{63}$, $R^{66}$, $R^{67}$, $R^{70}$, and $R^{71}$ are substituents independently selected from the group consisting of hydrogen, hydroxyl, and methoxy, and $R^{61}$, $R^{64}$, $R^{65}$, $R^{68}$, $R^{69}$, $R^{72}$, $R^{81}$, $R^{82}$, and $R^{83}$ are hydrogen, is utilized.

In certain embodiments, a DIM related compound has formula (III):

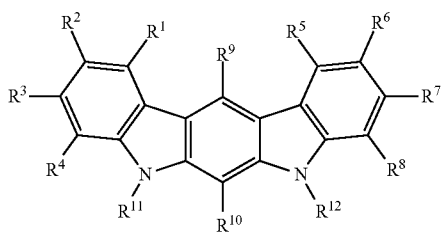

(III)

wherein: $R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the provisos that: at least one of $R^1$, $R^2$, $R^3$, $R^4$, $R^5$, $R^6$, $R^7$, $R^8$, $R^9$, $R^{10}$, $R^{11}$ and $R^{12}$ is other than hydrogen; and when $R^1$, $R^2$, $R^3$, $R^4$, $R^5$, $R^6$, $R^7$, and $R^8$ are selected from hydrogen, halo, alkyl and alkoxy, then $R^{11}$ and $R^{12}$ are other than hydrogen and alkyl.

In another embodiment, a DIM related compound has formula (IV):

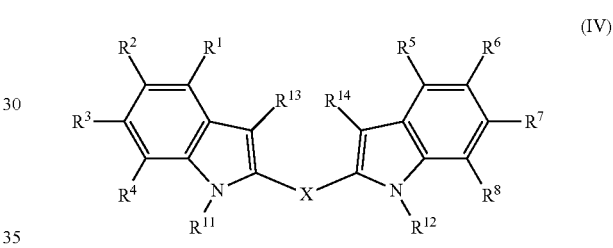

(IV)

wherein: $R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino; $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl; $R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form =$CR^{18}R^{19}$ where $R^{18}$ and $R^{19}$ are hydrogen or $C_1$-$C_6$ alkyl, and $R^{17}$ is as defined for $R^{11}$ and $R^{12}$.

In another embodiment, a DIM related compounds has formula (V):

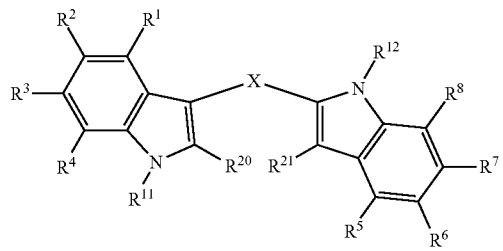

(V)

wherein: $R^1$, $R^2$, $R^3$, $R^4$, $R^5$, $R^6$, $R^7$, $R^8$, $R^{11}$, $R^{12}$, and X are defined as for compounds of formula (III); and $R^{20}$ and $R^{21}$ are defined as for $R^1$, $R^2$, $R^3$, $R^4$, $R^5$, $R^6$, $R^7$, and $R^8$.

In certain embodiments, a DIM-related indole used in the compositions described herein is any of the compounds described in U.S. Pat. No. 6,589,975 to Jacobs et al., which is incorporated by reference herein in its entirety (as long as log P of such compounds is from 3 to 5.5). In specific embodiments, a DIM-related indole used in the compositions described herein is a compound of the following formula described in U.S. Pat. No. 6,589,975 to Jacobs et al., which is specifically incorporated by reference herein in its entirety, as long as such compound has log P from 3 to 5.5 or, preferably, from 3.2 to 5.2:

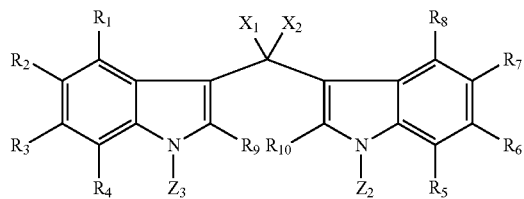

wherein $R_{1-10}$ are the same or different selected from —H, —OH, halogen, —COOH, —COOR, $C_1$-$C_8$ alkyl, $C_1$-$C_8$ alkoxyl, mesyl, tosyl, —OCOR, or $NZ_1Z_2$ (wherein the Zs can be the same or different);

$X_1$ and $X_2$ are the same or different selected from —H, —R, —COY, C(N$Z_1$)Y;

Y is —H, —OH, $NZ_1Z_2$ (wherein the $Z_1$, and $Z_2$ can be the same or different) $C_1$-$C_8$ alkyl, $C_1$-$C_8$ alkoxyl or an amino acid linked through the amine functionality forming an amide bond;

$Z_1$ and $Z_2$ are the same or different and independently selected from —H, —OH, $C_1$-$C_8$ alkyl, $C_1$-$C_8$ alkoxyl or —COR; and R is $C_1$-$C_8$ alkyl, or aryl.

In particular embodiments, a DIM-related indole used in the compositions described herein is Compound I, II or III described in U.S. Pat. No. 6,589,975 to Jacobs et al. (see col. 5), which are specifically incorporated by reference herein. In particular, compounds I, II and III are Soritin A, HB-238 (I), bis(3,3'indolyl)methane (II), and 2,2-bis(3,3'indolyl)acetaldehyde, HB-237 (III) having the following structures:

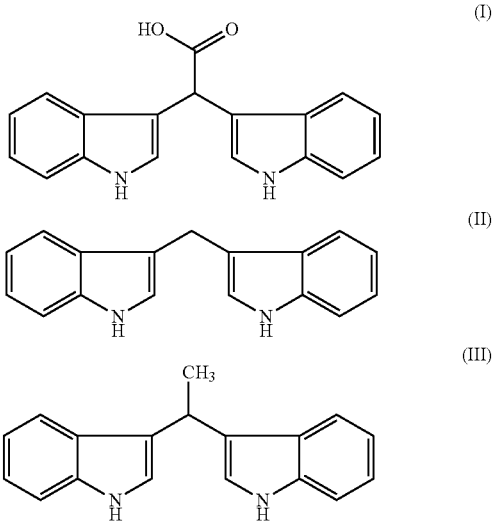

In certain embodiments, a DIM-related indole used in the compositions described herein is any of the compounds described in U.S. Pat. No. 6,323,233 to Wright et al. and U.S. Pat. No. 6,444,697 to Wright et al., each of which are incorporated by reference herein in their entireties (as long as log P of such compounds is from 3 to 5.5).

In preferred embodiments, a DIM-related indole used in the compositions described herein is an unsubstituted 3,3'-diindolylmethane compound or an unsubstituted 2,2'-diindolylmethane according to the following structures:

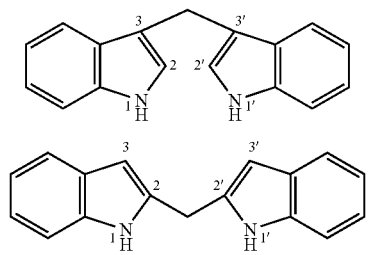

In a preferred embodiment, a DIM-related indole used in the compositions described herein is DIM.

In some embodiments, a DIM-related indole used in the compositions described herein is a substituted 3,3'-diindolylmethane compound or a substituted 2,2'-diindolylmethane wherein the R groups may be the same or different and are selected from hydrogen atoms, or from CH3:

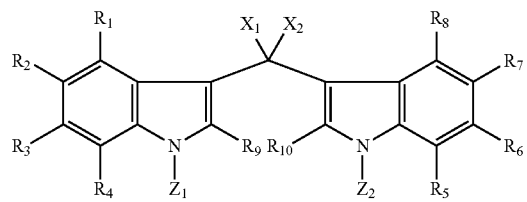

In some embodiments, a DIM-related indole used in the compositions described herein is a substituted 3,3'diindolylmethane where R and Z are hydrogen, X1 is hydrogen, and X2 is CH3 or X2 is hydrogen and X1 is CH3. In one embodiment, a DIM-related indole used in the compositions described herein is 2,2-bis(3,3'indolyl) acetaldehyde.

In some embodiments, a DIM-related indole used in the compositions described herein is a substituted 2,2'-diindolylmethane where R and Z are hydrogen, X1 is hydrogen, and X2 is CH3 or X2 is hydrogen and X1 is CH3. In one embodiment, a DIM-related indole used in the compositions described herein is 2,2-bis(2,2'indolyl) acetaldehyde.

In some embodiments, a DIM-related indole used in the compositions described herein is a substituted 3,3'-diindolylmethane compound or a substituted 2,2'diindolylmethane wherein the Z groups are CH3.

In some embodiments, a DIM-related indole used in the compositions described herein can be a substituted DIM derivative, including methylated, chlorinated or fluorinated compounds, that include, without limitation, 5,5'-dimethyl-DIM (5-Me-DIM), 2,2'-dimethylDIM (2-Me-DIM), and 5,5'-dichloroDIM (5-Cl-DIM). n one embodiment, a DIM-related indole used in the compositions described herein is 5,5'-difluoroDIM (5-Cl-DIM). Such compounds are described in U.S. Patent Publication No. 20020115708 by Safe, which is incorporated herein by reference in its entirety. Such compounds described in U.S. Patent Publication No. 20020115708 can be utilized in the compositions described herein.

In one embodiment, a DIM-related indole used in the compositions described herein is 2-(indol-3-ylmethyl)-3,3'-diindolylmethane (also known as 2 (Indol-3-ylmethyl)-indol-3-yl]indol-3-ylmethane, or "LTR"). The chemical structure of LTR is as follows (where each of the R groups is H):

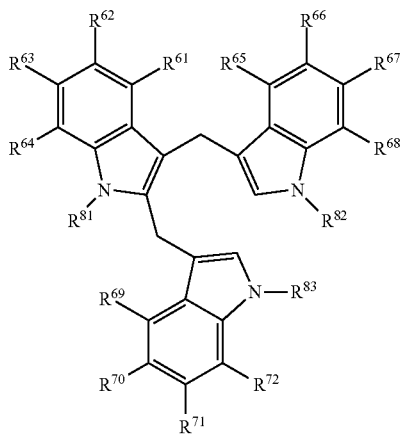

The DIM-related indoles encompassed by the present invention do not include P-DIM. The DIM-related indoles encompassed by the present invention do not include indole-3-carbinol.

5.2 Solvents for Use in the Compositions of the Invention

The solvents for use in the compositions described herein include, without limitation, Caprylocaproyl polyoxyl-8 glyceride, diethylene glycol monoethyl ether, propylene glycol, essential oils and lipids. In certain embodiments, solvents for use in the compositions described herein include, without limitation, a carylocaproyl polyoxyl-8 glyceride, a diethylene glycol monoethyl ether, propylene glycol, rice germ oil, rice bran oil, Capmul MCM $C_8$, Capmul PG8, Lauroglycol FCC, ethyl myristate, green lipped muscle oil, and krill oil. In some embodiments, the solvent is a lipid or an oil (e.g., essential oil). Essential oils for use in the compositions and methods described herein include, without limitation, peppermint oil, orange oil, lemon oil, limonene, lime oil, clove oil, mustard oil, black cumin oil, tea tree oil, wintergreen oil, lavender oil, ginger oil, nutmeg oil, fennel oil, eucalyptus oil, rosemary oil, borage oil, rice germ oil, rice bran oil, pomegranate (Punica granatum Linn., Punicaceae) seed oil, and sunflower oil. In some embodiments, the essential oil is peppermint oil, orange oil, lemon oil, limonene, lime oil, clove oil, mustard oil, black cumin oil, tea tree oil, wintergreen oil, lavender oil, ginger oil, nutmeg oil, fennel oil, eucalyptus oil, rosemary oil, borage oil, rice germ oil, rice bran oil, pomegranate (Punica granatum Linn., Punicaceae) seed oil, or cinnamon bark oil (*Cinnamomum zeylanicum*). Lipids for use in the compositions and methods described herein include, without limitation, glycerol mono- and di-esters and tri-esters. Solvent oils that can be used in the compositions of the present invention include, without limitation, triglycerides with long chain fatty acids, such as oleic acid, myristic acid, caprylic acid, capric acid rapeseed oil, sesame oil, safflower oil, and sunflower oil. In some embodiments, the solvent oil is not olive oil or sunflower oil.

In some embodiments, the solvent is in an amount greater than or equal to 4% or 5% by weight in the compositions described herein. In certain embodiments, the solvent is in an amount from 4% to 55% by weight or from 5% to 55% by weight in the compositions described herein. In specific embodiments, the solvent is in an amount from 5% to 55% or from 5% to 50% by weight. In some embodiments, the solvent is in an amount of at least 10%, at least 15%, at least 20% or at least 25% by weight in the compositions described herein. In specific embodiments, the solvent is in an amount from 10% to 55% by weight, from 10% to 50% by weight, from 15% to 55% by weight, from 15% to 50% by weight, from 20% to 55% by weight, from 20% to 50% by weight, from 25% to 55% by weight, or from 25% to 50% by weight.

In specific embodiments, a diethylene glycol monoethyl ether is in the amount from 30 to 45% by weight. In one embodiment, a diethylene glycol monoethyl ether is in the amount of at least 20% by weight. In one embodiment, a diethylene glycol monoethyl ether is in the amount of at least 25% by weight. In one embodiment, a diethylene glycol monoethyl ether is in the amount of at least 30% by weight. In one embodiment, a diethylene glycol monoethyl ether is in the amount of at least 35% by weight.

In specific embodiments, a caprylocaproyl polyoxyl-8 glyceride is in the amount from 25% to 55% by weight. In one embodiment, a caprylocaproyl polyoxyl-8 glyceride is in the amount of at least 20% by weight. In one embodiment, a caprylocaproyl polyoxyl-8 glyceride is in the amount of at least 25% by weight. In one embodiment, a caprylocaproyl polyoxyl-8 glyceride is in the amount of at least 30% by weight. In one embodiment, a caprylocaproyl polyoxyl-8 glyceride is in the amount of at least 40% by weight.

In specific embodiments, peppermint oil is in the amount of 5% to 15% by weight in the compositions described herein. In one embodiment, peppermint oil is in the amount of at least 5% by weight in the compositions described herein. In one embodiment, peppermint oil is in the amount of at least 8% by weight in the compositions described herein. In one embodiment, peppermint oil is in the amount of about 10% or at least 10% by weight in the compositions described herein. In specific embodiments, rosemary oil is in the amount of 5% to 15% by weight in the compositions described herein. In one embodiment, rosemary oil is in the amount of at least 5% by weight in the compositions described herein. In one embodiment, roseamry oil is in the amount of at least 8% by weight in the compositions described herein. In one embodiment, rosemary oil is in the amount of about 10% or at least 10% by weight in the compositions described herein.

In particular embodiments of nutritional or nutraceutical compositions and formulations described herein, the solvent is an essential oil, e.g., peppermint oil. In specific embodiments of nutritional or nutraceutical compositions and formulations described herein, the solvent is rosemary oil. In other particular embodiments of nutritional or nutraceutical compositions and formulations described herein, the solvent is propylene glycol. In some embodiments of nutritional or nutraceutical compositions described herein, the solvent is in an amount from 3% to 15% by weight, or, more specifically from 5% to 10% by weight in the compositions described herein. In some embodiments of nutritional or nutraceutical compositions described herein, the solvent is in an amount from 7% to 20% by weight.

In particular embodiments of pharmaceutical compositions and formulations described herein, the solvent is a caprylocaproyl polyoxyl-8 glyceride or a diethylene glycol monoethyl ether. In some embodiments of pharmaceutical compositions described herein, the solvent is in an amount from 10% to 40% by weight, or, more specifically, from 20% to 30% by weight in the compositions described herein (e.g., for pharmaceutical compositions described herein). In some embodiments of pharmaceutical compositions described herein, the solvent is in an amount from 20% to 55%, from 25% to 55%, from 20% to 50% or from 25% to 50% by weight.

One or more solvents can be used in the compositions described herein. In some embodiments, one type of solvent is used in the compositions of the invention. In other embodiments, two or more different solvents are used in the compositions of the invention.

In certain embodiments, the solvent used in the compositions described herein is not an Enova oil and/or is not Cremophor EUL.

5.3 Surfactants with an HLB Greater than 7 for Use in the Compositions of the Invention The surfactants for use in the compositions described herein are surfactants with an HLB greater than 7. Such surfactants include surfactants with an HLB greater than 7 described in this application and known in the art. The HLB values of some of the surfactants with an HLB greater than 7 that can be used in the compositions described herein can be found, e.g., in Griffin, W M, 1954, Journal of the Society of Cosmetic Chemists 5 (4): 249-56, which is incorporated by reference herein in its entirety.

The surfactants with an HLB greater than 7 for use in the compositions described herein include, without limitation, polysorbates (polyethylene glycol sorbitan fatty acid esters), polyethylene glycol alkyl ethers, sugar esters, polyoxyethylated fatty acids, citric acid esters of monoglycerides, polyglycerol esters, polyoxyethylated fatty acid diesters, polyethylene glycol glycerol fatty acid esters, polyoxyethylated castor oil, and polyoxyethylated hydrogenated castor oil.

One or more surfactants with an HLB greater than 7 are contemplated for use in the compositions described herein.

In certain embodiments, provided herein are compositions wherein the one or more surfactants with an HLB of greater than 7 comprise polyoxyethylelene sorbitan monooleate (such as Polysorbate 80), a lauroyl polyoxyl 32 glyceride or a polyoxyethyl hydroxyl stearate.

In one embodiment, the compositions described herein do not comprise Polysorbate 80. In particular, in some embodiments, the pharmaceutical compositions described herein do not comprise polyoxyethylelene sorbitan monooleate (e.g., do not comprise Polysorbate 80). In other embodiments, the compositions described herein comprise Polysorbate 80. In particular, in some embodiments, the nutritional or nutraceutical compositions described herein comprise polyoxyethylelene sorbitan monooleate (e.g., comprise Polysorbate 80). In some of these embodiments, the compositions described herein comprise relatively low formulation percentage of polyoxyethylelene sorbitan monooleate (such as Polysorbate 80). For example, in some embodiments, the compositions described herein comprise less than 35% of polyoxyethylelene sorbitan monooleate (such as Polysorbate 80). In one embodiment, the compositions described herein comprise less than 30% of polyoxyethylelene sorbitan monooleate (such as Polysorbate 80). In specific embodiments, the compositions described herein comprise 25% or less than 25% to as low as 5% of polyoxyethylelene sorbitan monooleate (such as Polysorbate 80). In one embodiment, the compositions described herein comprise less than 10% polyoxyethylelene sorbitan monooleate (such as Polysorbate 80).

In some embodiments, the compositions provided herein comprise at least two surfactants with an HLB greater than 7 (such as any of the surfactants with HLB greater than 7 described herein or known in the art).

In certain embodiments, the surfactant with an HLB of greater than 7 is in an amount of at least or more than 10%, more than 12%, more than 15%, more than 17.5%, more than 20% or more than 25% by weight in the compositions described herein. In some embodiments, the surfactant with an HLB of greater than 7 is in an amount from 10% to 70% or from 10% to 60% by weight in the compositions described herein. In particular embodiments, the surfactant with an HLB of greater than 7 is in an amount from 15% to 30% or from 18% to 25% by weight in the compositions described herein. In specific embodiments, the surfactant with an HLB of greater than 7 is in an amount from 30% to 65% by weight, from 40% to 60% by weight, or from 50% to 60% by weight in the compositions described herein. In specific embodiments, the surfactant with an HLB of greater than 7 is in an amount from 20% to 50% by weight in the compositions described herein. The compositions described herein may comprise, in some embodiments, the surfactant with an HLB of greater than 7 is in an amount of at least 8% by weight in the compositions described herein. In some embodiments, the surfactant with an HLB of greater than 7 is in an amount of at least 10% by weight in the compositions described herein. In other embodiments, the surfactant with an HLB of greater than 7 is in an amount of at least 15% by weight in the compositions described herein. In yet other embodiments, the surfactant with an HLB of greater than 7 is in an amount of at least 20% by weight in the compositions described herein. In some embodiments, the surfactant with an HLB of greater than 7 is in an amount of at least 25% by weight in the compositions described herein. In additional embodiments, the surfactant with an HLB of greater than 7 is in an amount of at least 30% by weight in the compositions described herein. In additional embodiments, the surfactant with an HLB of greater than 7 is in an amount of less than 50% by weight in the compositions described herein.

In specific embodiments, Polysorbate 80 is in the amount from 15 to 30% or from 20% to 30% by weight in the compositions described herein. In additional embodiments, Polysorbate 80 is in the amount of at least 5% or 10% by weight in the compositions described herein. In some embodiments, Polysorbate 80 is in the amount of less than 25% by weight in the compositions described herein.

In other specific embodiments, a mixture of monoesters and diesters of 12-hydroxystearic acid and macrogols is in an amount from 10% to 20% by weight in the compositions described herein. In one embodiment, a mixture of monoesters and diesters of 12-hydroxystearic acid and macrogols is in an amount of at least 10% by weight in the compositions described herein.

In other specific embodiments, a lauroyl polyoxyl-32 glyceride is in the amount of 15% to 25% or from 17% to 20% by weight in the compositions described herein. In another embodiment, a lauroyl polyoxyl-32 glyceride is in the amount of 30% to 40% or from 18% to 35% by weight in the compositions described herein. The compositions described herein may comprise, in some embodiments, a lauroyl polyoxyl-32 glyceride is in the amount of at least 8% by weight in the compositions described herein. In some embodiments, a lauroyl polyoxyl-32 glyceride is in the amount of at least 10% by weight in the compositions described herein. In other embodiments, a lauroyl polyoxyl-32 glyceride is in the amount of at least 15% by weight in the compositions described herein. In yet other embodiments, a lauroyl polyoxyl-32 glyceride is in the amount of at least 18% by weight in the compositions described herein. In another embodiment, a lauroyl polyoxyl-32 glyceride is in the amount of at least 20% by weight in the compositions described herein. In some embodiments, a lauroyl polyoxyl-32 glyceride is in the amount of at least 25% by weight in the compositions described herein. In additional embodiments, a lauroyl polyoxyl-32 glyceride is in the amount of at least 30% by weight in the compositions described herein.

In some embodiments of the pharmaceutical compositions described herein, the surfactants with an HLB of greater than 7 are in an amount from 15 to 30% or from 20% to 30% by weight. In some embodiments of the nutritional or nutraceutical compositions described herein, the surfactants with an HLB of greater than 7 are in an amount from 50 to 65% by weight.

In one embodiment, the surfactant with HLB greater than 7 is TPGS. TPGS has HLB of greater than 13.2. In another embodiment, the surfactant with an HLB greater than 7 is not TPGS. In specific embodiments, the nutritional or nutraceutical compositions described herein do not comprise TPGS. In other specific embodiments, the pharmaceutical compositions described herein do not comprise TPGS.

5.4 Co-Surfactants with an HLB Equal to or Less than 7 for Use in the Compositions of the Invention The co-surfactants for use in the compositions described herein are co-surfactants with an HLB equal to or less than 7. Such co-surfactants include any surfactants with an HLB equal to or less than 7 described in this application and known in the art. The HLB values for some of the surfactants with an HLB equal to or less than 7 that can be used in the compositions described herein can be found, e.g., in Griffin, W M, 1954, Journal of the Society of Cosmetic Chemists 5 (4): 249-56, which is incorporated by reference herein in its entirety.

The co-surfactants with an HLB equal to or less than 7 for use in the compositions described herein include, without limitation, sorbitan fatty acid esters, glyceryl mono- and di-esters, low number (<10) polyoxyethylene glyceryl mono-, di- and tri-esters, polyglyceryl di-oleate, polyglyceryl di-isostearate, poly glyceryl-6-octastearate, polyglyceryl-10 deca-oleate, polyoxythylated corn oil, and polyoxyethylated apricot kernel oil.

One or more co-surfactants with an HLB equal to or less than 7 are contemplated for use in the compositions described herein.

In certain embodiments, provided herein are compositions wherein the one or more co-surfactants with an HLB equal to or less than 7 comprise propylene glycol caprylate or a phosphatidic acid derivative thereof (such as propylene glycol monocaprylate).

In certain embodiments, provided herein are compositions wherein the one or more co-surfactants with an HLB equal to or less than 7 comprise a phospholipid. Any phospholipids known in the art can be used in the compositions of the invention.

In certain embodiments, provided herein are compositions wherein the one or more co-surfactants with an HLB equal to or less than 7 comprise a lecithin. (e.g., phosphatidyl choline or lysophosphatidyl choline).

Lecithin is a generic term to designate any group of yellow-brownish fatty substances occurring in animal and plant tissues composed of phosphoric acid, choline, fatty acids, glycerol, glycolipids, triglycerides, and phospholipids (e.g., phosphatidylcholine, phosphatidylethanolamine, and phosphatidylinositol). Any lecithin known in the art can be used in the compositions of the invention. In some embodiments, lecithin concentrated in phophatidyl choline is used in the compositions of the invention. In one embodiment, the compositions of the invention comprise a lecithin comprising at least 50% or more than 90% of phosphatidyl choline.

Phosphatidyl choline from any sources known in the art can be used in the compositions of the invention. For example, phosphatidyl choline from various sources of natural origin can be used. Alternatively, or in addition, phosphatidyl choline of synthetic origin can be used. See, for example, a publication by van Hoogevest & Wendel (Hoogevest & Wendel, 2014, The use of natural and synthetic phospholipids as pharmaceutical excipients, Eur J Lipid Sci Technol. 116(9):1088-1107), describing various phospholipids, such as phosphatidyl choline, as pharmaceutical excipients. The contents of Hoogevest & Wendel (2014, Eur J Lipid Sci Technol. 116(9):1088-1107) are incorporated by reference herein in their entirety. In particular, the compositions described herein may include phospholipids, such as phosphatidyl choline, described in Hoogevest & Wendel, which are specifically incorporated by reference herein.

In certain embodiments, the lecithin is in an amount of at least or more than 4% by weight in the compositions described herein. In some embodiments, the lecithin is in an amount from 4% to 10% by weight in the compositions described herein. In particular embodiments, the lecithin is in an amount from 6% to 9% by weight in the compositions described herein.

In certain embodiments, the co-surfactant with an HLB equal to or less than 7 is in an amount of at least or more than 3%, 4%, 5%, 6%, 7%, or 8% by weight in the compositions described herein. In some embodiments, the co-surfactant with an HLB equal to or less than 7 is in an amount from 3% to 30%, from 3% to 25%, or from 4% to 20% by weight in the compositions described herein. In some embodiments, the co-surfactant with an HLB equal to or less than 7 is in an amount from 3% to 10%, from 3% to 15%, from 3% to 20%, from 4% to 10%, from 4% to 15%, from 4% to 20%, from 4% to 30% or from 4% to 25% by weight in the compositions described herein. In particular embodiments, the co-surfactant with an HLB of less than 7 is in an amount from 5% to 25%, from 7% to 25%, from 5% to 20%, from 8% to 20%, from 5% to 10% or from 5% to 15% by weight in the compositions described herein. In one embodiment, the co-surfactant with an HLB equal to or less than 7 is in the amount of at least 4% by weight in the compositions described herein. In one embodiment, the co-surfactant with an HLB equal to or less than 7 is in the amount of at least 8% by weight in the compositions described herein. In one embodiment, the co-surfactant with an HLB equal to or less than 7 is in the amount of at least 10% by weight in the compositions described herein.

In specific embodiments, propylene glycol caprylate or a phosphatidic acid derivative thereof (e.g., propylene glycol monocaprylate) is in the amount from 3% to 20%, from 4% to 15%, or from 7% to 15% by weight in the compositions described herein. In one embodiment, propylene glycol caprylate or a phosphatidic acid derivative thereof (e.g., propylene glycol monocaprylate) is in the amount from 8% to 20% by weight in the compositions described herein. In one embodiment, propylene glycol caprylate or a phosphatidic acid derivative thereof (e.g., propylene glycol monocaprylate) is in the amount from 8% to 16% by weight in the compositions described herein. In one embodiment, propylene glycol caprylate or a phosphatidic acid derivative thereof (e.g., propylene glycol monocaprylate) is in the amount of at least 4% by weight in the compositions described herein. In one embodiment, propylene glycol caprylate or a phosphatidic acid derivative thereof (e.g., propylene glycol monocaprylate) is in the amount of at least 8% by weight in the compositions described herein. In one embodiment, propylene glycol caprylate or a phosphatidic acid derivative thereof (e.g., propylene glycol monocaprylate) is in the amount of at least 10% by weight in the compositions described herein.

In some embodiments, phosphatidyl choline (such as Phospholipon 85G) is in the amount from 3% to 15%, from 4% to 12%, from 7% to 15%, or from 7% to 12% by weight in the compositions described herein. In specific embodiment, a lecithin such as phosphatidyl choline (e.g., Phospholipon 85G) is in the amount of at least or more than 4%, 5%, 6%, 7%, 7.5%, 8%, 9% or 10% by weight in the compositions described herein. In preferred embodiments, a lecithin such as phosphatidyl choline (e.g., Phospholipon 85G) is in the amount of at least or more than 3% to 15% by weight in the compositions described herein. In one embodiment, phosphatidyl choline is in the amount of at least 4% by weight in the compositions described herein (e.g., 7% to 15%, or 8% to 15%). In one embodiment, phosphatidyl choline is in the amount of at least 7% by weight in the compositions described herein (e.g., 7% to 15%, or 8% to 15%). In one embodiment, phosphatidyl choline is in the amount of at least 10% by weight in the compositions described herein. In some embodiments of the pharmaceutical compositions described herein, the co-surfactant with an HLB equal to or less than 7 is in an amount from 15 to 30% or from 3% to 15% by weight. In some embodiments of the nutritional or nutraceutical compositions described herein, the co-surfactant with an HLB equal to or less than 7 is in an amount from 10 to 20% by weight.

In some embodiments, the compositions provided herein comprise at least two co-surfactants with HLB equal to or less than 7. In some of these embodiments, at least one of the two or more co-surfactants with HLB equal to or less than 7 is a lecithin (e.g., phosphatidyl choline).

5.5 Additional Excipients for Optional Use in the Compositions of the Invention Optionally, the compositions described herein further comprise one or more additional agents. Such one or more additional agents can comprise, without limitation, an agent that inhibits crystallization of the DIM-related indole, an agent that decreases the size of oil-in-water emulsion globules or particles (produced by the compositions described herein upon contact with intestinal fluids, such as after ingestion by a subject, or upon dispersion in water), and/or an agent that increases oral bioavailability of a DIM-related indole (upon oral administration to a subject). Such one or more additional agents can, for example, comprise a triglyceride or a derivative thereof. Such one or more additional agents can, for example, comprise a polymer such as a poloxamer, or a derivatized cellulose.

In certain embodiments, provided herein are compositions wherein the carrier further comprises a derivatized cellulose that is soluble in the composition, a polyoxythene/polyoxypropylene copolymer (known as poloxamer), polyvinyl acetate phthalate, or polyvinyl pyrolidone. In specific embodiments, the compositions provided herein comprise at least 5% by weight of such additions agent(s). In other specific embodiments, the compositions provided herein comprise at least 10% by weight of such additions agent(s).

In certain embodiments, provided herein are compositions wherein the carrier further comprises a polyoxythene/polyoxypropylene copolymer. In the polyoxythene/polyoxypropylene copolymer, the monomers, which are ethylene oxide and propylene oxide, are in blocks rather than randomly distributed. The hydrophilic block is the polymer portion from polyethylene oxide blocks and the hydrophobic block is the polymer portion from polypropylene blocks. In particular embodiments, the carrier comprises a poloxamer, for example, a poloxamer wherein the molecular mass of the hydrophobic block of the poloxamer is greater than 50% of the total molecular mass of the poloxamer and the molecular mass of the hydrophilic block of the poloxamer is less than 2250 Daltons. In one embodiment, the poloxamer is Poloxamer 124.

In certain embodiments, a poloxamer is in an amount of at least or more than 5% by weight in the compositions described herein. In certain embodiments, a poloxamer is in an amount of at least or more than 10% by weight in the compositions described herein. In certain embodiments, a poloxamer is in an amount of at least or more than 15% by weight in the compositions described herein. In certain embodiments, a poloxamer is in an amount of at least or more than 20% by weight in the compositions described herein. In some embodiments, a poloxamer is in an amount from 5% to 30% by weight in the compositions described herein. In particular embodiments, a poloxamer is in an amount from 15% to 25% by weight in the compositions described herein. In some embodiments, a poloxamer (e.g., Poloxamer 124) is in the amount from 10% to 50% in the compositions described herein. In specific embodiments, a poloxamer (e.g., Poloxamer 124) is in the amount from 20% to 30% in the compositions described herein. In some embodiments, a poloxamer is in an amount of less than 30% by weight in the compositions described herein. In some embodiments, a poloxamer is in an amount of less than 25% by weight in the compositions described herein. In some embodiments, a poloxamer is in an amount of less than 20% by weight in the compositions described herein. In some embodiments, a poloxamer is to be used in the pharmaceutical compositions described herein. In particular embodiments, the nutraceutical or nutritional compositions described herein do not comprise a poloxamer.

In some embodiments, the carrier comprises a derivatized cellulose. For example, the derivatized cellulose can be hydroxypropylmethyl cellulose, hydroxypropyl methyl cellulose acetate phthalate, or hydroxypropyl methyl cellulose acetate succinate.

In certain embodiments, provided herein are compositions wherein the carrier further comprises one or more triglycerides or polyoxyethylene derivatives of a triglyceride. Triglycerides that can be used in the compositions of the present invention include, without limitation, a medium chain triglyceride (also known as a Caprylic/Capric triglyceride), an oleoyl polyoxyl-6 glyceride, olive oil, and triglycerides with long chain fatty acids (such as oleic acid, myristic acid, caprylic acid, capric acid rapeseed oil, sesame oil, sunflower oil, and safflower oil). For example, the triglyceride or polyoxyethylene derivative of a triglyceride in the compositions provided herein can be a Caprylic/Capric triglyceride or an oleoyl polyoxyl-6 glyceride. In some embodiments, the triglycerides or polyoxyethylene derivatives of a triglyceride used in the compositions described herein are also co-surfactants with HLB equal to or less than 7.

In certain embodiments, the triglycerides or polyoxyethylene derivatives of a triglyceride are in an amount of at least or more than 0.5% by weight in the compositions described herein. In some embodiments, the triglycerides or polyoxyethylene derivatives of a triglyceride are in an amount from 1% to 20% by weight in the compositions described herein. In particular embodiments, the triglycerides or polyoxyethylene derivatives of a triglyceride are in an amount from 6% to 12% by weight in the compositions described herein. In some embodiments, triglycerides (or polyoxyethylene derivatives thereof) are in an amount from 7% to 25% in the compositions described herein. In one embodiment, triglycerides (or polyoxyethylene derivatives thereof) are in an amount from 10% to 20% in the compositions described herein. In one embodiment, triglycerides (or polyoxyethylene derivatives thereof) are in an amount from 7% to 12% in the compositions described herein (e.g., in pharmaceutical compositions described herein).

In specific embodiments, an oleoyl polyoxyl-6 glyceride is in an amount of at least or more than 0.5% by weight in the compositions described herein. In some embodiments, an oleoyl polyoxyl-6 glyceride is in an amount from 1% to 20% by weight in the compositions described herein. In particular embodiments, an oleoyl polyoxyl-6 glyceride is in an amount from 5% to 15% by weight in the compositions described herein. In one embodiment, an oleoyl polyoxyl-6 glyceride is in an amount from 7% to 12% in the compositions described herein. In one embodiment, an oleoyl polyoxyl-6 glyceride is in an amount from 8% to 10% in the compositions described herein.

In additional embodiments, a medium chain triglyceride is in an amount of at least or more than 0.5% by weight in the compositions described herein. In some embodiments, a medium chain triglyceride is in an amount from 1% to 20% by weight in the compositions described herein. In particular embodiments, a medium chain triglyceride is in an amount from 5% to 15% by weight in the compositions described herein. In one embodiment, an oleoyl polyoxyl-6 glyceride is in an amount from 7% to 12% in the compositions described herein. In one embodiment, an oleoyl polyoxyl-6 glyceride is in an amount from 8% to 12% in the compositions described herein. In one embodiment, an oleoyl polyoxyl-6 glyceride is in an amount from 9% to 11% in the compositions described herein.

5.6 Additional Active Agents (APIs) for Optional Use in the Compositions and Methods of the Invention In certain embodiments, the compositions and formulations provided herein comprise two or more biologically active agents (a DIM-related indole and one or more additional biologically active agents). In some of these embodiments, the additional biologically active agent in the compositions and formulations provided herein is a retinoid (e.g., retinyl palmitate), Vitamin D, melatonin, Vitamin K, bicalutamide, artemether or tamoxifen.

The present invention also encompasses compositions comprising, in addition to a DIM-related indole, one or more appropriately selected additional APIs. Criteria for selection of complementary API to be formulated together with a DIM-related indole (such as DIM) include: compatibility of complementary API's physicochemical characteristics indicating predominant lipid solubility, acceptable solubility in the DIM-specific solvent, surfactant, and co-surfactant components, and low dose loading requirements to allow co-solubilization with DIM in the self-emulsifying mixture. Favorable complimentary APIs do not interfere with or enhance bioavailability of DIM following spontaneous emulsification of compositions described here, and, optionally, inhibit recrystallization of DIM and/or do not recrystallize during digestion. The most favorable complimentary APIs that can be used in the compositions described herein are lipid compatible or lipid molecules which are also substrates and or inhibitors for a CYP 1A cytochrome enzyme (which is expected to support DIM bioavailability by reducing DIM presystemic and hepatic first-pass metabolism).

In certain embodiments, a second API compatible with the DIM compositions described herein is a retinoid compound related to Vitamin A, including, without limitation, retinol, retinal, and retinoic acid which are first generation retinoids. The retinoid second API may be selected from a substituted or unsubstituted first generation retinoid, a substituted or unsubstituted second generation retinoid and a substituted or unsubstituted third generation retinoid. More preferably the retinoid is a substituted or unsubstituted first generation retinoid. Typically, the first generation retinoid is selected from a substituted or unsubstituted retinol, a substituted or unsubstituted retinal, a substituted or unsubstituted tretinoin (e.g. retinoic acid or Retin A), a substituted or unsubstituted isotretinoin (13-cis retinoic acid), and a substituted or unsubstituted alitretinoin. Most preferably the retinoid comprises vitamin A. When the retinoid is a second generation retinoid, it is typically selected from a substituted or unsubstituted etretinate, and a substituted or unsubstituted acitretin. When the retinoid is a third generation retinoid, it is typically selected from a substituted or unsubstituted tazarotene, a substituted or unsubstituted bexarotene, and a substituted or unsubstituted adapalene. In one preferred embodiment, acitretin (which has a Log P of 5.73) is formulated according the present invention in combination with DIM in doses of 5-15 mg of acetretin in combination with 25-75 mg of DIM or DIM-related indole per dose (e.g., capsule). Typical daily dose of acetretin will require use of 1-5 doses (e.g., capsules) per day. In an additional embodiment, isotretinoin (13-cis retinoic acid) (which has a Log P of 6.83) is formulated according to the present invention in combination with DIM in doses of 10-20 mg of isotretinoin in combination with 25-75 mg of DIM or DIM-related indole per dose (e.g., capsule). Typical daily dose of isotretinoin will require use of 1-5 doses capsules per day.

In a preferred embodiment, the second API used in the compositions described herein is Retinyl Palmitate, which is a precursor to Vitamin A active forms, lipid compatible and useful in the therapy of skin conditions including acne, rosacea, and psoriasis. Retinyl palmitate has a log P of 5.68 indicating primarily lipid solubility. Typical Retinal Palmitate dosing is used in the range of 2 mg-13.75 mg (3,666 IU—25000 IU) per dose (e.g., for human use). Accordingly, in some embodiments, retinyl palmitate is used in the compositions and formulations described herein in the amount from 1.8 mg to 15 mg, 2 mg to 13.75 mg, or 2.75 mg to 10 mg per dose (e.g., per capsule) (e.g., in the amount of 2 mg, 3 mg, 4 mg, 5 mg, 6 mg, 7 mg, 8 mg, 9 mg, 10 mg, or any other value in between). In such embodiments, a DIM-related indole, such as DIM, can be used in an amount from 20 mg and 125 mg, or from 25 mg to 100 mg per dose (e.g., per capsule) (e.g., in the amount of 50 mg, 60 mg, 70 mg, 75 mg, 80 mg, 90 mg, 100 mg, or any other value in between). For example, Formulation J described in the Example section of this application (see Table 3) comprises, in addition to DIM, Retinyl Palmitate in the amount of 2 mg. In some embodiments of the SEDDS or SMEDDS compositions of the present invention comprising DIM and Retinyl Palmitate, DIM is in the amount of 75 mg DIM and Retinyl Palmitate is in the amount of 13.75 mg, per 800-1000 mg of the total composition. In some embodiments, second API is Vitamin D which is a lipid based nutritional agent with a log P of 7.5 and similar solubility characteristics to Retinyl Palmitate. In specific embodiments, Vitamin D is used in the compositions of the invention as a second API, instead of Retinyl Palmitate, in similar mg dose ranges. In other embodiments, the compositions described herein comprise a DIM-related indole (such as DIM), Retinyl Palmitate, and Vitamin D.

In other embodiments, the second API compatible with the DIM compositions described herein is melatonin, which is an indole neurohormone used as both a nutraceutical and pharmaceutical promote healthy sleep. Melatonin has a log P of 1.6 yet it is highly insoluble in water requiring a lipid based formulation technology for best bioavailability. Dose requirements for melatonin are from 2.5-10 mg per dose allowing for co-formulation with DIM compositions described herein. Typical melatonin dosing is compatible with the compositions described herein as demonstrated by Formulation O described in the Examples section of this application (see Table 4). Formulation O provides a unit dose of 100 mg DIM with 20 mg melatonin in 1000 mg of the total formulation. A preferred DIM/melatonin SEDDS or SMEDDS unit dose would comprise 25-50 mg DIM combined with 5-10 mg melatonin in 250-500 mgs or 300-400 mgs of SEDDS or SMEDDS formulation. A nutritional DIM/melatonin SEDDS or SMEDDS formulation can, for example, contain 25-30 mg, e.g., 30 mg, DIM and 5-10 mg of melatonin per dose (e.g., capsule). A pharmaceutical DIM/melatonin SEDDS or SMEDDS formulation can, for example, contain 30 mg DIM and 5-10 mg of melatonin per dose (e.g., capsule). A pharmaceutical SEDDS or SMEDDS formulation for use with melatonin as an additional API can be made using excipients as described for Formulation G (see Table 3 in the Examples). Accordingly, in some embodiments, melatonin is used in the compositions and formulations described herein in the amount from 2 mg to 12 mg, 2 mg to 10 mg, 2.5 mg to 10 mg, 4 mg to 10 mg, or 5 mg to 10 mg per dose (e.g., per capsule) (e.g., in the amount of 2.5 mg, 3 mg, 4 mg, 5 mg, 6 mg, 7 mg, 8 mg, 9 mg, 10 mg, or any other value in between). In such embodiments, a DIM-related indole, such as DIM, can be used in an amount from 20 mg to 65 mg, or from 25 mg to 50 mg per dose (e.g., per capsule) (e.g., in the amount of 20 mg, 25 mg, 30 mg, 35 mg, 40 mg, 45 mg, 50 mg, 65 mg, or any other value in between).

In other embodiments, the second API compatible with the DIM compositions described herein is Vitamin K (e.g, Phylloquinone [Vitamin K1], menaquinone [Vitamin K2], other forms of Vitamin K2 named menaquinone-4 [MK-4] or menaquinone-7 [MK-7], which is essential for liver support for clotting factors, circulatory health and bone health. All useful forms of Vitamin K have extremely low water solubility, requiring a lipid-based formulation technology for best bioavailability. Dose requirements for Vitamin K depend of the molecular type of Vitamin K to be utilized. The preferred forms for compositions of the invention comprising Vitamin K include Phylloquinone [Vitamin K1], and forms of Vitamin K2 including menaquinone-4 [MK-4] and menaquinone-7 [MK-7]. The dosage range for MK-4 is from 600-1500 ug per dose (e.g. capsule) and the dosage range for MK-7 is from 25-250 ug per dose (e.g. capsule) allowing for co-formulation with DIM compositions described herein. A preferred DIM/Vitamin K SEDDS or SMEDDS formulation comprises 25-30 mg of DIM and 25-200 ug of Vitamin K2 in the form of menaquinone-7 [MK-7]. In some embodiments, the DIM/Vitamin K2 SEDDS or SMEDDS formulation can also contain melatonin in the amount of 2.5 to 10 mg and/or Vitamin D in the amount of 1000-3000 IU per unit dose. In some embodiments, second API compatible with the DIM compositions described herein is Vitamin K2, and most preferably, Vitamin K in the form of menaquinone-7 [MK-7]. MK-7 can be combined with DIM in the pharmaceutical or nutritional formulations in a range of 25 micrograms to 250 micrograms of Vitamin MK-7 (e.g., menaquinone-7) per dose and 25-100 mg of DIM per dose (e.g., for a formulation to promote bone and heart health). The log P of menaquinone-4 is 10-12 and menoquine-7 is 17 (thus, both are dependent on lipid solubility and would be compatible with the compositions described herein, which is similar to retinyl palmitate in particular). Menaquinone-7 is available as an oil solution (M-1500 ppm) and as powder (P-1000, P-2000 ppm) (containing the menaquinone-7 form of natural vitamin K2), and it is available as 1 kg, 5 kg and 25 kg (see http://www.nattopharma.com/how-to-buy-menaq7.html). Accordingly, in some embodiments, Vitamin K (e.g., Vitamin K1 or Vitamin K2) is used in the compositions and formulations described herein in the amount from 150 mg to 275 mg, 170 mg to 260 mg, 175 mg to 250 mg, or 190 mg to 225 mg per dose (e.g., per capsule) (e.g., in the amount of 175 mg, 180 mg, 190 mg, 200 mg, 210 mg, 220 mg, 225 mg, 230 mg, 240 mg, 250 mg, or any other value in between). In such embodiments, a DIM-related indole, such as DIM, can be used in an amount from 20 mg and 125 mg, or from 25 mg to 100 mg per dose (e.g., per capsule) (e.g., in the amount of 25 mg, 30 mg, 40 mg, 50 mg, 60 mg, 70 mg, 75 mg, 80 mg, 90 mg, 100 mg, or any other value in between).

In other embodiments, the second API compatible with the DIM compositions described herein is biculatamide (Casodex). Bicultamide has log P of 4.94. Bicalutamide (Casodex, Cosudex, Calutide, Kalumid) is an oral nonsteroidal antiandrogen used in the treatment of prostate cancer and hirsutism. Biculatamide is formulated according the present invention in combination with DIM in doses of 10-50 mg of Biculatamide in combination with 25-50 mg of DIM or DIM-related indole per dose (e.g., capsule). Typical daily dose of bicalutamine will require use of 1-5 capsules per day.

In other embodiments, the second API compatible with the DIM compositions described herein is artemether. Artemether has log P of 3.48, and it is used as a drug to treat parasitic diseases, such as malaria. Artemether is formulated in combination with DIM in soft or hard gelatin capsule or in rectal suppositories. Typical formulations will include 20-40 mg Artemether combined with 20-75 mg DIM per capsule taken in sufficient quantity to provide 80 mg Artemether per dose (e.g., capsule), taken once, twice, or three times daily according to disease severity and physician order. In rectal suppositories 40-80 mg of Artemether is combined with 50-100 mg of DIM per suppository, used every 12-24 hrs.

In other embodiments, the second API compatible with the DIM compositions described herein is tamoxifen. Tamoxifen has log P of 6.35, and it is used as a drug to treat breast cancer. Preferably 10-20 mg of tamoxifen are combined with 50-75 mg DIM per dose (e.g., capsule) and taken orally to provide 10-20 mg of tamoxifen once daily.

In other embodiments, the second API compatible with the DIM compositions described herein is gefitinib (ZD1839), which is N-(3-chloro-4-fluoro-phenyl)-7-methoxy-6-(3-morpholin-4-ylpropoxy)quinazolin-4-amine. Gefitinib is an Epidermal Growth Factor Receptor (EGFR) inhibitor, which is used in the treatment of certain breast, lung and other cancers. Gefitinib is to be administered orally, and it has log P of 3.72. Preferably, 25-250 mg of gefitinib are combined with 50-75 mg DIM per dose (e.g., capsule) and taken orally in 2 to 10 doses (e.g., capsules) per day.

In other embodiments, the second API compatible with the DIM compositions described herein is lucitanib, which is 6-[7-[(1-aminocyclopropyl)methoxy]-6-methoxyquinolin-4-yl]oxy-N-methylnaphthalene-1-carboxamide. Lucitanib is a selective inhibitor of the tyrosine kinase activity of Fibroblast Growth Factor Receptor (FGFR types 1 and 2), Vascular Endothelial Growth Factor Receptor (VEGFR types 1-3), and Platelet Derived Growth Factor Receptor (PDGFR types α and β), and it is for use in cancer treatment. Lucitanib is to be administered orally, and it has log P of 3.81. Preferably, 5-15 mg of lucitanib are combined with 50-100 mg DIM per dose (e.g., capsule) and taken orally in 2 to 4 doses (e.g., capsules) per day.

20-50 mg of UA are combined with 30-75 mg DIM per dose (e.g., capsule) and taken orally to provide 40-400 mg of UA per day.

In other embodiments, a second API compatible with the DIM compositions described herein is selected from Retinoid-Related Receptor (ROR) inhibitors including, without limitation, natural products, particularly Plumbagin (5-hydroxy-2-methyl-1,4-naphthoquinone, PL), which is a natural bicyclic naphthoquinone found in the plants of Droseraceae, Plumbaginaceae, Ancistrocladaceae and Dioncophyllaceae families. Other natural product inhibitors of ROR that can be used in the compositions and formulations described herein include, without limitation, curcuminoids, particularly curcumin (diferuloylmethane) (see Sun et al., Curcumin inhibits imiquimod-induced psoriasis-like inflammation by inhibiting IL-1beta and IL-6 production in mice, PLoS One. 2013 Jun. 25; 8(6), the contents of which are incorporated by reference herein in their entirety) and including more active curcumin derivatives described in U.S. Patent Publication No. 20140303109 by Sarkar et al., the contents of which are incorporated by reference herein in their entirety. Other ROR Inhibitors that can be used in the compositions and formulations described herein include N-(5-(arylcarbonyl)thiazol-2-yl)amides in particular N-[5-(2-chloro-benzoyl)-4-(3-chlorophenyl)-thiazol-2-yl]-2-(4-ethanesulfonyl-phenyl)-acetamide (see Gege et al., Identification of the first inverse agonist of retinoid-related orphan receptor (ROR) with dual selectivity for RORβ and RORγt, Bioorg Med Chem Lett. 24(22):5265-7, the contents of which are incorporated by reference herein in their entirety). Further description of additional ROR inhibitors, that can be used in the compositions and formulations described herein, are described in U.S. Patent Publication No. 20150073016, the contents of which are incorporated by reference herein in their entirety. Additional ROR inhibitors, that can be used in the compositions and formulations described herein, are 2-oxo-1,2-dihydrobenzo[cd]indole-6-sulfonamide derivatives (see Zhang et al., 2014, Discovery of 2-oxo-1,2-dihydrobenzo[cd]indole-6-sulfonamide derivatives as new RORγ inhibitors using virtual screening, synthesis and biological evaluation. Eur J Med Chem. 78:431-41, the contents of which are incorporated by reference herein in their entirety). Further additional ROR inhibitors useful for inclusion in the present SMEDDS formulation as both single agents and in combination with DIM are described in U.S. Patent Publication Nos. 20120289495, 20130059883, and 20140256740 by Baloglu, Erkan et al., the contents of each of which are incorporated by reference herein in their entirety. Preferably 20-50 mg per dose (e.g., capsule) of the

| Generic Name of exemplary 2nd API drug | Trade Name of 2nd API drug (Source of drug) | Log P of $2^{nd}$ API drug | Dose Range of 2nd API drug per capsule (mg) | DIM Dose Range per capsule (mg) | Daily Dose of DIM and $2^{nd}$ API in number of Capsules |
|---|---|---|---|---|---|
| Gefitininb | Iressa (Astra Zeneca) | 3.72 | 25-250 | 50-75 | 2-10 |
| Lucitanib | None (Clovis Oncology) | 3.81 | 5-15 | 50-100 | 2-4 |

In other embodiments, the second API compatible with the DIM compositions described herein is Ursolic acid (UA; 3β-hydroxy-urs-12-en-28-oic acid), a poorly soluble, naturally derived pentacyclic triterpene acid that is widely present in food, medicinal herbs, and other plants. UA has a calculated Log P of 6.58 and is used to treat cancer, autoimmunity, and inflammatory skin conditions. Preferably compounds of Baloglu et al. are used alone or combined with 30-75 mg DIM per dose (e.g., capsule) and taken orally to provide 40-400 mg of the Baloglu et al. compound per day.

In certain embodiments, the one or more additional API compatible with the DIM compositions described herein has log P of more than 3.0. In certain embodiments, the one or more additional API compatible with the DIM compositions described herein has log P of less than 7. In the more preferred embodiments, the Log P of the one or more additional API is more than 3 and less than 7. In specific embodiments, the log P of the one or more additional API is between 3 and 5.5. In other embodiments, the log P of the one or more additional API is between 2 and 8.

5.7 Methods of Making of Compositions of the Invention

The methods of making self-emulsifying compositions described herein include steps necessary to dissolve a DIM-related indole in a mixture of selected excipients (e.g., in specific formula percentage amounts). As such, in certain embodiments, methods of making self-emulsifying compositions described herein comprise the following steps: (a) combining a solvent, a surfactant with an HLB greater than 7, and a co-surfactant with an HLB equal to or less than 7 (and, optionally, additional excipients described herein, such as PC and/or poloxamer) into a mixture, (b) warming and agitating the mixture to uniformity, (c) cooling the mixture (e.g., to approximately 50° C. or, to 40° C. to 60° C.) and adding an API, i.e., a DIM-related indole (e.g., DIM), and, optionally, one or more additional APIs, and (d) further agitating the mixture with the API(s) to uniformity. The mixture with a DIM-related indole and, optionally, another active agent, remaining in solution can then be added to a suitable dosage form, such as soft or hard-filled gelatin capsules, and allowed to further cool to ambient temperature.

The compositions described herein are SEDDS or SMEDDS compositions comprising a DIM-related indole, such as DIM, as an active agent. The methods of making SEDDS or SMEDDS compositions are known in the art. As such, the compositions described herein can be made using the general methodology known in the art.

The methods of making self-emulsifying compositions, formulations or drug delivery systems provided herein can include a step of solubilizing a DIM-related indole in a solvent, or in a mixture comprising a solvent, a surfactant with an HLB greater than 7, and a co-surfactant with an HLB equal to or less than 7.

The compositions and formulations described herein are not produced using spray drying methodology. The compositions and formulations described herein do not comprise an enteric coating (e.g., do not comprise a polymer-based enteric coating).

5.8 Chemical and Biological Properties of Select Compositions of the Invention In certain embodiments, the DIM-related indole has a very high degree of solubility in the carrier of the compositions described herein. In some embodiments, the DIM-related indole has at least or more than 80%, 85%, 90%, 95%, 97%, 98%, 99% solubility in the carrier. In some embodiments, the DIM-related indole has at least 95% or 100%, or from 95% to 100% solubility in the carrier. In certain embodiments, the DIM-related indole is dissolved in the carrier (i.e., displays at least 98% and up to 100% solubility in the carrier). In most preferred embodiments, the DIM-related indole is 100% dissolved in the carrier (i.e., displays 100% solubility in the carrier). In some embodiments, the DIM-related indole displays at least or more than 10% solubility in the solvent used in the compositions described herein (such as oil, lipid or another solvent, e.g., a diethylene glycol monoethyl ether or a caprylocaproyl polyoxyl-8 glyceride). In some embodiments, the DIM-related indole has at least or more than 12%, 13%, 14%, 15%, 16%, 17%, 18%, 19%, 20% or 25% solubility in the solvent (e.g., at least or more than 15% or 18% solubility in the solvent). In some embodiments, the DIM-related indole displays at least or more than 8%, 9%, 10%, 11%, 12%, 13%, 14%, or 15% solubility in the surfactant with HLB greater than 7 used in the compositions described herein. In some embodiments, the DIM-related indole displays at least or more than 5%, 6%, 7%, 8%, 9%, 10%, 12% or 15% solubility in the co-surfactant with HLB equal to or less than 7 used in the compositions described herein. In some embodiments, the DIM-related indole displays at least or more than 3%, 4% or 5% solubility in the triglyceride (or a derivative thereof) used in the compositions described herein. The solubility can be assessed by any method known in the art. For example, the solubility can be assessed by addition of solids until they would not go into the solution without giving cloudiness. In another example, the solubility can be assessed by adding API and then filtering the solids and determining how much API was in solution by dilution in solvent and concentration measurement by HPLC.

In specific embodiments, described herein are compositions and formulations that do not exhibit re-crystallization of the DIM-related indole (e.g., DIM) during storage, upon contact with intestinal fluid, upon ingestion by a subject or upon dispersion in water. In some embodiments, described herein are compositions and formulations that do not exhibit re-crystallization of the DIM-related indole upon ingestion by a subject. In some embodiments, described herein are compositions and formulations that do not exhibit re-crystallization of the DIM-related indole upon dispersion in intestinal fluids and/or water. In other specific embodiments, described herein are compositions and formulations that exhibit only minimal re-crystallization of the DIM-related indole (e.g., DIM) during storage, upon contact with intestinal fluid, upon ingestion by a subject or upon dispersion in water. In some embodiments, described herein are compositions and formulations that exhibit minimal re-crystallization of the DIM-related indole upon ingestion by a subject or upon dispersion in intestinal fluids or water. The minimal re-crystallization a DIM-related indole (e.g., DIM) can be re-crystallization of less than 25%, less than 20%, less than 15%, less than 10% or less than 5%.

In other specific embodiments, described herein are compositions and formulations that exhibit a reduced rate of re-crystallization of the DIM-related indole (e.g., DIM) during storage, upon contact with intestinal fluid, upon ingestion by a subject or upon dispersion in water. For example, the compositions described herein comprising an agent that inhibits re-crystallization (as any one or more of such agents described herein, e.g., a poloxomer or a triglyceride) can reduce the rate of re-crystallization of a DIM-related indole (e.g., DIM) upon contact with intestinal fluids or in an vitro dispersion test by more than 25%, more than 50%, more than 75%, or more than 90% as compared to the same compositions without such agent. In other embodiments, the compositions described herein comprising an agent that inhibits re-crystallization (as any one or more of such agents described herein, e.g., a poloxomaer or a triglyceride) can reduce the size of crystals produced during re-crystallization of a DIM-related indole (e.g., DIM) upon contact with intestinal fluids or in an vitro dispersion test by more than 25%, more than 50%, more than 75%, or more than 90% as compared to the same same composition without such agent. In other embodiments, the compositions described herein comprising an agent that inhibits re-crystallization (as any one or more of such agents described herein, e.g., a poloxomaer or a triglyceride) can reduce the size of crystals produced during re-crystallization of a DIM-related indole (e.g., DIM) upon contact with intestinal fluids or in an vitro dispersion test by more than 2 fold, 3 fold, 4 fold, 5 fold, 10 fold, 15 fold or 20 fold as compared to the same composition without such agent.

In some embodiments, the compositions described herein comprising an agent that inhibits re-crystallization (as any one or more of such agents described herein, e.g., a poloxomaer or a triglyceride) increase solubility of a DIM-related indole (e.g., DIM) upon contact with intestinal fluids or in an vitro lypolysis test by at least 1.5 fold, at least 2 fold or at least 3 fold, or by 25%, 50%, 100%, 200% or 300%, as compared to the same composition without such agent.

In certain embodiments, described herein are compositions and formulations that, upon dispersion in water or contact with intestinal fluid (e.g., upon ingestion by a subject), emulsify to form a dispersion of lipid-based globules (or yield an oil-in-water emulsion globules). In some embodiments, at least 50% of such globules are less than 1.5 µm, 1 µm, 0.75 µm, 0.5 µm or 0.3 µm in diameter. In some embodiments, at least 50% of such globules are less than 0.75 µm in diameter. In some embodiments, at least 50% of such globules are less than 0.4 µm in diameter. In some embodiments, at least 50% of such globules are less than 0.2 µm in diameter. In some embodiments, at least 50% of such globules are less than 0.1 µm in diameter. In some embodiments, at least 50% of such globules are between 0.05 and 1 µm, between 0.07 and 0.5 µm or between 0.05 and 0.2 µm in diameter. In some embodiments, such globules have a (surface weighted) mean particle diameter between 0.01 and 0.5 µm, between 0.01 and 0.4 µm, between 0.01 and 0.5 µm, between 0.01 and 1 µm between 0.05 and 1 µm, between 0.07 and 0.5 µm, between 0.09 and 0.3 µm, between 0.1 and 0.2 µm, or between 0.05 and 0.2 µm. In some embodiments, such globules have a mean particle diameter of less than 1.5 µm, 1 µm, 0.75 µm, 0.5 µm or 0.3 µm. In some embodiments, such globules have a mean particle diameter of less than 0.75 µm. In some embodiments, such globules have a mean particle diameter of less than 0.4 µm. In some embodiments, such globules have a mean particle diameter of less than 0.2 µm. In some embodiments, such globules have a mean particle diameter of less than 0.1 µm. Any values for mean particle size (diameter) in between the values described herein are also contemplated. The size of the globules or particles can be determined by any method known in the art or described herein. In one embodiment, the size of the globules or particles is determined by in vitro dispersion testing.

In certain embodiments, described herein are compositions and formulations that, 2 hours after ingestion by a subject, provide a DIM-related indole in a plasma of the subject in a concentration of at least or more than 150 ng/ml, 200 ng/ml, 250 ng/ml or 300 ng/ml, or between 200 ng/ml and 600 ng/ml, between 250 ng/ml and 500 ng/ml, or between 300 ng/ml and 400 ng/ml. In specific embodiments, described herein are compositions and formulations that, 2 hours after ingestion by a subject, provide a DIM-related indole in a plasma of the subject in a concentration of at least 200 ng/ml. In specific embodiments, described herein are compositions and formulations that, 2 hours after ingestion by a subject, provide a DIM-related indole in a plasma of the subject in a concentration of at least 250 ng/ml. In specific embodiments, described herein are compositions and formulations that, 2 hours after ingestion by a subject, provide a DIM-related indole in a plasma of the subject in a concentration of at least 300 ng/ml. In preferred embodiments, the subject is a human. In certain embodiments, described herein are compositions and formulations that, 2 hours after ingestion by a subject, provide a DIM-related indole in a plasma of the subject in a concentration of more than 100 ng/ml.

In certain embodiments, described herein are compositions and formulations that, upon ingestion by a subject, provide Cmax of a DIM-related indole of at least or more than 150 ng/ml, 200 ng/ml, 250 ng/ml or 300 ng/ml (in a plasma of a subject). In some embodiments, described herein are compositions and formulations that, upon ingestion by a subject, provide Cmax of a DIM-related indole of at least 200 ng/ml (in a plasma of a subject). In some embodiments, described herein are compositions and formulations that, upon ingestion by a subject, provide Cmax of a DIM-related indole of at least 250 ng/ml (in a plasma of a subject). In some embodiments, described herein are compositions and formulations that, upon ingestion by a subject, provide Cmax of a DIM-related indole of at least 300 ng/ml (in a plasma of a subject). In preferred embodiments, the subject is a human.

In certain embodiments, described herein are compositions and formulations that, upon ingestion by a subject, achieve mean or average AUC (ng/ml*hr) of the DIM-related indole of at least or more than 500 ng/ml*hr, 750 ng/ml*hr, 1000 ng/ml*hr, 1250 ng/ml*hr or 1500 ng/ml*hr, or between 750 ng/ml*hr and 2000 ng/ml*hr, or between 1000 ng/ml*hr and 2000 ng/ml*hr, or between 1250 and 1750 ng/ml*hr (in a plasma of a subject). In some embodiments, described herein are compositions and formulations that, upon ingestion by a subject, achieve mean or average AUC (ng/ml*hr) of the DIM-related indole of at least 750 ng/ml*hr (in a plasma of a subject). In some embodiments, described herein are compositions and formulations that, upon ingestion by a subject, achieve mean or average AUC (ng/ml*hr) of the DIM-related indole of at least 1000 ng/ml*hr (in a plasma of a subject). In some embodiments, described herein are compositions and formulations that, upon ingestion by a subject, achieve mean or average AUC (ng/ml*hr) of the DIM-related indole of at least 1250 ng/ml*hr (in a plasma of a subject). In preferred embodiments, the subject is a human.

5.9 Dosage, Formulations and Administration of the Compositions of the Invention The compositions provided herein may be administered by any oral and topical means and at any dosage, as described below. The actual administered amount of the compositions and formulations described herein may be decided by a supervising physician or veterinarian and may depend on multiple factors, such as, the age, condition, file history, etc., of the subject, or patient, in question.

In certain embodiments, a therapeutically effective amount of a DIM-related indole (e.g., DIM) is used in the compositions, kits and methods described herein. In some embodiments, a therapeutically effective amount of a DIM-related indole (e.g., DIM) and a therapeutically effective amount of a second API (e.g., retinoid, retinyl palmitate, Vitamin D, melatonin, Vitamin K, biculatamide, tamoxifen or artemether) is used in the compositions, kits and methods described herein. In some embodiments, a therapeutically effective amount is an amount that is effective to treat an impairment at a certain daily frequency of administration (e.g., once a day or twice a day). In some embodiments, where a combination of a DIM-related indole and a second API is used in the compositions, kits and methods described herein, the therapeutically effective amount of the second API is less than the therapeutically effective amount of such compound when it is used alone (i.e., without a DIM-related indole).

It will be appreciated that the amounts of the DIM-related indole and the second API described herein will vary according to the route of administration, the disorder to be treated, the condition, age, and file history of the subject, the galenic formulation of the composition, etc.

In certain embodiments, the compositions described herein are adapted for oral delivery. Such compositions can be filled into, e.g., hard gelatin capsules or soft gelatin capsules, for oral administration.

In specific embodiments, a DIM-related indole and a second API are administered in the a fixed dosage combination in the composition of the invention. For example, a DIM-related indole and a second API can be formulated in a capsule, such as one soft shell gelatin capsule or one hard shell gelatin capsule.

In other embodiments, a DIM-related indole and a second API are administered in separate compositions (i.e., co-administered without co-formulation), with the DIM-related indole administered in one of the compositions of the invention and the second API administered separately in any composition known in the art or described herein. In such compositions, one of the compositions of the invention (with a DIM-related indole as a biologically active agent) and a composition comprising a second biologically active agent can be administered to a patient concomitantly or sequentially. For example, these compositions can be administered at the same time, or within a certain number of minutes or hours of each other (e.g., 30 minutes, 1 hour, 1.5 hours, 2 hours, 3 hours, 4 hours, 5 hours, 6 hours, 7 hours, 8 hours, 9 hours, 10 hours, 11 hours, 12 hours, 18 hours or 24 hours).

In certain embodiments, the compositions of the invention comprise 10 to 200 mg, 20 to 150 mg or 25 to 100 mg of a DIM-related indole (e.g., DIM) per dose (formulated, for example, for oral administration, e.g., in a gel capsule). The compositions of the invention may be administered once per day, or two or more times per day. Preferably the compositions formulated for administration, e.g., capsules, comprise from 25 mg to 100 mg of a DIM-related indole (e.g., DIM), which is administered one or two times per day. In particular embodiments, A DIM-related indole, such as DIM, is in an amount from 25 to 100 mg per dose in the compositions and formulations provided herein (when used either as the only biologically active agent or together with one or more additional biologically active agents in the compositions and formulations described herein). In specific embodiments, the compositions described herein are formulated as capsules which comprise 25 mg, 50 mg or 75 mg of DIM. In one embodiment, the compositions described herein are formulated as capsules comprising 25 to 75 mg of DIM, and are administered to a subject orally twice per day.

In specific embodiments, when a second API is included in the compositions of the invention, the second API is used in an amount less than the amount of DIM in the compositions (per dose of the composition). In some embodiments, the total amount of active agent(s) in a dose of the composition or formulation is 50 to 150 mg, e.g., 75 mg, 80 mg, 90 mg, 100 mg, 110 mg, 120 mg, 125 mg, 130 mg, or 140 mg or 150 mg. In particular embodiments, the total amount of active agent(s) in a dose of the composition or formulation is 100 to 140 mg, e.g., 120 mg. For example, some compositions and formulations provided herein comprise one of the above-referenced amounts of a DIM-related indole (when it is used as an only active agent). In the compositions and formulations described herein comprising one or more APIs in addition to a DIM-related indole, the amount of a DIM-related indole can be reduced to accommodate an additional API (for example, 90 mg to 110 mg, e.g., 100 mg, of a DIM-related indole can be combined with 10 mg to 30 mg, e.g., 20 mg, of a second API).

Co-administration or co-formulation of a DIM-related compound with a second API may be effective to reduce the dose of the DIM-related indole to be administered to a subject. Alternatively, or in addition, co-administration or co-formulation of a DIM-related compound with a second API may be effective to reduce the dose of the second API to be administered to a subject. In one embodiment, effective dose of a DIM-related indole would be the same as used when DIM is administered alone.

Regarding periods of treatment, a subject can be treated with the compositions of the invention (with or without the second API) for 1 week, 2 weeks, 3 weeks, 4 weeks, 5 weeks, 6 weeks, 7 weeks, 8 weeks, 9 weeks, 10 weeks, 3 months, 4 months, 5 months, 6 months, 7 months, 8 months, 9 months, 10 months, 11 months, 1 year, 1.5 years, 2 years, 3 years, 4 years, 5 years or more than 5 years. In certain embodiments, the subject is treated with the compositions of the invention for more than: 1 month, 2 months, 3 months, 4 months, 5 months, 6 months, 7 months, 8 months, 9 months, 10 months, 11 months, 1 year, 1.5 years, 2 years, 3 years, 4 years, 5 years, or more than 5 years. In certain embodiments, the compositions described herein achieve efficacy (which can be manifested in improvement or stabilization of one or more parameters or symptoms of the disease) in less than: 2 weeks, 3 weeks, 1 month, 2 months, 3 months, 4 months, 5 months, 6 months, 7 months, 8 months, 9 months, 10 months, 11 months, or 1 year. In specific embodiments, the compositions described herein achieve efficacy (which can be manifested in improvement or stabilization of one or more parameters or symptoms of the disease) in less than 1 month or less than 3 months.

As described above, the compositions of the invention can be filled into gel capsules (e.g., hard gelatin capsules or soft gelatin capsules), for oral administration. In production, hard gelatin capsules can be filled with the use of a liquid fill system that is set to dispense the warmed liquid formulation into hard gelatin capsules. When hand-filling capsules, the use of a hand filling template apparatus is advised. Here, the capsules are simply separated with the lower larger part placed in the holes of the template. A measured amount of liquid is filled into each capsule with a syringe. The top cap is placed on to each lower half and with the apparatus the top capsules are snapped into place. The capsules are removed from the apparatus, ready for packaging.

For soft gelatin capsules, the warmed liquid is pumped into the capsule-making equipment. A separate tank of warm gelatin solution is metered to the equipment. A ribbon of gelatin is fed to each side of the capsule filler to fill molds which form each half of the shell. The filler meters the formulation as the two halves are fused together in the equipment. The soft capsules are dried before going to the packaging station.

In other embodiments, the compositions described herein are adapted for topical delivery to selected mucosal surfaces through dilution of the compositions described herein with a selected volatile Class III solvent or solvent combination, distribution of the diluted composition on the surface of the delivery device, followed by evaporation of the solvent.

The dosage forms of the present invention are modified with the addition of a compatible Class III solvent to the compositions described herein to produce a uniform diluted formulation providing for metered dose topical delivery of the self-emulsifying compositions of the invention. Solvent diluted formulations are then applied to delivery vehicles such as, for example, to dry feminine tampons. Following dipping of the delivery vehicle (e.g., an absorbent tampon) into the solvent diluted formulation, the delivery vehicle (e.g., a tampon) is dried in conditions sufficient to evaporate the solvent. This allows the DIM SEDDS or SMEDDS to re-concentrate as an evenly distributed lipid based formulation. When utilized as a medicated delivery vehicle (e.g., a tampon) the DIM SEDDS or SMEDDS formulation emulsifies in the use environment releasing mg amounts of DIM in consistent amounts within desired dose ranges.

The formulations described herein encompass addition of a selected Class III solvent up to a final solvent: SEDDS/SMEDDS composition ratio of not more than 9:1 on a wt/wt basis. Preferred DIM composition described herein that can be solvent diluted for topical delivery include compositions similar to or the same as Formulations K or L described in the Examples section (see Table 3). Preferred solvents for dilution include, without limitation, ethanol, isopropanol, and acetone. Most preferred solvent for such dilution is isopropanol. Application of DIM SEDDS or SEDDS compositions to delivery devices, such as tampons, optionally utilize steps for large scale manufacture described in detail in U.S. patent Publication No. 11/0288501 by Gehling et al., the contents of which are incorporated by reference herein in their entirety.

Some of the nutritional compositions of the present invention are described in Table 4. For example, Formulations K or L can be adapted through solvent dilution to application by spray nozzle onto food items for human use or veterinarian use (e.g., for companion animals). Formulation R can also be adapted through solvent dilution to application by spray nozzle onto food items for human use or veterinarian use (e.g., for companion animals). Following spray application of a metered dose of the solvent-diluted compositions described herein, the food items are dried to remove volatile solvent and packaged to preserve DIM activity. For example, this methodology can be used to produce dog, cat, horse or other companion animal food items such as "treats" or biscuits containing an appropriate unit dose of DIM per kg of the animal. This methodology can also be used to produce nutritional health bar products for human use.

In a preferred embodiment, formulations described herein, e.g., Formulation R, are utilized in producing veterinary supplements (e.g., supplements for dogs and cats). Such supplements can be produced through dispersion of unit doses of the formulation into weighed quantities of mixtures of additional ingredients. Additional ingredients may include, for example, powdered brewer's yeast and chicken, beef, or salmon flavors. Additional excipients standard to the industry can be added to produce tablets including, without limitation, flavoring, sweeteners, binders, flow agents, bulk forming agents, and tablet lubricants. The mixture of ingredients can be formed into chewable tablets using standard tablet pressing equipment. A typical unit dose of DIM in such a chewable tablet would be 25-100 mg per 2-10 gram tablet. Typical use would include offering the chewable tablet to a companion animal such as a dog or cat suffering from atopic dermatitis once or twice daily. Effective use includes providing 1-5 mg per kg weight of companion animal per dose.

In a further preferred embodiment, formulations described herein, e.g., Formulation R, are utilized in producing a veterinary chewable "treat" for companion animals such as dogs and cats. Treats can be produced by dispersion of unit doses of the formulation into weighed quantities of mixtures of additional ingredients. Additional ingredients may include, for example, powdered brewer's yeast and chicken, beef, or salmon flavors. Additional excipients standard to the industry can be added to produce treats including, without limitation, flavoring, sweeteners, binders, flow agents, and bulk forming agents. The mixture can be formed into chewable treats using standard equipment. The mixture of ingredients can be formed into chewable treats, consisting of 5-20 grams of material, using standard mixing, unit forming, and baking techniques. A typical unit dose of DIM in such a treat would be 25-100 mg per 5-20 gram treat. Typical use would include offering the treat to a companion animal such as a dog or cat suffering from atopic dermatitis once or twice daily. In preferred embodiments, the additional ingredients standard to the industry include powdered brewer's yeast, flax seed powder, and optionally, green lipped muscle powder, *Curcuma longa* powder or *Yucca schidigera* powder with additional chicken, beef, or salmon flavors.

In certain embodiments, it is contemplated that the compositions described herein can be used in personal hygiene products such as face wash or face scrub formulations, for topical application. In particular, such formulations and applications are contemplated for uses in the treatment and prevention of skin conditions, such as dandruff, acne and rosacea (e.g., acne). In some embodiments, such face washes or face scrubs comprise a DIM-related indole (e.g., DIM or LTR) and a retinoid (e.g., retinyl palmitate). In certain embodiments, it is contemplated that the compositions described herein can be used in personal hygiene products such as shampoos (e.g., for treating dandruff). In a preferred embodiment, a DIM-related indole (e.g., DIM or LTR) is combined with the dry distillation tar of delipidated soybean (Glyteer, Fuginaga Pharm, Tokyo, Japan), along with excipients standard to the industry to produce shampoos and facial "scrubs". Delipidated soybean tar can be utilized in concentrations of 1-7% by weight in such formulations, and such formulations can be utilized in personal hygiene once or twice daily.

Related uses and delivery vehicles, allowing for self-emulsification of the formulations following topical application to the watery environment of wet mucosal surfaces, is also contemplated herein.

5.10 Methods of Treatment and Uses of the Compositions of the Invention

The compositions and formulations provided herein can be used in the treatment or prevention of any disease, disorder or condition for which the DIM-related indoles described herein and/or the additional active agents described herein are known to be beneficial (e.g., are known to have a therapeutic or preventative effect). In certain embodiments, the compositions and formulations provided herein are used in the treatment or prevention of any disease, disorder or condition described herein or known in the art as a disease, disorder or condition that can be treated or prevented using a DIM-related indole (e.g., crystalline DIM or BR-DIM). In certain embodiments, the compositions and formulations provided herein are used to promote health (e.g., heart health, bone health, skin health, etc.) as described herein or known in the art. Encompassed herein are methods of treatment or prevention of a disease, disorder or condition comprising administering any one of the compositions and formulations provided herein to a subject (e.g., a human). The administration can be oral administration (e.g., in a form of a capsule, such as a soft shell capsule or a hard shell capsule). In other embodiments, the administration can be topical administration (using any of the methods of topical administration described herein and any of the delivery vehicles described herein). The compositions and formulations provided herein can be administered once daily or twice daily. In one embodiment, the compositions and formulations provided herein are administered once daily. In one embodiment, the compositions and formulations provided herein are administered twice daily. In preferred embodiments, a therapeutically effective amount of the biologically active agent is administered (e.g., a therapeutically effective amount of a DIM-related indole such as DIM). In some embodiments, the DIM-related indole is administered as the only active agent. In other embodiments, two or more active agents (including a DIM-related indole are administered). In specific embodiments, two or more active agents are administered in the same composition (such as any of the compositions described herein), in a fixed dose combination. In other specific embodiments, two or more active agents are administered in separate compositions (e.g., a DIM-related indole is administered in any of the compositions described herein and an additional active agent is administered in a separate composition), such administration can be concomitant or sequential.

In particular, encompassed herein are methods of treatment of dandruff, acne or rosacea in a subject comprising administering any one of the compositions and formulations provided herein to a subject (e.g., a human). In some embodiments, the subject being treated has acne (e.g., has been diagnosed with acne). Also encompassed herein are methods of prevention of acne in a subject comprising administering any one of the compositions and formulations provided herein to a subject (e.g., a human). In some embodiments, provided herein are methods for treating (or preventing) acne in a subject in need thereof comprising administering (e.g., orally or topically) a composition provided herein, wherein the composition comprises a DIM-related indole and an additional active agent known to be effective in the treatment (or prevention) of acne. In some of the preferred embodiments, provided herein are methods for treating (or preventing) acne in a subject in need thereof comprising administering a composition provided herein, wherein the composition comprises a DIM-related indole, a retinoid, e.g., retinyl palmitate (as an additional active agent), and optionally, further comprises Vitamin D. In certain embodiments, provided herein are methods for treating acne in a patient in need thereof comprising orally administering a composition provided herein, wherein the composition further comprises a retinoid, e.g., retinyl palmitate (as an additional active agent). In certain embodiments, provided herein are methods for treating acne in a patient in need thereof comprising orally administering a composition provided herein, wherein the composition further comprises Vitamin D (as an additional active agent). In certain embodiments, provided herein are methods for treating acne in a patient in need thereof comprising orally administering a composition provided herein, wherein the composition further comprises a retinoid, e.g., retinyl palmitate, and Vitamin D (as additional active agents). In such embodiments, it is contemplated that the DIM-related indole and the one or more additional active agents (such as retinyl palmitate and/or Vitamin D) are present in the same composition, in a fixed dose combination (such as in one capsule). Retinyl palmitate can be in an amount from 2.75 mg to 13.75 mg (5,000 to 25,000 IU) or from 2.75 to 10 mg per dose (in the compositions administered to a subject). The DIM-related indole (e.g., DIM) can be in an amount from 25 to 100 mg per dose (in the compositions administered to a subject). In other embodiments, the compositions administered to a subject to treat acne comprise a DIM-related indole as the only biologically active agent. In some of these embodiments, concurrent administration of an additional active agent (e.g., a retinoid such as retinyl palmitate and/or Vitamin D), in a separate container or composition, is also contemplated. In some embodiments, provided herein are methods for treating acne in a subject in need thereof comprising administering (e.g., orally) a composition provided herein, and co-administering (e.g., orally) a retinoid, e.g., retinyl palmitate and/or Vitamin D to a subject (such administration can be concomitant or sequential). In one embodiment, both a composition comprising a DIM-related indole and a retinoid, such as retinyl palmitate, and/or Vitamin D are administered orally. In particular embodiments of the methods provided herein, the compositions described herein (comprising a DIM-related indole as the only active agent, or comprising one or more active agents such as a retinoid, e.g., Retinyl Palmitate, and/or Vitamin D in addition to a DIM-related indole) are effective to treat acne (e.g., when administered for a period of at least 1 month, 2 months, 3 months, 4 months, 5 months or 6 months). In a specific embodiment, the compositions described herein (comprising a DIM-related indole as the only active agent, or comprising one or more active agents such as Retinyl Palmitate and/or Vitamin D in addition to a DIM-related indole) are effective to treat acne when administered for a period of at least 3 months or at least 6 months. In one embodiment, the administering as described herein is performed once daily. In one embodiment, the administering as described herein is performed twice daily. The administering can also performed topically in a suitable delivery vehicle (e.g., in a form of a topical delivery vehicle such as a face wash or a face scrub).

Also encompassed herein are methods for promoting sleep, reducing sleep latency (i.e., shortening time to fall asleep), improving sleep quality (i.e., achieving more consistent progression through sleep stages), or reducing the number of night-time awakenings in a subject in need thereof comprising administering any one of the compositions and formulations provided herein to a subject (e.g., a human). In some embodiments, the subject being treated has insomnia, prolonged sleep latency or suffers from frequent night-time awakenings (e.g., has been diagnosed with such one or more of such conditions). In some embodiments, provided herein are methods for promoting sleep, reducing sleep latency, improving sleep quality, or reducing the number of night-time awakenings in a subject in need thereof comprising administering (e.g., orally) a composition provided herein, wherein the composition comprises a DIM-related indole and one or more additional active agents known to promote sleep, reduce sleep latency or reduce the number of night-time awakenings. In some of the preferred embodiments, provided herein are methods for promoting sleep, reducing sleep latency or reducing the number of night-time awakenings in a subject in need thereof comprising administering (e.g., orally) a composition provided herein, wherein the composition comprises a DIM-related indole and melatonin (as an additional active agent). In such embodiments, it is contemplated that the DIM-related indole and the one or more additional active agents (such as melatonin) are present in the same composition, in a fixed dose combination (such as in one capsule). The DIM-related indole (e.g., DIM) can be in an amount from 25 to 100 mg per dose (in the compositions administered to a subject). In other embodiments, the compositions administered to a subject to promote sleep, reduce sleep latency or reduce the number of night-time awakenings comprise a DIM-related indole as the only biologically active agent. In some of these embodiments, concurrent administration of an additional active agent (e.g., melatonin), in a separate container or composition, is also contemplated. In some embodiments, provided herein are methods for promoting sleep, reducing sleep latency or reducing the number of night-time awakenings in a patient in need thereof comprising administering (e.g., orally) a composition provided herein, and co-administering (e.g., orally) melatonin to a subject (such administration can be concomitant or sequential). In one embodiment, both a composition comprising a DIM-related indole and melatonin are administered orally. In particular embodiments of the methods provided herein, the compositions described herein (comprising a DIM-related indole as the only active agent, or comprising one or more active agents such as melatonin in addition to a DIM-related indole) are effective to promote sleep, reduce sleep latency or reduce the number of night-time awakenings (e.g., when administered for a period of at least 1 month, 2 months, 3 months, 4 months, 5 months or 6 months). In one embodiment, provided herein are methods for promoting sleep described herein. In one embodiment, provided herein are methods for reducing sleep latency described herein. In one embodiment, provided herein are methods for reducing the number of night-time awakenings described herein. In one embodiment, the administering as described herein is performed once daily. In one embodiment, the administering as described herein is performed twice daily.

Also encompassed herein are methods for promoting bone health or promoting heart health in a subject in need thereof comprising administering any one of the compositions and formulations provided herein to a subject (e.g., a human). In some embodiments, the subject being treated has a bone health-associated disease or disorder (e.g., osteoporosis), for example, the subject has been diagnosed with a bone health disease or disorder. In some embodiments, the subject being treated has a cardiovascular disease or disorder, or a heart disease or disorder, for example, the subject has been diagnosed with such a disease or disorder.

In some embodiments, the methods provided herein promote skin health such as methods for treating dandruff, acne vulgaris, rosacea, atopic dermatitis, and psoriasis (e.g., resulting in the improvement and/or resolution of such conditions). In further embodiments, provided herein are methods for using the compositions and formulations described herein for treating Endometriosis, Uterine or Extrauterine Myomas, or Protozoal Parasitic infections in accordance with (e.g., using the methods of administration described in, treating the patient populations described in) U.S. Pat. Nos. 6,689,387, 7,384,971, 7,384,972, 8,080,577, 8,586,621, the contents of each of which are incorporated by reference herein in their entireties. In further embodiments, provided herein are methods for treating certain autoimmune disorders including multiple sclerosis, rheumatoid arthritis, psoriasis, Crohn's disease, inflammatory bowel disease, graft-versus-host disease (GVHD), Sjorgen's syndrome, Guillain-Barre syndrome, psoriatic arthritis, Graves' disease, allergic contact dermatitis, systemic lupus erythematosus (SLE), cutaneous lupus erythematosus, ankylosing spondylitis, and Hashimoto Thyroiditis, (e.g., wherein the subject being treated has been diagnosed with such a disease or condition). In further embodiments, provided herein are methods for treating certain rare, Orphan Diseases including Behcets disease and Recurrent Respiratory Papillomatosis (RRP) (e.g., wherein the subject being treated has been diagnosed with such a disease or condition). Any of the compositions and formulations described herein can be used in these methods. Such methods comprise administering any of the compositions or formulations described herein to a subject (e.g., a human), for example, orally (e.g., in a form of a capsule) or topically (e.g., in a form of one of the delivery vehicles described herein).

In a specific embodiment, the compositions and formlations described herein are used in the treatment or prevention of atopic dermatitis in a subject (such as a mammal, e.g., a human, a dog or a cat). In one embodiment, provided herein is a method of treating atopic dermatitis in a subject comprising administering a composition or a formulation described herein to the subject (wherein the subject can be a human or a companion animal, and wherein the composition or formulation is a self-emulsifying DIM composition or formulation described herein, which can be used either alone or in combination with one or more additional active ingredients). In one preferred embodiment, Formulation R described herein (or a formulation similar or substantially the same as Formulation R, e.g., a formulation having the same or equivalent components or components having the same HLB as Formulation R, and wherein such components are in the same, substantially the same or about the same amount by weight as in Formulation R) is used in the treatment or prevention of atopic dermatitis (Formulation R is described in Examples 18 and 19). In one preferred embodiment, Formulation G described herein (or a formulation similar or substantially the same as Formulation G, e.g., a formulation having the same or equivalent components or components having the same HLB as Formulation G, and wherein such components are in the same, substantially the same or about the same amount by weight as in Formulation G) is used in the treatment or prevention of atopic dermatitis (Formulation G is described in Example 7 and Table 3). Generally, the term "about" as used herein encompasses a range of values between 25% greater than and 25% less than the stated value; in one embodiment, the term "about" encompasses a range of values between 10% greater than and 10% less than the stated value.

In some embodiments, provided herein are methods for promoting bone health or promoting cardiovascular or heart health or skin health in a subject in need thereof comprising administering (e.g., orally) a composition provided herein, wherein the composition comprises a DIM-related indole and one or more additional active agents known to promote bone health, promote cardiovascular health, or promote heart health. In some of the preferred embodiments, provided herein are methods for promoting bone health or promoting cardiovascular or heart health in a subject in need thereof comprising administering (e.g., orally) a composition provided herein, wherein the composition comprises a DIM-related indole and Vitamin K (as an additional active agent). In such embodiments, it is contemplated that the DIM-related indole and the one or more additional active agents (such as Vitamin K) are present in the same composition, in a fixed dose combination (such as in one capsule). The DIM-related indole (e.g., DIM) can be in an amount from 25 to 100 mg, and Vitamin K can be in an amount from 175 mg to 250 mg (per dose of the compositions administered to a subject, e.g., per capsule). In other embodiments, the compositions administered to a subject to promote bone, cardiovascular or heart health comprise a DIM-related indole as the only biologically active agent. In some of these embodiments, concurrent administration of an additional active agent (e.g., Vitamin K), in a separate container or composition, is also contemplated. In some embodiments, provided herein are methods for promoting bone, cardiovascular or heart health in a patient in need thereof comprising administering (e.g., orally) a composition provided herein, and co-administering (e.g., orally) Vitamin K to a subject (such administration can be concomitant or sequential). In one embodiment, both a composition comprising a DIM-related indole and Vitamin K are administered orally. In particular embodiments of the methods provided herein, the compositions described herein (comprising a DIM-related indole as the only active agent, or comprising one or more active agents such as Vitamin K in addition to a DIM-related indole) are effective to promote bone health or promote cardiovascular or heart health (e.g., when administered for a period of at least 1 month, 2 months, 3 months, 4 months, 5 months or 6 months). In one embodiment, provided herein are methods for promoting bone health (e.g., for treating or preventing osteoporosis) described herein. In one embodiment, provided herein are methods for promoting cardiovascular or heart health described herein. In one embodiment, provided herein are methods for promoting heart health described herein. In one embodiment, the administering as described herein is performed once daily. In one embodiment, the administering as described herein is performed twice daily.

Also encompassed herein are methods for treating or preventing prostate cancer in a subject in need thereof comprising administering any of the compositions and formulations provided herein to a subject (e.g., a human). In certain embodiments, the subject being treated has prostate cancer (has been diagnosed with prostate cancer). In some embodiments, provided herein are methods for treating prostate cancer in a subject in need thereof comprising administering (e.g., orally) a composition provided herein, wherein the composition comprises a DIM-related indole and one or more additional active agents known to treat prostate cancer. In some of the preferred embodiments, provided herein are methods for treating prostate cancer in a subject in need thereof comprising administering (e.g., orally) a composition provided herein, wherein the composition comprises a DIM-related indole and Biculatamide (as an additional active agent). In such embodiments, it is contemplated that the DIM-related indole and the one or more additional active agents (such as Biculatamide) are present in the same composition, in a fixed dose combination (such as in one capsule). In other embodiments, the compositions administered to treat prostate cancer comprise a DIM-related indole as the only biologically active agent. In some of these embodiments, concurrent administration of an additional active agent (e.g., Biculatamide), in a separate container or composition, is also contemplated. In some embodiments, provided herein are methods for treating prostate cancer in a patient in need thereof comprising administering (e.g., orally) a composition provided herein, and co-administering (e.g., orally) Biculatamide to a subject (such administration can be concomitant or sequential). In one embodiment, both a composition comprising a DIM-related indole and Biculatamide are administered orally. In particular embodiments of the methods provided herein, the compositions described herein (comprising a DIM-related indole as the only active agent, or comprising one or more active agents such as Biculatamide in addition to a DIM-related indole) are effective in treating prostate cancer or one or more symptoms of prostate cancer (e.g., in reducing the size of the tumor, slowing progression of the tumor, prolonging the life span, increasing remission time, etc.). In one embodiment, the administering as described herein is performed once daily. In one embodiment, the administering as described herein is performed twice daily.

Also encompassed herein are methods for treating or preventing breast cancer in a subject in need thereof comprising administering any one of the compositions and formulations provided herein to a subject (e.g., a human). In certain embodiments, the subject being treated has breast cancer (has been diagnosed with breast cancer). In some embodiments, provided herein are methods for treating breast cancer in a subject in need thereof comprising administering (e.g., orally) a composition provided herein, wherein the composition comprises a DIM-related indole and one or more additional active agents known to treat breast cancer. In some of the preferred embodiments, provided herein are methods for treating breast cancer in a subject in need thereof comprising administering (e.g., orally) a composition provided herein, wherein the composition comprises a DIM-related indole and tamoxifen (as an additional active agent). In such embodiments, it is contemplated that the DIM-related indole and the one or more additional active agents (such as tamoxifen) are present in the same composition, in a fixed dose combination (such as in one capsule). In other embodiments, the compositions administered to treat breast cancer comprise a DIM-related indole as the only biologically active agent. In some of these embodiments, concurrent administration of an additional active agent (e.g., tamoxifen), in a separate container or composition, is also contemplated. In some embodiments, provided herein are methods for treating breast cancer in a patient in need thereof comprising administering (e.g., orally) a composition provided herein, and co-administering (e.g., orally) tamoxifen to a subject (such administration can be concomitant or sequential). In one embodiment, both a composition comprising a DIM-related indole and tamoxifen are administered orally. In particular embodiments of the methods provided herein, the compositions described herein (comprising a DIM-related indole as the only active agent, or comprising one or more active agents such as tamoxifen in addition to a DIM-related indole) are effective in treating breast cancer or one or more symptoms of breast cancer (e.g., in reducing the size of the tumor, slowing progression of the tumor, prolonging the life span, increasing remission time, etc.). In one embodiment, the administering as described herein is performed once daily. In one embodiment, the administering as described herein is performed twice daily.

Also encompassed herein are methods for treating or preventing a parasitic disease (e.g., malaria) in a subject in need thereof comprising administering any one of the compositions and formulations provided herein to a subject (e.g., a human). In certain embodiments, the subject being treated has a parasitic disease such as malaria (e.g., has been diagnosed with a parasitic disease such as malaria). In some embodiments, provided herein are methods for treating a parasitic disease, such as malaria, in a subject in need thereof comprising administering (e.g., orally or rectally) a composition provided herein, wherein the composition comprises a DIM-related indole and one or more additional active agents known to treat the parasitic disease (e.g., malaria). In some of the preferred embodiments, provided herein are methods for treating a parasitic disease (e.g., malaria) in a subject in need thereof comprising administering (e.g., orally or rectally) a composition provided herein, wherein the composition comprises a DIM-related indole and Artemether (as an additional active agent). In such embodiments, it is contemplated that the DIM-related indole and the one or more additional active agents (such as Artemether) are present in the same composition, in a fixed dose combination (such as in one capsule, or one rectal suppository as a delivery vehicle). In other embodiments, the compositions administered to treat a parasitic disease (e.g., malaria) comprise a DIM-related indole as the only biologically active agent. In some of these embodiments, concurrent administration of an additional active agent (e.g., Artemether), in a separate container or composition, is also contemplated. In some embodiments, provided herein are methods for treating a parasitic disease (e.g., malaria) in a patient in need thereof comprising administering (e.g., orally or in a form a rectal suppository) a composition provided herein, and co-administering (e.g., orally or in a form a rectal suppository) Artemether to a subject (such administration can be concomitant or sequential). In one embodiment, both a composition comprising a DIM-related indole and Artemether are administered orally. In particular embodiments of the methods provided herein, the compositions described herein (comprising a DIM-related indole as the only active agent, or comprising one or more active agents such as Artemether in addition to a DIM-related indole) are effective in treating a parasitic disease (e.g., malaria) or one or more symptoms thereof (e.g., effective to reduce parasite counts, such as blood, tissue or intestinal parasite counts). In one embodiment, the administering as described herein is performed once daily. In one embodiment, the administering as described herein is performed twice daily.

5.11 Patient Identification or Selection

The subject, or patient, to be treated using the methods of the invention is an animal, e.g., a mammal, e.g., a human, a cow, a dog, a cat, a goat, a horse, a sheep or a pig, In a preferred embodiment, the patient is a human, and can be a fetus, child, or adult. In one embodiment, the subject is a human male. In another embodiment, the subject is a human female.

In certain embodiment, the subject has (e.g., has been diagnosed with) the disease, disorder or condition being treated.

5.12 Kits

The invention also provides a pharmaceutical, nutritional or nutraceutical pack or kit comprising one or more containers, wherein at least one container is filled with one or more compositions of the invention. A pack can be a blister pack (e.g., carrying capsules), a pack of tampons, a pack of rectal suppositories, a pack of wound dressings, or a pack of nutritional products (a pack of food bars or drink mixes). Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, the kit comprises in one container a composition of the invention comprising a DIM-related indole and a second API (in the same delivery vehicle). In one embodiment, the composition of the invention comprises a DIM-related indole and a second API together in one capsule (e.g., in a blister pack). The kit may comprise multiple dosage units such as capsules. In other embodiments, the composition of the invention comprising a DIM-related indole is provided in one container, and a second API is in a separate container of the kit.

In specific embodiments, the kit comprises one of the compositions of the invention formulated for oral administration. In other embodiments, the kit comprises one of the compositions of the invention formulated for topical administration (in an appropriate delivery vehicle).

The kit can comprise any dosage of a DIM-related indole and a second API described herein. In a specific embodiment, the DIM-related indole is DIM.

In certain embodiments, the kit can comprise one or more containers, utensils and/or instructions. A utensil can comprise item(s) to administer the drug. A container can contain one or multiple doses of the composition of the invention (e.g., multiple doses in single dose units). The kit may further contain instructions for administration of the compounds of the invention, e.g., instructions regarding dosages, frequency of administration, indications, mode of administration, counter-indications, etc. For example, the instructions may indicate that the composition is to be taken once daily or twice daily.

5.13 Exemplary Embodiments of the Invention

Embodiment 1

A composition comprising a DIM-related indole having Log P from 3 to 5.5 and a carrier, wherein the carrier comprises a carrier solvent, one or more surfactants with an HLB of greater than 7, and one or more co-surfactants with HLB equal to or less than 7.

Embodiment 1 (Alternatively Phrased)

A self-emulsifying composition (or formulation) for delivery of a DIM-related indole comprising a DIM-related indole having Log P from 3 to 5.5 and a carrier (of the DIM-related indole), wherein the carrier comprises a carrier solvent, one or more surfactants with an HLB of greater than 7, and one or more co-surfactants with HLB equal to or less than 7.

Embodiment 2

The composition of embodiment 1, wherein the carrier is a solution or a suspension.

Embodiment 3

The composition of embodiment 1 or 2, wherein the DIM-related indole is dissolved in the carrier, or wherein the DIM-related indole has more than 10% solubility in the solvent.

Embodiment 4

The composition of any one of embodiments 1 to 3, wherein the one or more co-surfactants with HLB equal to or less than 7 comprise a lecithin. Optionally, in some embodiments, the lecithin is in an amount of at least 4%, in specific embodiments, between 4% and 15%.

Embodiment 5

The composition of embodiment 4, wherein the lecithin is phosphatidyl choline or lysophosphatidyl choline.

Embodiment 6

The composition of embodiment 5, wherein the lecithin is phosphatidyl choline.

Embodiment 7

The composition of any one of embodiments 1 to 6, wherein the one or more co-surfactants with HLB equal to or less than 7 comprise propylene glycol caprylate or a phosphatidic acid derivative thereof.

Embodiment 8

The composition of any one of embodiments 1 to 7, which comprises at least two co-surfactants with HLB equal to or less than 7, and at least one of the co-surfactants is a lecithin.

Embodiment 9

The composition of any one of embodiments 1 to 8, wherein the carrier comprises an agent, wherein the agent is a triglyceride or a polyoxyethylene derivative of a triglyceride. Optionally, in some embodiments, the triglyceride or a polyoxyethylene derivative thereof is in an amount between 1% and 20%, in specific embodiments, between 5% and 15%.

Embodiment 10

The composition of embodiment 9, wherein the triglyceride or polyoxyethylene derivative of a triglyceride is a caprylic/capric triglyceride or an oleoyl polyoxyl-6 glyceride.

Embodiment 11

The composition of any one of embodiments 1 to 10, wherein the carrier further comprises an agent, wherein the agent is a derivatized cellulose that is soluble in the composition, a polyoxythene/polyoxypropylene copolymer (known as Poloxamer), polyvinyl acetate phthalate, or polyvinyl pyrolidone. In a specific embodiment of Embodiment 11, the carrier further comprises an agent, wherein the agent is a polyethylene oxide polypropylene oxide block copolymer (such as $HO(C_2H_4O)_a(C_3H_6O)_b(C_2H_4O)_aH$).

Embodiment 12

The composition of embodiment 11, wherein said agent is a poloxamer. Optionally, in some embodiments, the poloxamer is in an amount between 5% and 30%, in specific embodiments, between 5% and 25% or 10% and 25%.

Embodiment 13

The composition of embodiment 11, wherein the molecular mass of the hydrophobic block of the polyethylene oxide polypropylene oxide block copolymer (such as $HO(C_2H_4O)_a(C_3H_6O)_b(C_2H_4O)_aH$) is greater than 50% (e.g., greater than 52%) of the total molecular mass of the copolymer, and, optionally, wherein the molecular mass of the hydrophilic block of the polyethylene oxide polypropylene oxide block copolymer (such as $HO(C_2H_4O)_a(C_3H_6O)_b(C_2H_4O)_aH$) is less than 2250 Daltons (e.g., less than 2000 Daltons, less than 1500 Daltons, or less than 1200 Daltons). The composition of embodiment 12, wherein the molecular mass of the hydrophobic block of the poloxamer is greater than 50% of the total molecular mass of the poloxamer and the molecular mass of the hydrophilic block of the poloxamer is less than 2250 Daltons.

Embodiment 14

The composition of embodiment 11, wherein said agent is a derivatized cellulose, and wherein said derivatized cellulose is hydroxypropylmethyl cellulose, hydroxypropyl methyl cellulose acetate phthalate, or hydroxypropyl methyl cellulose acetate succinate.

Embodiment 15

The composition of any one of embodiments 9 to 14, wherein said agent inhibits crystallization of the DIM-related indole on dispersion of the composition in water or intestinal fluids.

Embodiment 16

The composition of embodiment 15, wherein the agent inhibits crystallization of the DIM-related indole as determined by in vitro dispersion testing or in vitro digestion testing.

Embodiment 17

The composition of any one of embodiments 1 to 16, wherein the DIM-related indole is present in the composition in a concentration from 10 mg/ml to 300 mg/ml, 10 mg/mL to 200 mg/mL, 30 mg/ml to 150 mg/ml, 70 mg/ml to 130 mg/ml, or 90 mg/ml to 125 mg/ml.

Embodiment 18

The composition of any one of embodiments 1 to 17, wherein the DIM-related indole in the composition is in an amount at least, or more than 5% or 7.5% by weight.

Embodiment 19

The composition of embodiment 18, wherein the DIM-related indole in the composition is in an amount at least, equal to or more than 10% or 12% by weight.

Embodiment 20

The composition of any one of embodiments 1 to 18, wherein the DIM-related indole in the composition is in an amount from 2% to 20%, 5% to 20%, 7.5% to 15%, 8% to 20%, 8% to 14%, 9% to 13%, or 10% to 12%, or 1% to 14%, or 12 to 14% by weight.

Embodiment 21

The composition of any one of embodiments 1 to 20, wherein the carrier solvent is a solvent that is pharmaceutically acceptable or acceptable when present in food, and wherein the carrier solvent is a Caprylocaproyl polyoxyl-8 glyceride, diethylene glycol monoethyl ether, propylene glycol, or an essential oil.

Embodiment 22

The composition of embodiment 21, wherein the essential oil is peppermint oil, rosemary oil, orange oil, lemon oil, tea tree oil, wintergreen oil, lavender oil, ginger oil, nutmeg oil, fennel oil, eucalyptus oil, rosemary oil, or borage oil. In some embodiments, this list of essential oils further includes, pomegranate seed oil, black cumin oil, rice germ oil, rice bran oil, krill oil, and green-lipped muscle oil. In some embodiments, this list further includes, without limitation, sunflower oil. In other embodiments, the essential oil is not sunflower oil. In some embodiments, the essential oil is not olive oil. In one preferred embodiment, the essential oil is peppermint oil. In one preferred embodiment, the essential oil is rosemary oil.

Embodiment 23

The composition of any one of embodiments 1 to 22, wherein the carrier solvent is in an amount greater than or equal to 4% or 5% by weight, or from 4% to 50% by weight.

Embodiment 24

The composition of any one of embodiments 1 to 23, wherein the one or more surfactants with an HLB of greater than 7 is Polysorbate 80.

Embodiment 25

The composition of any one of embodiments 1 to 23, wherein the one or more surfactants with an HLB of greater than 7 is a Lauroyl polyoxyl 32 glyceride or a polyoxyethyl hydroxyl stearate.

Embodiment 26

The composition of any one of embodiments 1 to 25, wherein the composition does not comprise TPGS, and/or does not comprise cod liver oil.

Embodiment 27

The composition of any one of embodiments 1 to 26, which, upon dispersion in water or intestinal fluids, emulsifies to form a dispersion of oil-in-water globules or forms an emulsion of oil-in-water-globules).

Embodiment 28

The composition of embodiment 27, wherein at least 50% of the globules is less than, or the globules have a mean particle size less than, 1.5 µm, 1 µm, 0.75 µm, 0.5 µm, 0.5 µm or 0.3 µm in size (e.g., in diameter).

Embodiment 29

The composition of embodiment 27, wherein at least 50% of the globules is between 0.01 and 1 µm, between 0.01 and 0.6 µm or between 0.02 and 0.4 µm in size (e.g., in diameter).

Embodiment 30

The composition of embodiment 27, wherein the globules have a mean particle size (e.g., diameter) between 0.01 and 1 µm, between 0.01 and 0.6 µm, between 0.02 and 0.4 µm, between 0.05 and 0.2 µm, or between 0.02 and 0.2 µm.

Embodiment 31

The composition of any one of embodiments 28 to 30, wherein the size of the particles is determined by in vitro dispersion testing.

Embodiment 32

The composition of any one of embodiments 1 to 31, which, 2 hours after ingestion by a subject, provides the DIM-related indole in a plasma of the subject in a concentration of at least or more than 150 ng/ml, 200 ng/ml, 250 ng/ml or 300 ng/ml, or between 200 ng/ml and 600 ng/ml, between 250 ng/ml and 500 ng/ml, or between 300 ng/ml and 400 ng/ml.

Embodiment 33

The composition of any one of embodiments 1 to 32, which, upon ingestion by a subject, provides Cmax of the DIM-related indole of at least or more than 150 ng/ml, 200 ng/ml, 250 ng/ml or 300 ng/ml (e.g., in a plasma of a subject).

Embodiment 34

The composition of any one of embodiments 1 to 33, which, upon ingestion by a subject, achieves mean or average AUC (ng/ml*hr) of the DIM-related indole of at least or more than 500 ng/ml*hr, 750 ng/ml*hr, 1000 ng/ml*hr, 1250 ng/ml*hr or 1500 ng/ml*hr, or between 750 ng/ml*hr and 2000 ng/ml*hr, or between 1000 ng/ml*hr and 2000 ng/ml*hr, or between 1250 and 1750 ng/ml*hr.

Embodiment 35

The composition of any one of embodiments 1 to 34, wherein the DIM-related indole is 3,3' diindolylmethane (DIM).

Embodiment 36

The composition of any one of embodiments 1 to 34, wherein the DIM-related indole is LTR.

Embodiment 37

The composition of any one of embodiments 1 to 36, wherein the composition is shelf-life stable for at least or more than 6 months, 1 year, 2 years, or 5 years.

Embodiment 38

The composition of embodiment 37, wherein the stability is characterized by lack of re-crystallization of the DIM-related indole.

Embodiment 39

The composition of any one of embodiments 1 to 38, which is formulated for oral use (e.g., a capsule).

Embodiment 40

The composition of any one of embodiments 1 to 39, wherein the composition is formulated as a soft shell gelatin capsule or a hard shell gelatin capsule.

Embodiment 41

The composition of any one of embodiment 1 to 40, which is formulated for topical use.

Embodiment 42

The composition of embodiment 41, which is further diluted with solvent for processing onto delivery devices, optionally, the solvent is isopropanol, ethanol or acetone, and optionally the dilution is to a ratio of not more than 9:1 (i.e., solvent 9 parts to 1 part of the composition (comprising a DIM-related indole)) on a wt/wt basis. Optionally, the solvent-diluted composition can be applied to a delivery vehicle (e.g., a tampon, a wound dressing, a food item, a suppository, or any other delivery vehicle described herein), and then dried to evaporate the solvent.

Embodiment 43

The composition of any one of embodiments 1 to 42, wherein the composition comprises an effective amount of DIM. Optionally, the composition comprises from 25 to 100 mg of the DIM-related indole, e.g., per dose (e.g., per capsule).

Embodiment 44

The composition of any one of embodiments 1 to 43, which further comprises retinyl palmitate (as an additional API), e.g., in an effective amount.

Embodiment 45

The composition of any one of embodiments 1 to 43, which further comprises retinyl palmitate and Vitamin D (as additional APIs), e.g., in effective amounts.

Embodiment 46

The composition of any one of embodiments 44-46, wherein the retinyl palmitate is in an amount from 2.75 to 10 mg.

Embodiment 47

A method for treating acne in a human subject in need thereof comprising administering the composition of any one of embodiments 1 to 46 to the subject.

Embodiment 48

The method of embodiment 47 comprising administering the composition of any one of claims 44 to 46 to the subject.

Embodiment 49

The method of embodiment 47 comprising further co-administering retinyl palmitate to the subject (e.g., in an effective amount).

Embodiment 50

The method of embodiment 49, wherein retinyl palmitate is co-administered at the same time or concomitantly to the subject.

Embodiment 51

The method of any one of embodiments 47-50, which is effective to treat acne when administration is performed for a period of at least 3 months or at least 6 months.

Embodiment 52

The composition of any one of embodiments 1 to 43, which further comprises Melatonin (as an additional API), e.g., in an effective amount.

Embodiment 53

A method for promoting sleep, reducing sleep latency or reducing the number of night-time awakenings in a human subject in need thereof comprising administering the composition of embodiment 52 to the subject.

Embodiment 54

The composition of any one of embodiments 1 to 43, which further comprises Vitamin K (as an additional API), e.g., in an effective amount. Optionally, Vitamin K is Vitamin K2, e.g., in the amount from 25 µg to 1600 µg per dose.

Embodiment 55

A method for promoting bone health or promoting heart health in a human subject in need thereof comprising administering the composition of embodiment 54 to the subject.

Embodiment 56

The composition of any one of embodiments 1 to 43, which further comprises Bicalutamide, artemether or tamoxifen (as additional APIs), e.g., in an effective amount.

Embodiment 57

The method of any one of embodiments 47-51, 53 and 55, wherein the administering is performed once a day, or twice a day.

Embodiment 58

The method of any one of embodiments 47-51, 53, 55 and 57, wherein the administration is oral.

Embodiment 59

A method for treating atopic dermatitis in a subject (such as a mammal, e.g., a human, a dog, or a cat) in need thereof comprising administering (e.g., orally administering, optionally, once or twice a day) the composition of any one of embodiments 1 to 43 to the subject.

Embodiment 60

A composition comprising a DIM-related indole having Log P from 3 to 5.5 (e.g., DIM) and a carrier, wherein the carrier comprises a solvent (e.g., Transcutol® and/or Labrasol® ALF), a triglyceride (e.g., Labrafac® AC WL1349, Labrafil® M1944CS, and/or olive oil), a surfactant (e.g., Cordasol® HS-HP, Polysorbate 80, and/or Gelucire® 44/14), a co-surfactant (e.g., a phosphatidyl choline (such as Phospholipon 85G) and/or Capryol® 90), and, optionally, an additional surfactant or co-surfactant (e.g., Gelucire® 44/14 and/or Capryol® 90). Instead of the specific components identified by their trade names, an equivalent component in accordance with Table 1, or an equivalent component described in the specification or known in the art, can be used in such compositions. Further, optionally, such composition may comprise a polymer (e.g., Poloxamer 124, and/or another polymer described in the specification or known in the art) and/or a second active ingredient (e.g., Retinyl Palmitate). In certain specific embodiments, such composition comprises DIM in the amount of about 10% to 12% by weight and a carrier, wherein the carrier comprises a solvent (e.g., Transcutol® and/or Labrasol® ALF) in the amount of about 35% to 51% by weight, a triglyceride (e.g., Labrafac® AC WL1349, Labrafil® M1944CS, and/or olive oil) in the amount of about 8% to 20% by weight, a surfactant (e.g., Cordasol® HS-HP, Polysorbate 80, and/or Gelucire® 44/14) in the amount of about 15% to 25% by weight, a co-surfactant (e.g., a phosphatidyl choline (such as Phospholipon 85G) and/or Capryol® 90) in the amount of about 4% to 12% by weight, and, optionally, an additional surfactant or co-surfactant (e.g., Gelucire® 44/14 and/or Capryol® 90) in the amount of about 4% to 10% by weight. In a preferred embodiment, such composition comprises a phosphatidyl choline as a co-surfactant, e.g., in the amount of about 4% to 12% by weight (such as 4-12% by weight), or about 8% to 10% by weight (such as 8-10% by weight). In a preferred embodiment, such composition comprises an oleoyl polyoxyl-6 glyceride (e.g., Labrafil® M1944CS) as a triglyceride (and, not, e.g., a propylene glycol di-caprylate), e.g., in the amount of about 8% to 10% by weight (such as 8-10% by weight). In a preferred embodiment, such composition further comprises a polymer such as Poloxamer 124, e.g., in the amount of about 11% to 52% by weight (such as 11-52% by weight), or about 24% to 52% by weight (such as 24-52% by weight). Generally, the term "about" as used herein encompasses a range of values between 25% greater than and 25% less than the stated value; in one embodiment, the term "about" encompasses a range of values between 10% greater than and 10% less than the stated value. The specific values stated and ranges between the specific stated values are also contemplated and preferred. In a preferred embodiment, the compositions described herein, upon dispersion in water or contact with intestinal fluids, emulsify to form a dispersion of oil-in-water globules which have a particle size or diameter (e.g., mean particle size or diameter) of 0.01 to 0.5 micron (μm), such as about 0.02, about 0.03, about 0.08, about 0.1, about 0.15, or about 0.2 micron (μm) (or any range in between these values).

Embodiment 61

A composition comprising a DIM-related indole having Log P from 3 to 5.5 (e.g., DIM) and a carrier, wherein the carrier comprises a solvent oil (e.g., peppermint oil and/or rosemary oil), one or more surfactants (e.g., Gelucire® 44/14 and/or Polysorbate 80), one or more co-surfactants (e.g., Capryol® 90 and/or a phosphatidyl choline), and, optionally, a second active ingredient (e.g., melatonin). Instead of the specific components identified by their trade names, an equivalent component in accordance with Table 1, or an equivalent component described in the specification or known in the art, can be used in such compositions. In certain specific embodiments, such composition comprises DIM in the amount of about 10% to 12% by weight and a carrier, wherein the carrier comprises a solvent oil (e.g., peppermint oil and/or rosemary oil) in the amount of about 10% to 12% by weight, a surfactant (e.g., Gelucire® 44/14) in the amount of about 35% by weight, a co-surfactant (e.g., Capryol® 90) in the amount of about 10% to 18% by weight, an additional surfactant (e.g., Polysorbate 80) in the amount of about 25% by weight, and, optionally, an additional co-surfactant (e.g., a phosphatidyl choline) in the amount of about 4% to 8% by weight. In one preferred embodiment, the solvent oil is rosemary oil. Generally, the term "about" as used herein encompasses a range of values between 25% greater than and 25% less than the stated value; in one embodiment, the term "about" encompasses a range of values between 10% greater than and 10% less than the stated value. The specific values stated and ranges between the specific stated values are also contemplated and preferred. In a preferred embodiment, the compositions described herein, upon dispersion in water or contact with intestinal fluids, emulsify to form a dispersion of oil-in-water globules which have a particle size or diameter (e.g., mean particle size or diameter) of 0.01 to 0.5 micron (μm), such as about 0.03, about 0.05, about 0.08, about 0.1, about 0.15, about 0.2, or about 0.3 micron (μm) (or any range in between these values).

Embodiment 62

The composition of any of embodiments 1 to 61 or any other composition or formulation described herein, which does not comprise monomer polyvinyl caprolactam (which is also known as polyvinyl caprolactam-polyvinyl acetate-polyethylene glycol graft copolymer, and also known as a polyethylene glycol, polyvinyl acetate and polyvinylcaprolactame-based graft copolymer) (such as Soluplus®). The composition of any of embodiments 1 to 61, wherein the carrier does not comprise monomer polyvinyl caprolactam (which is also known as polyvinyl caprolactam-polyvinyl acetate-polyethylene glycol graft copolymer, and also known as a polyethylene glycol, polyvinyl acetate and polyvinylcaprolactame-based graft copolymer) (such as Soluplus®).

The invention is further explained by the following illustrative examples:

6. EXAMPLES

6.1 Example 1. Determination of Physicochemical Characteristics of DIM and Related Multimeric Indole Compounds This example describes assessment of the relevant physicochemical characteristics of DIM and structurally related multimeric indole compounds.

DIM has demonstrated the characteristics of stability in neutral and acidic media. When tested in water DIM demonstrated a maximal solubility of 0.7 μg/ml. When tested in an aqueous acid environment of pH 2, which is similar to the human gastric environment, the solubility was essentially unchanged with a maximal solubility of 0.6 μg/ml. In directly determining the solubility of DIM the shake-flask method for determination of maximum solubility in aqueous media was utilized. The solubility was determined as described by Lindenberg et al., 2004, Eur J Pharm Biopharm. 58(2):265-78. The drug was weighed in excess of its expected solubility in Uniprep® vials equipped with a 0.45-μm membrane filter, and 2 ml of Milli-Q water, 0.01N HCL (pH 2.0), or phosphate buffer (pH 7.4) (USP) was added into the vial. The vials were incubated at 37±0.5° C. while shaking on a "Polymax 1040" orbital shaker (Heidolph, Schwabach). The samples of the solutions were taken after 4 or 24 hours by pressing the Uniprep® plunger down, diluted as appropriate, and the concentration of DIM was analyzed by HPLC, as described below. The measurements were done in triplicate. The maximum concentration of DIM in aqueous media used in this study was 0.6 μg/ml. The solubility or stability was not influenced by pH and was similar in water, 0.01N HCl or PBS (pH 7.4). When tested in Octanol using the same Shake-flask method and HPLC determination of DIM concentration, results revealed a concentration of 2,300 μg/ml DIM. Using these results the experimental log P for DIM was determined to be 3.583.

Based on a Log P of 3.583, DIM is a molecule of uncertain formulation requirements for Lipid Based Formulations (LBFs) since the log P is not greater the 5 which would indicate candidacy for formulations targeting lypmphatic uptake and transport. A log P of 3.583 and in the range of 3 and greater also indicates poor water solubility and difficulty for formulations to increase water solubility sufficiently to enter hepatic portal venous blood.

A log P of 3.583 for DIM indicating middle range or intermediate lipid solubility for DIM, together with low water solubility and the uncertainty of solubility of DIM in specific lipid components, emphasizes the need for formulations specifically developed to accomodate DIM.

Using DIM as a lead compound having a multimeric indole structure, it is an object of the present invention to provide SMEDDS formulations to achieve improved bioavailability of DIM and multimeric indole compounds closely related to DIM, which, like DIM, possess similar limited solubility and requirements for formulation in LBF's, for example, as demonstrated by their experimental or calculated log P values. Such compounds include 2-(indol-3-ylmethyl)-3,3'-Diindolylmethane (LTR), the trimeric indole multimer, 2,2-bis(3,3'indolyl) acetaldehyde, and additional dimeric, substituted DIM-related compounds described in U.S. Pat. Nos. 6,589,975, 6,444,697, and 6,323,233.

Calculated log P evaluation of DIM and the related compounds included use of the ChemDraw Ultra 12.0 software. (CambridgeSoft). The ChemDraw methods applied to the calculated Log P's of interest include three fragmentation methods which are used to predict the log P values. Method one was based on 94 atomic contributions evaluated from 830 molecules by least squares analysis. This method works with a standard deviation of 0.47 log P units and can handle molecules containing hydrogen, oxygen, nitrogen, sulfur and halogens in addition to carbon. Method two is an extension of method one but is based on 120 atomic contributions evaluated from 893 molecules by least squares analysis. This method works with a standard deviation of 0.50 log P units. Method three is based on 222 atomic contributions calculated from 1868 molecules by least squares analysis. This method allows a calculation of log P with a standard deviation of 0.43 log P units and can handle molecules containing hydrogen, oxygen, nitrogen, sulfur, halogens and phosphorus atoms. Therefore calculated Log P results using ChemDraw Ultra 12.0 can be expected to provide Log P within 0.5 log P units of experimental log P's and be instructive as to whether there is applicability of the SMEDDS formulations developed for DIM to structurally related, multimeric indole compounds. Results summarizing experimental and calculated Log P's are presented in the following table:

| Indole Compound | Structure | Experimental log P Determination | Calculated log P's (source) |
| --- | --- | --- | --- |
| 3,3'-Diindolylmethane (aka bis(3,3'-indolyl)methane (DIM)) | 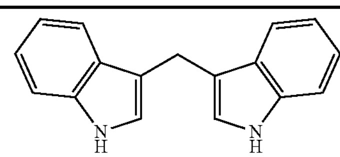 | 3.583 | 3.21[a], 4.05[b], 4.26[c] |
| 2,2'-Diindolylmethane | 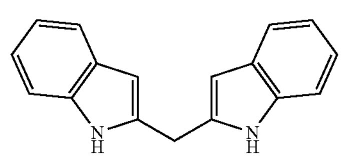 [SMILES: c1ccc2[nH]c(Cc3cc4ccccc4[nH]3)cc2c1] | Not Determined | 3.01[a] |
| 2,2-bis(3,3'-indolyl) acetaldehyde | 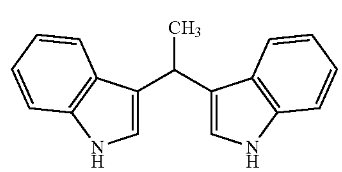 [SMILES: CC(c1c[nH]c2ccccc12)c1c[nH]c2ccccc12] | Not Determined | 3.54[a] |
| 2,2-bis(2,2'-indolyl) acetaldehyde | 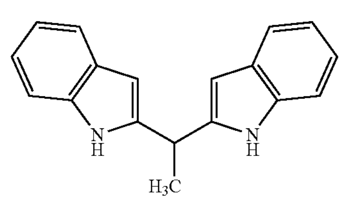 [SMILES: CC(c1cc2ccccc2[nH]1)c1cc2ccccc2[nH]1] | Not Determined | 3.49[a] |

| Indole Compound | Structure | Experimental log P Determination | Calculated log P's (source) |
|---|---|---|---|
| 5-Me-DIM | 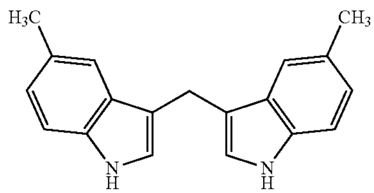 [SMILES: Cc1ccc2[nH]cc(Cc3c[nH]c4ccc(C)cc34)c2c1] | Not Determined | 4.18[a] |
| 5-Cl-DIM | 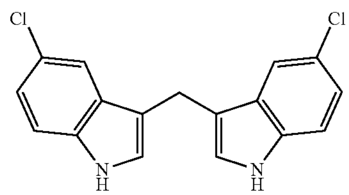 [SMILES: Clc1ccc2[nH]cc(Cc3c[nH]c4ccc(Cl)cc34)c2c1] | Not Determined | 4.32[a] |
| 5-F-DIM | 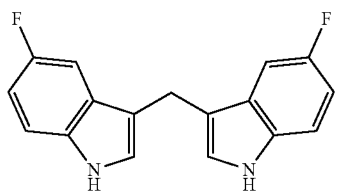 [SMILES: Fc1ccc2[nH]cc(Cc3c[nH]c4ccc(F)cc34)c2c1] | Not Determined | 3.52[a] |
| 2-Me-DIM | 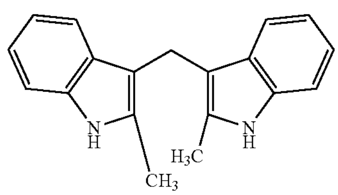 [SMILES: Cc1[nH]c2ccccc2c1Cc1c(C)[nH]c2ccccc12] | Not Determined | 3.88[a] |
| 2-(indol-3-ylmethyl)-3,3'-Diindolylmethane (LTR) | 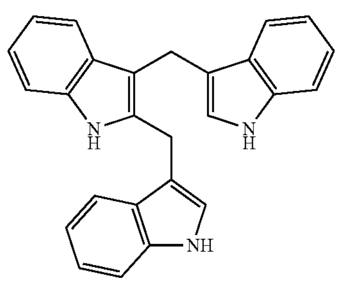 [SMILES: c1ccc2c(Cc3[nH]c4ccccc4c3Cc3c[nH]c4ccccc34)c[nH]c2c1] | Not Determined | 4.76[a] |
| methyl 2,2-bis(1-methyl-1H-indol-3-yl)acetate | 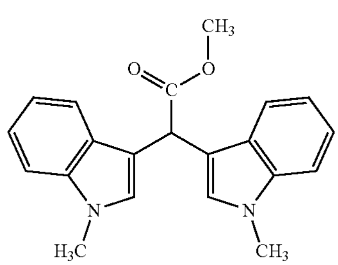 [SMILES: COC(=O)C(c1cn(C)c2ccccc12)c1cn(C)c2ccccc12] | Not Determined | 3.11[a] |

[a]ChemDraw Ultra 12.0 software. (CambridgeSoft)
[b]http://www.chemspider.com/Chemical-Structure.2963.html
[c]http://www.chemicalize.org/structure/#!mol=c1ccc2c%28c1%29c%28c%5BnH%5D2%29Cc3c%5BnH%5Dc4c3cccc4&source=fp Based on the overlapping experimental and calculated Log P values for DIM, and calculated log P values for closely related 2,2-bis(3,3'indolyl) acetaldehyde both of these compounds are expected to function similarly in the SMEDDS formulations described herein. LTR has higher lipid specific solubility requirements as indicated by a calculated Log P of 4.76. However based on the inherent variation of 0.5 Log P unit from calculated to experimental Log P's, the actual Log P for LTR is predicted to be within 1 log P unit of the actual DIM log P and to have a comparable lipid solubility and performance to DIM in the SMEDDS formulations described herein.

Because of the similar log P values, and thus, similar physicochemical properties, of DIM, DIM dimer 2,2-bis(3,3'indolyl) acetaldehyde, and DIM trimer (2-(indol-3-ylm-ethyl)-3,3'-diindolylmethane [also written: 2 (Indol-3-ylm-ethyl)-indol-3-yl]indol-3-ylmethane] (LTR), the self-emulsifying compositions described herein are expected to be compatible not only with DIM, but also with the DIM dimer and with LTR, as well as with other multimeric indole compounds structurally related to DIM with calculated or experimental log P values between 3 and 5.5, or preferably between 3.2 and 5, or most preferably between 3.2 and 4.5.

6.2 Example 2. Evaluation and Ranking of Excipients for Development of a SMEDDS System for DIM and DIM-Related Compounds The present invention is the result of the determination of unique combinations of excipients that dissolve crystalline Diindolylmethane (DIM) (and are expected to dissolve structurally related multimeric indole compounds) to form pre-concentrates. Upon ingestion, the performance of these SMEDDS formulations results in increased oral bioavailability of DIM compared to crystalline DIM as well as increased bioavailability compared to spray dried formulations where DIM is complexed with tocopherol PEG 1000 succinate (TPGS).

The first step in this development process was the testing of a variety of excipients chosen as potentially active in solubilizing DIM. Table 1 shows some of the results of this study. The method involved weighing of approximately 2 grams of each of the liquid excipients into a small vial. Subsequently, a small amount of DIM was added and the mixture was shaken. Further, small amounts of DIM were added until no further DIM was observed to go into solution using microscopic observation.

TABLE 1

| Trade Name | Chemical Name(s) | HLB | DIM Solubility | Category of Excipient oil/Solvent, Surfactant, Co-Surfactant, Particle Modifier |
|---|---|---|---|---|
| Transcutol® | Diethylene glycol monoethyl ether | N/A | >25% | Solvent |
| Plurol Oleique | Glycerol mono/di-oleate | 6 | 5% | Co-surfactant |
| Capryol PGMC | Propylene glycol monocaprylate | 5 | 8% | Co-surfactant |
| Lauroylglycol 90 | Propylene glycol monolaurate | 5 | 3% | Co-surfactant |
| Labrafil® M1944CS | Oleoyl polyoxyl-6 glycerides Oleoyl macrogol-6 glycerides Apricot kernel oil PEG-6 esters PEG-5 oleate | 4 | 5% | Co-surfactant |
| Labrafac® AC WL1349 | Medium-chain triglycerides Medium chain fatty acid triglyceride Caprylic/Capric triglyceride | 3 | 3% | Oil |
| Labrafac® PG | Propylene glycol di-caprylate | 2 | 4.5% | oil |
| Capryol® 90 | Propylene glycol monocaprylate | 6 | 7% | Co-surfactant |
| Labrasol® ALF | Caprylocaproyl polyoxyl-8 glycerides Caprylocaproyl macrogol-8 glycerides Caprylocaproyl polyoxylglycerides PEG-8 Caprylic/Capric glycerides | 12 | 25% | Solvent |
| Peceol | Glycerol monooleate | 3 | 2% | Co-surfactant |
| Propylene glycol | N/A | N/A | 2% | Solvent |
| Maisine 35-1 | Glyceryl monolinoleate | 4 | 2% | Co-surfactant |
| Gelucire® 44/14 | Lauroyl polyoxyl-32 glycerdies Lauroyl macrogol-32 glycerides Lauroyl Polyoxylglyceride | 14 | 19% | Surfactant |
| Crodasol® HS-HP | Mixture of monoesters and diesters of 12-hydroxystearic acid and macrogols | 14-16 | 14% | Surfactant |
| Polysorbate 80 | Polyoxyethylelene (20) sorbitan monooleate (x)-sorbitan mono-9-octadecenoate poly(oxy-1,2-ethanediyl) | 15 | 12% | Surfactant |
| Peppermint oil | Mixture | — | 4% | Oil |

From the above testing and results, it was established that the solvent excipients Transcutol® and Labrasol® ALF are good candidates to dissolve the DIM. Gelucire® 44/14 can act as both a solvent and a high HLB surfactant to build an effective emulsion. A low HLB surfactant, acting as a co-surfactant such as Capryol® 90 also showed that it too can dissolve appreciable amounts of DIM. In looking at possible oil-like triglycerides to improve absorption of the DIM, the Labrafil® M1944CS was identified as a good candidate that showed slightly better solubility than the medium chain triglycerides.

In looking at possible solvents, such as oils, to use for Nutritional Supplement formulations, classical oils such as olive oil or sunflower oil were ruled out because of very low ability to dissolve DIM. However, peppermint oil was found to have a modest ability to dissolve DIM. Based on the above data, emulsifiers (surfactants and co-surfactants) approved for nutritional supplement use that were found to be good candidates include Polysorbate 80, Gelucire® 44/14, and Capryol® 90.

6.3 Example 3. Formulations of Candidate Mixtures of Oil Solvents, Surfactants, Co-Surfactants, and Additional Components Using the information described in Example 2, various DIM formulations were prepared, some of which are described herein. The description of certain formulations in Table 2, below, indicates the weight of each component in the formulation in grams with a total of 10 grams per formulation placed in small vials. The dispersions of such formulations were tested for particle size by laser diffraction following dispersion and spontaneous emulsion formation in water.

Each of the formulations were tested by dispersing approximately 1 gram of the candidate formulation in 200 mL of deionized water at approximately 37° C. with slow stirring of a magnetic spin bar in a 1 L beaker. Within five minutes of the addition, sufficient mixture was added to a Malvern Mastersizer dynamic laser light scattering instrument to satisfy the obscuration of the laser beams needed for measurement.

6.4 Example 4. In Vitro Self-Emulsification and Particle Size Testing with Additional Particle Modifying DIM SMEDDS Components. Unexpected Benefits from the Use of Phosphatidyl Choline and Poloxamer Various additional agents were tested for possible benefit in producing stable spontaneous emulsions in water in an effort to reduce the globule/particle size. These additional agents included such agents as Soluplus and Poloxomer 124. Table 3 shows exemplary formulations tested.

Some of the formulations were formulated with and without Soluplus and with and without phosphatidyl choline-rich isolates from lecithin. The formulations were tested by dispersing approximately 1 gram of the candidate formulation in 200 mL of deionized water at approximately 37° C. with slow stirring of a magnetic spin bar in a 1 L beaker. Within five minutes of the addition, sufficient mixture was added to a Malvern Mastersizer dynamic laser light scattering instrument to satisfy the obscuration of the laser beams needed for measurement.

TABLE 2

Particle Size Results from Initial Formulation Studies for Formulations A to F

| Formulation | DIM, g | Solvent + wt., g. | Triglycerides + Amount, g. | Surfactant, g. | Co-surfactant, g. | Additional Surfactant or Co-surfactant, g. | Particle Size, μm |
|---|---|---|---|---|---|---|---|
| A | 1.0 g (i.e., 10%) | Transcutol ®, 3.5 g (i.e., 35%) | Labrafac ® AC WL1349, 1.0 g (i.e., 10%), Labrafil ® M1944CS, 1.0 g (i.e., 10%) (20% total) | Crodasol ® HS-HP, 1.5 g (i.e., 15%) | Phospholipon 85G, 1.0 g (i.e., 10%) | Gelucire ® 44/14, 1.0 g (i.e., 10%) | 0.22 |
| B | 1.0 g (i.e., 10%) | Transcutol ®, 4.0 g (i.e., 40%) | Olive oil 2.0 g. (i.e., 20%) | Polysorbate 80 2.0 g. (i.e., 20%) | Phospholipon 85G, 1.0 g (i.e., 10%) | — | 7.0 |
| C | 1.0 g (i.e., 10%) | Labrasol ® ALF, 3.5 g (i.e., 35%) | Labrafac ® AC WL1349, 1.0 g (i.e., 10%) Labrafil M1944CS, 1.0 g (i.e., 10%) (20% total) | Crodasol ® HS-HP, 1.5 g (i.e., 15%) | Phospholipon 85G, 1.0 g (i.e., 10%) | Gelucire ® 44/14 1.0 g (i.e., 10%) | 0.14 |
| D (aka29A) | 1.2 g (i.e., 12%) | Labrasol ® ALF, 5.1 g (i.e., 51%) | Labrafac ® AC WL1349, 1.0 g (i.e., 10%) | Gelucire ® 44/14, 1.9 g (i.e., 19%) | Phospholipon 85G, 0.8 g (i.e., 8%) | | 0.2 |
| E | 1.2 g (i.e., 12%) | Labrasol ® ALF, 5.1 g (i.e., 51%) | Labrafac ® AC WL1349, 1.0 g (i.e., 10%) | Gelucire ® 44/14, 1.9 g (i.e., 19%) | — | Capryol ® 90 0.8 g (i.e., 8%) | 0.8 |
| F | 1.2 g (i.e., 12%) | Labrasol ® ALF, 5.1 g (i.e., 51%) | Labrafac ® AC WL1349, 1.0 g (i.e., 10%) | Gelucire ® 44/14, 1.9 g (i.e., 19%) | Phospholipon 85G, 0.4 g (i.e., 4%) | Capryol ® 90 0.4 g (i.e., 4%) | 0.3 |

Formulations A, B, C, D and F contain phosphatidyl choline, whereas Formulation E does not contain phosphatidyl choline. Formulations A, B, C, D, E or F do not contain poloxamer.

Unexpected Effect of Phosphatidyl Choline on DIM SMEDDS

As indicated by the particle size results in Table 2, above, and Table 3, below, the use of Phospholipon 85G, which is principally a phosphatidyl choline, in the formulation resulted in unexpectedly very fine particle dispersion as compared to a more classical low HLB surfactant such as Capryol 90 (compare formulations D and E). Even when half and half classical low HLB surfactant and phosphatidyl choline was used, a smaller particle size dispersion was produced than with the use of low HLB surfactant alone (see comparison of E and F formulations). This demonstrates unexpected activity for phosphatidyl choline which results in a reduction in globule size on dispersion of the DIM SMEDS in aqueous media. Phosphatidyl choline improves the dispersion capability of the SMEDDS formulations indicating that the use of phosphatidyl choline is likely to result in improved bioavailability of these formulations. Reduced particle size of SMEDDS formulations upon dispersion in vitro has been linked to increased bioavailability in vivo (see Sha et al., 2012, Int J Nanomedicine 7:705-12).

Based on these unexpected findings a variety of naturally derived phosphatidyl choline (PC) preparations including highly concentrated PC isolates from soy and sunflower are also contemplated in the pharmaceutical and nutraceutical formulations described herein. For nutraceutical DIM SMEDDS, PC isolates from sunflower are preferred as a non-genetically modified source with high PC content. Other natural and semi-synthetic and synthetically modified forms of PC are also contemplated, and can be tested for ability to minimize globule size of the emulsified SMEDDS formulation and improve solubility of DIM during digestion. Available and potentially useful forms of PC are known in the art (see, e.g., van Hoogevest et al., 2014, Eur J Lipid Sci Technol. 116(9):1088-1107, which is incorporated by reference herein).

Unexpected Effect of Poloxamer on DIM SMEDDS

A number of polymers were considered for inclusion in the DIM formulations, including hydroxypropyl methyl cellulose, hydroxypropyl methyl cellulose acetate phthalate, a proprietary polymer from BASF known as Soluplus®, and various polyoxyethylene-polyoxypropylene copolymers generally known as poloxamers. Poloxamers are known to improve oral bioavailability and are amphiphilic or possessing both hydrophobic and hydrophilic portions on the molecule.

It was found that there was little useful solubility of the cellulosic polymers in the mixture. Soluplus® was soluble with added heat to complete dissolution. However, when active ingredient was included with the surfactant/polymer (Soluplus®) mixture and then dispersed in water, a stringy polymer precipitated rather than forming a fine droplet dispersion. The addition of the Poloxamer 124 not only dissolved but also served to uniformly gel the product when cooled to ambient temperature.

Poloxamers were suggested for use in pharmaceutical compositions containing DIM in U.S. Patent Publication No. 2013/0065933. However, the compositions described in U.S. Patent Publication No. 2013/0065933 are different from the compositions described herein, and U.S. Patent Publication No. 2013/0065933 discloses the use of poloxamers with a hydrophobic block in the copolymer of less than 50 mass % and a hydrophilic block of 2250 Daltons or more, whereas Poloxamer 124 has a hydrophobic block of just over 53% and the hydrophilic block is approximately 1050 Daltons in size.

TABLE 3

Particle Size Results from Follow On Formulation Studies for Formulations G to M

| Formulation | Active, Amount | Solvent + wt., g. | Triglycerides + Amount, g. | Surfactant + Amount, g. | Co-surfactant + Amount, g. | Polymer + Amount, g. | Particle Size, μm |
|---|---|---|---|---|---|---|---|
| G | DIM 1.2 g (i.e., 12%) | Labrasol® ALF, 2.8 g (i.e., 28%) | Labrafil® M1944CS, 1.0 g (i.e., 10%) | Gelucire® 44/14, 1.8 g (i.e., 18%) | Phospholipon 85G, 0.8 g (i.e., 8%) | Poloxamer 124 2.4 g (i.e., 24%) | 0.031[a] 0.079[b] |
| H | DIM 1.2 g (i.e., 12%) | | Labrafil® M1944CS, 1.0 g (i.e., 10%) | Gelucire® 44/14, 1.8 g (i.e., 18%) | Phospholipon 85G, 0.8 g (i.e., 8%) | Poloxamer 124 5.2 g (i.e., 52%) | 0.085[a] |
| I | DIM 1.2 g (i.e., 12%) | Transcutol®, 4.0 g (i.e., 40%) | | Gelucire® 44/14, 2.5 g (i.e., 25%) | Capryol 90, 1.2 g (i.e., 12%) | Soluplus 1.1 g (i.e., 11%) | |
| J Pharma + RP | DIM 1.2 g + 2 mg Retinyl Palmitate (i.e., about 12% total) | Labrasol® ALF, 2.8 g (i.e., 28%) | Labrafil® M1944CS, 0.8 g (i.e., 8%) | Gelucire® 44/14, 1.8 g (i.e., 18%) | Phospholipon 85G, 1.0 g (i.e., 10%) | Poloxamer 124, 2.4 g (i.e., 24%) | 0.48[a] |
| K | DIM, 1.2 g (i.e., 12%) | Labrasol® ALF, 2.8 g (i.e., 28%) | Labrafil® M1944CS, 1 g (i.e., 10%) | Gelucire® 44/14, 1.8 g (i.e., 18%) | Capryol® 90, 0.8 g (i.e., 8%) | Poloxamer 124, 2.4 g (i.e., 24%) | |
| L No Polox | DIM 1.2 g (i.e., 12%) | Labrasol® ALF, 5.1 g (i.e., 51%) | Labrafil® M1944CS, 1 g (i.e., 10%) | Gelucire® 44/14, 1.9 g (i.e., 19%) | Phospholipon 85G, 0.8 g (i.e., 8%) | | 0.164[b] |
| M | DIM 1.2 g (i.e., 12%) | Labrasol® ALF, 2.8 g (i.e., 28%) | Labrafil® M1944CS, 1 g (i.e., 10%) | Gelucire® 44/14, 1.8 g (i.e., 18%) | Capryol-90, 0.4 g (i.e., 4%) Phospholipon 85G, 0.4 g (i.e., 4%) (total 8%) | Poloxamer 124, 2.4 g (i.e., 24%) | 0.134[a] |

[a]Determined using Malvern Mastersizer
[b]Determined using Nicomp Particle Sizing Systems Particle size measurements for formulations with and without Poloxamer 124 were performed as described above. The results of the testing using instrument Malvern Mastersizer, are shown in Table 3, above. A smaller particle size dispersion was produced when Poloxamer 124 was used (see formulations G, H and L). This demonstrates unexpected activity for Poloxamer 124 which results in reduction in globule size on dispersion of the DIM SMEDS in aqueous media. This indicates that the use of poloxamer in self-emulsifying DIM formulations is likely to result in improved bioavailability of these formulations.

It should also be noted that addition of the Poloxamer 124 caused the formulation to gel at room temperature. This gel appeared to be quite stable with time. Filling of standard gelatin capsules with this formulation does not present problems and the capsules do not show and deformation or leakage during storage.

The globule or drop size of the dispersed phase containing a mixture of oils and surfactants with the dissolved active ingredient is determined by a number of factors including the method of preparation, the concentration and identity of the oil/surfactant system and the relative amounts of the individual components. The median globule size as reported in a well prepared system is generally a normal distribution.

One of the problems associated with development of SMEDDS formulations is that although API may initially disperse in mixtures of oils and surfactants, the API ingredient can precipitate from the micro-emulsion on further stirring. This was observed for the early experimental DIM formulations tested by the inventors to begin to occur at approximately 10 to 12 minutes. This was confirmed during experiments to examine the effect of lipolysis media on the dispersion particle size and DIM solubility. The problem of precipitation of DIM relates to the characteristic of DIM to readily reform crystals of DIM when dissolved at saturating concentrations in any solvent system. Modification of the recrystallization process has the potential to improve overall solubility, extend the time of active absorption of DIM in the GI track, and improve overall bioavailability. The impact of recrystallization from SMEDDS formulation most importantly occurs during passages of the SMEDDS emulsified formulation into the upper small intestine where pancreatic lipases, other digestive enzymes, and bile salts cause digestive breakdown and modification of the surfactant system. The potential digestive effects on SMEDDS performance in vivo are best determined through in vitro lipolysis testing.

Formulation G, formulated with the Poloxamer 124, when stirred into water, did not show crystals of DIM forming for over 20 minutes. Thus, a doubling of the time for the start of precipitation when dispersed in water was observed with the use of poloxamer 124. The inhibition of recrystallization by the use of poloxamer is another unexpected and beneficial activity of poloxamer (in addition to its role in reducing globule size), which indicates that the use of poloxamer in self-emulsifying DIM formulations is likely to result in improved bioavailability of self-emulsifying DIM formulations. The Formulation G also showed the smallest globule diameter of all formulations tested when particle size was determined through dispersion in water and assay by dynamic light scattering using both the Malvern Mastersizer and Nicomp Particle Sizing Instruments.

6.5 Example 5. Development of a Nutritional Supplement DIM SEDDS Formulation Since not all of the excipients listed in the above formulations are approved as food ingredients, an alternate formulation acceptable for nutritional supplements required further development. An initial examination of food grade oils such as soybean oil, corn oil, or sunflower oil did not show promise in producing fine particle dispersions. It was unexpectedly found that peppermint oil dissolved a small amount of the DIM, thus, it was used for further studies. A formulation with and without phosphatidyl choline (PC) was prepared to further confirm the utility of the addition of the PC rather than a more typical co-surfactant. Dispersed globule size measurements were performed and shown in Table 4.

TABLE 4

Nutritional SMEDDS Formulation Development

| Formulation | Active Ingredient g. | Solvent Oil, g. | Surfactant g. | Co-surfactant g. | Addition. surfactant g. | Co-surfactant g. | Ave. particle size μm |
|---|---|---|---|---|---|---|---|
| N With PC | DIM, 1.2 g (i.e., 12%) | Peppermint Oil, 1.0 g (i.e., 10%) | Gelucire ® 44/14, 3.5 g (i.e., 35%) | Capryol ® 90, 1.0 g (i.e., 10%) | Polysorbate 80, 2.5 g (i.e., 25%) | Phosphatidyl choline 0.8 g (i.e., 8%) | 0.128[a] |
| O With PC Melatonin | DIM, 1 g (i.e., 10%) Melatonin, 0.2 g (i.e., 2%) (12% total) | Peppermint Oil, 1.0 g (i.e., 10%) | Gelucire ® 44/14, 3.5 g (i.e., 35%) | Capryol ® 90, 1.0 g (i.e., 10%) | Polysorbate 80, 2.5 g (i.e., 25%) | Phosphatidyl choline 0.8 g (i.e., 8%) | 0.087[a] |
| P Without PC | DIM, 1.2 g (i.e., 12%) | Peppermint Oil, 1 g (i.e., 10%) | Gelucire ® 44/14, 3.5 g (i.e., 35%) | Capryol ® 90, 1.8 g (i.e., 18%) | Polysorbate 80, 2.5 g (i.e., 25%) |  | 0.239[a] 0.291[b] |
| Q With Lower PC | DIM, 1.2 g (i.e., 12%) | Peppermint Oil, 1 g (i.e., 10%) | Gelucire ® 44/14, 3.5 g (i.e., 35%) | Capryol ® 90, 1.4 g (i.e., 14%) | Polysorbate 80, 2.5 g (i.e., 25%) | Phosphatidyl choline 0.4 g (i.e., 4%) | 0.184[a] |

[a] Determined using Malvern Mastersizer
[b] Repeat determination using Malvern Mastersizer on a separate day Formulations N, O, P and Q do not contain poloxamer.

6.6 Example 6. Formulation D Used in Human Bioavailability Plasma Studies

The following were added to a small scintillation vial in the following order: 5.1 grams Caprylocaproyl polyoxyl-8 glycerides (Labrasol ALF), 1.9 grams Lauroyl polyoxyl 32 glycerides (Gelucire 44/14) and 1.0 grams Caprylic/Capric triglyceride. The mixture was warmed and gently agitated to uniformity. 0.8 grams of phosphatidyl choline (Lipoid Phospholipon 85G) was added to the mixture with warming to approximately 80° C. After cooling to approximately 50° C., 1.2 grams of diindolylmethane was added with continuing agitation until the mixture was uniform.

6.7 Example 7. Formulation G—A Pharmaceutical Formulation

The following were added to a small scintillation vial in the following order: 2.8 grams Caprylocaproyl polyoxyl-8 glycerides (Labrasol ALF), 1.8 grams Lauroyl polyoxyl 32 glycerides (Gelucire 44/14), 2.4 grams Poloxamer 124, 1.0 grams Oleoyl polyoxyl-6 glycerides. The mixture was warmed and gently agitated to uniformity. 0.8 grams of phosphatidyl choline (Lipoid Phospholipon 85G) was added to the mixture with warming to approximately 80° C. After cooling to approximately 50° C., 1.2 grams of diindolylmethane was added with continuing agitation until the mixture was uniform.

6.8 Example 8 Formulation J—A Pharmaceutical Formulation with Retinyl Palmitate The following were added to a small scintillation vial in the following order: 2.8 grams Caprylocaproyl polyoxyl-8 glycerides (Labrasol ALF), 1.8 grams Lauroyl polyoxyl 32 glycerides (Gelucire 44/14), 2.4 grams Poloxamer 124, 0.8 grams Oleoyl polyoxyl-6 glycerides. The mixture was warmed and gently agitated to uniformity. 0.8 grams of phosphatidyl choline (Lipoid Phospholipon 85G) was added to the mixture with warming to approximately 80° C. After cooling to approximately 50° C., 1.2 grams of diindolylmethane was added with continuing agitation until the mixture was uniform. In a separate small scintillation vial, a 100:1 dilution of Retinyl Palmitate was prepared by adding 100 mg of retinyl palmitate to 9.90 grams of oleoyl polyoxyl-6 glycerides. 200 mg of this dilution was added to the formulation representing 2.0 mg of retinyl palmitate and the mixture stirred to uniformity.

6.9 Example 9. Formulation L—A Pharmaceutical Formulation without Poloxamer

The following were added to a small scintillation vial in the following order: 5.1 grams Caprylocaproyl polyoxyl-8 glycerides (Labrasol ALF), 1.9 grams Lauroyl polyoxyl 32 glycerides (Gelucire 44/14), 1.0 grams Oleoyl polyoxyl-6 glycerides, 0.8 grams of phosphatidyl choline (Lipoid Phospholipon 85G) was added to the mixture with warming to approximately 80° C. The mixture was gently agitated to uniformity. After cooling to approximately 50° C., 1.2 grams of diindolylmethane was added with continuing agitation until the mixture was uniform.

6.10 Example 10 Formulation K—with Capryol

The following were added to a small scintillation vial in the following order: 2.8 grams Caprylocaproyl polyoxyl-8 glycerides (Labrasol ALF), 1.8 grams Lauroyl polyoxyl 32 glycerides (Gelucire 44/14), 2.4 grams Poloxamer 124, 1.0 grams Oleoyl polyoxyl-6 glycerides. The mixture was warmed and gently agitated to uniformity. 0.8 grams of Propylene Glycol Caprylate (Capryol 90) was added to the mixture with warming to approximately 50° C. This was followed with 1.2 grams of diindolylmethane with continued agitation until the mixture was uniform.

6.11 Example 11 Formulation N—A Nutritional Formulation with PC

The following were added to a small scintillation vial in the following order: 3.5 grams Lauroyl polyoxyl 32 glycerides (Gelucire 44/14), 1.0 grams of Propylene Glycol Caprylate (Capryol 90), 1.0 grams Peppermint oil, and 2.5 grams Polysorbate 80. The mixture was warmed with stirring to 80° C. and 0.8 grams of phosphatidyl choline (Lipoid Phospholipon 85G) was added to the mixture with stirring. After cooling to approximately 50° C., 1.2 grams of diindolylmethane was added with continuing agitation until the mixture was uniform.

6.12 Example 12 Formulation P—A Nutritional Formulation without PC

The following were added to a small scintillation vial in the following order: 3.5 grams Lauroyl polyoxyl 32 glycerides (Gelucire 44/14), 1.8 grams of Propylene Glycol Caprylate (Capryol 90), 1 grams Peppermint oil, and 2.5 grams Polysorbate 80. The mixture was warmed with stirring to approximately 50° C., 1.2 grams of diindolylmethane was added with continuing agitation until the mixture was uniform.

6.13 Example 13 Formulation O—A Nutritional Formulation with Melatonin

The following were added to a small scintillation vial in the following order: 3.5 grams Lauroyl polyoxyl 32 glycerides (Gelucire 44/14), 1.0 grams of Propylene Glycol Caprylate (Capryol 90), 1.0 gram Peppermint oil, and 2.5 grams Polysorbate 80. The mixture was warmed with stirring to 80° C. and 0.8 grams of phosphatidyl choline (Lipoid Phospholipon 85G) was added to the mixture with stirring. After cooling to approximately 50° C., 1 grams of diindolylmethane and 0.2 grams of melatonin was added with continuing agitation until the mixture was uniform.

6.14 Example 14: Production of Dosage Forms for DIM SMEDS

The formulations described herein can be filled into either hard gelatin capsules or soft gelatin capsules. In production, hard gelatin capsules can be filled with the use of a liquid fill system that is set to dispense the warmed liquid formulation into hard gelatin capsules. When hand filling capsules, the use of a hand filling template apparatus is advised. Here, the capsules are simply separated with the lower larger part placed in the holes of the template. A measured amount of liquid is filled into each capsule with a syringe. The top cap is placed on to each lower half and with the apparatus the top capsules are snapped into place. The capsules are removed from the apparatus, ready for packaging.

For soft gelatin capsules, the warmed liquid is pumped to the capsule making equipment. A separate tank of warm gelatin solution is metered to the equipment. A ribbon of gelatin is fed to each side of the capsule filler to fill molds which form each half of the shell. The filler meters the formulation as the two halves are fused together in the equipment. The soft capsules are dried before going to the packaging station.

6.15 Example 15: In Vitro Testing to Simulate In Vivo Digestive Changes and Performance of DIM SMEDDS Formulations In vitro methods to simulate in vivo performance of Lipid Based Formulations (LBFs) have been developed which have been shown to predict overall bioavailability of LBFs following oral administration to animals and humans. These methods include In Vitro Dispersion Testing and In Vitro Simulated Digestions Testing. For highly water insoluble compounds like DIM and LTR some gastrointestinal precipitation and reformation of crystal structure of the Active Pharmaceutical Ingredient (API) is expected. Upon recrystallization, changes in crystal structure to more amorphous crystals with smaller size indicate potential for increased solubilization and greater bioavailability in the gastro-intestinal environment (see Clas SD, 2003, Curr Opin Drug Discov Devel. 6(4):550-60). Both In Vitro Dispersion Testing and In Vitro Simulated Digestions Testing were used to test the performance of the optimized formulations of the present invention which demonstrated the smallest and most stable globule size upon initial particle size testing for self-emulsifying behavior.

Materials, Formulations, and Methods

Materials $CaCl_2$ and Tris (hydroxymethylaminomethane) were purchased from Chimie Plus Laboratoire (Décines, France). NaCl, HCl 37%, NaOH pellets were bought from Merck (Darmstadt, Germany). Sodium taurodeoxycholate (NaTDC), tributyrine, pancreatin (from porcine pancreas), L-α-phosphatidylcholine, and 4-bromophenylboronic acid were purchased from Sigma-Aldrich. All solvents used have HPLC grade.

Formulations

Formulations were prepared according to the methods of manufacture described in Examples 6 (Formula D), 7 (Formula G), 11 (Formula N), and for Formula M (See Table 3)

Testing Methods

Dispersion Test

A dispersion test was performed on the miscible formulations in a USP dissolution bath. 830 µL of miscible mixture was introduced in 250 mL of purified water at 37° C. under agitation with a paddle at 100 rpm. Performance criteria were: ease of emulsification, homogeneity and fineness of the dispersion. The fineness of the dispersion was assayed by dynamic light scattering (DLS, Particle Sizing Systems Nicomp). Photomicrographs were obtained of crystals observed during light microscopic observation following 30 minutes of dispersion.

In Vitro Simulated Digestive Lipolysis of DIM SMEDDS Formulations

Preparation of Media and Enzyme Suspension:

The lipolysis buffer was prepared by adding Tris (0.474 g/L), $CaCl_2$ (0.208 g/L) and NaCl (8.810 g/L) in Milli-Q water. The pH was adjusted at 6.5 with NaOH 0.6 M.

The lipolysis medium was prepared by adding L-α-phosphatidylcholine (0.576 g/L) and NaTDC (1.565 g/L) in the lipolysis buffer. The medium was stirred overnight to allow the complete solubilization of lecithin.

The pancreatin solution was prepared by adding 1 g of pancreatin powder in 5 mL of lipolysis buffer. After 10 minutes of magnetic stirring the solution was centrifuged (Universal centrifuge 320R) at 2800 g and 5° C. for 10 min. The supernatant was sampled to be used in the lipolysis test.

Performance of the In Vitro Lipolysis Test

The experimental setup consisted of a pH stat apparatus (Metrohm® AG, Switzerland), comprising a Titrando 802 propeller stirrer/804 Ti Stand combination, a glass pH electrode (iUnitrode) and one 800 Dosino dosing units coupled to 5 mL autoburette. The apparatus was connected to a PC and operated using Tiamo 2.0 software. The equipment was thermostated at 37° C. and filled with lipolysis medium, to mimic fasted state in the small intestine. During the digestion of lipid-based formulations by pancreatic lipases, pH was maintained constant by the addition of NaOH 0.2N.

Before the lipolysis test, the specific activity of pancreatic lipases was checked on tributyrine (model substrate). The substrate must be in excess to have a reaction rate directly proportional to the enzyme concentration. Five hundred microliter (µL) of tributyrine and 1.5 µL of pancreatin solution were introduced in 28 mL of lipolysis medium (without lecithin). The specific activity of pancreatic lipases should be higher than 900 U/mg.

830 µL of lipid-based formulation (corresponding to 100 mg of DIM), was added to 36 mL of lipolysis medium at 37° C. After 10 minutes (dispersion/emulsification time), 4 mL of pancreatin solution was added. The duration of the test was 1 hour. Aliquots of 1 mL were sampled at various time points to determine the solubility of the drug in the micellar phase: t=−5 min (during the dispersion time), t=0 min (before the addition of the pancreatic solution), t=5 min, t=15 min, t=30 min and t=60 min.

Five µL of the inhibitor solution (1M: 100 mg of 4-bromophenylboronic acid in 0.5 mL of methanol) was added immediately to each sample. They were then centrifuged at 21 000 g and 37° C. for 30 minutes. The supernatant was sampled and diluted with acetonitrile (1/5) for further HPLC analysis. Solutions were then filtered on PVDF filters 0.2 µm.

HPLC Analysis

Samples were analyzed according to the Eurofins HPLC Method for Diindolylmethane (DIM), UV max 280 nm.

Results and Discussion

Dispersion Test

The dispersion of the formulation in 250 mL of water (equivalent to the FDA glass of water) was followed for observance of the precipitation of DIM after 30 minutes and was checked by polarized light microscopy. Study of Formulation "D" lead to the formation of a fine and turbid emulsion with a crystal formation showing particle size distribution of 283±66 nm (volume). Microscopic study of Formulations L and N after 30 minutes revealed smaller crystal structures as compared to Formulation D. The size of crystal structures for formulations L and N were reduced by a factor of 10 compared to formulation D. The advantageous reduction in crystal size for Formulation L compared to Formulation D is attributed, at least in part, to the use of longer chain triglycerides present in Labrafil® in Formulation L versus shorter chain triglycerides present in Labrafac® in Formulation D. Formation of a spontaneous emulsion with Formulation N after 30 minutes resulted in small crystalline structures contained within spherical globules. The advantageous reduction in crystal size for Formulation N compared to Formulation D is attributed, at least in part, to a contribution from Peppermint Oil and low concentration of Polysorbate 80 (see FIGS. 4A, 4B and 4C).

Lipolysis Test

The dispersion of the formulations in the lipolysis medium was tested at the beginning of the lipolysis experiment (830 µL of formulation in 36 mL of medium).

Results for Formulation D showed that it formed a fine and turbid dispersion in the lipolysis medium. The precipitation of the API from this formulation was quicker in this medium than in purified water. The lipolysis test confirmed that the API DIM precipitates after dispersion in the lipolysis medium simulating the content of the fasted small intestine. Only 22±2 mg of DIM was still in solution after 10 minutes of dispersion (100 mg of DIM were introduced in the pH-stat). This quantity stayed the same until the addition of the pancreatin solution. The lipolysis of the Formulation D leads to a significant decrease of the quantity of DIM only a few minutes after the addition of the digestive enzymes.

Testing of Formulas G, L, and N were carried out using methods described above. Each formulation resulted in the spontaneous formation of fine and turbid emulsions.

Results showing the Particle Size after Dispersion and the Dissolution of DIM following exposure to Digestive Enzymes is presented in Table 5 and summarized in FIG. 3.

The evaluation of DIM SMEDDS formulations described herein with in vitro testing to simulate in vivo performance of the DIM showed that the use of certain components in the formulations yields surprising effects. Specifically, addition of a form of poloxamer polymer changes formulation's response to dispersion in water, the process of recrystallization and solubility of DIM in media simulating fasted intestinal content. Observation of the recrystallization process in water may indicate changes in crystal structure and size which are known to influence bioavailability (see Clas SD., 2003, Curr Opin Drug Discov Devel. 6(4):550-60). The obtained results indicate an unexpected benefit from the substitution of Oleoyl polyoxyl-6 glycerides for Propylene glycol di-caprylate. This resulted in a 10 fold decrease in crystal size observed following 30 minutes of dispersion documented by light microscopy comparing Formula L (with Oleoyl polyoxyl-6 glycerides) to Formula D (with Propylene glycol di-caprylate). FIGS. 4A and 4B show equivalent size crystals for Formula L at 20× magnification to Formula D at 10× magnification, documenting a 10× difference.

Additionally, as demonstrated in FIG. 3, addition of Poloxamer 124 in Formulation G increased solubility of DIM in digestive media compared to both Formulation L

TABLE 5

| Formulation | Particle Size Diameter after Dispersion in Water (nm) | Mg DIM Dissolved in Lipolysis Medium at 10 minutes | Mg DIM Dissolved After 15 minutes Digestion in Lipolysis Medium with Pancreatin | Mg DIM Dissolved After 30 minutes Digestion in Lipolysis Medium with Pancreatin | DIM Crystal Characteristics In Water Dispersion |
|---|---|---|---|---|---|
| Unformulated Crystalline DIM | 3,010[1] | Not Tested | Not Tested | Not Tested | Large Cuboidal |
| Formulation "D" Without Poloxamer and with PC | 283[2] | 22 | 2.5 | 2.0 | Smaller Cuboidal FIG. 4A (×10 magnification) |
| Formulation "L" without Poloxamer and with PC | 147[2] | 19.3 | 2.7 | 2.1 | Smaller Cuboidal than "D" FIG. 4B (×20 magnification) |
| Formulation "G" with Poloxamer and with PC | 70[2] | 20.5 | 7.9 | 6.4 | Smallest Cuboidal |
| Formulation "N" with PC and without Poloxamer | 302[2] | 16.0 | 9.6 | 7.0 | Globules without crystals FIG. 4C (×20 magnification) |

Notes:
[1]Malvern Mastersizer, DIM, as supplied by BioResponse
[2]Particle Sizing Systems Nicomp Conclusions:

In Vitro Dispersion and Simulated Digestive Lipolysis evaluation of Formulations such as those of the present invention is an established technology to compare formulations in order to identify the best formulations in terms of their ability to maintain the drug in solution during the dispersion and digestion steps. Maintaining solubilization in such testing has been directly linked to bioavailability of the formulation in vivo (see Cuiné et al., 2008, J Pharm Sci. 97(2):995-1012). The observed changes in crystal structure to smaller and/or a more amorphous form also can benefit bioavailability by facilitating the re-dissolution of the drug in the intestinal environment supporting both immediate and sustained absorption by the intestinal epithelium.

and Formulation D which lacked poloxomer. This resulted in more than a doubling of DIM solubility when DIM solubility was compared at 15 and 30 minutes (see FIG. 3 and Table 5). The nutritional DIM SMEDDS formulation N also supported DIM solubility comparable to the poloxomer-containing formulation G indicating that other non-polymer components can function to improve DIM solubility during simulated digestion. Common elements in the interactive components of the Formula G DIM SMEDDS and the Formula N SMEDDS formulation include phosphatidyl choline and Lauroyl polyoxyl 32 glycerdies. Compared to formula D, which showed low levels of dissolved DIM, Formula G included increased levels of long chain fatty acids in the oil component of the LBF. Increased presence of long chain fatty acids is known to stabilize LBF's to resist the influence of digestive enzymes which is an objective of the present invention.

Formulation N showed doubling of DIM solubility compared to Formulation D, even though both formulations contain PC and lack poloxamer, which is a surprising finding, suggesting that the interaction of Peppermint Oil and Polysorbate 80 (food grade ingredients in Formulation N) performs equally well and contribute the same solubility advantage, as does the addition of the poloxymer and long chain fatty acids (Labrafil) in Formulation G. Therefore, both Formulations G and N produced advantages over Formulation D. This is significant since Formulation D was shown to be clearly more bioavailable in human testing than Spray Dried BR-DIM (see FIGS. 1 and 2). Since improved solubility in the digestive test employed here directly correlates with improved bioavailability in vivo, both Formulations N and G are expected to outperform Formulation D in terms of bioavailability in vivo (in humans).

These results support the expectation that the formulations described herein would result in increased overall bioavailability of DIM and physicochemically related multimeric indoles. The described SMEDDS containing DIM in association with more long chain fatty acids, low concentrations of Poloxamer 124, and Lauroyl polyoxyl 32 glycerdies were associated with increased solubilization of DIM in simulated digestive conditions. Greater and more prolonged solubilization of the API in such testing has been directly linked to improving the bioavailability of the emulsified API in vivo (see Cuiné et al., 2008, J Pharm Sci. 97(2):995-1012).

6.16 Example 16: Single Dose Human Bioavailability Testing of DIM, Spray-Dried DIM, and Self-Emulsifying DIM Formulations Introduction:

Based on the availability of spray-dried, microencapsulated, absorption enhanced DIM (BioResponse DIM [BR-DIM], BioResponse, Boulder, Colo.) as a widely available dietary supplement formulation, a study in human volunteers to directly compare the bioavailability of DIM from generic crystalline DIM, from BR-DIM, and from the self-emulsifying (SMEDDS) formulations described herein was designed. Oral bioavailability studies are the most definitive model to establish relative performance of new formulation technology as developed for the SMEDDS DIM and LTR Formulations, assessing relative absorption from different formulations of DIM. Such studies allow direct comparison of the relative bioavailability of DIM formulations in humans and are possible based on the existence of validated, quantitative plasma analysis methodology for DIM (see Heath et al., 2010, Am J Transl Res. 2(4):402-11). To this end, a basic comparative pharmacokinetic evaluation was conducted in human volunteers to compare absorption, presence of DIM in plasma over time, and tolerability.

The BR-DIM formulation consists of microparticle complexes of DIM with Vitamin E TPGS suspended or "microencapsulated" in a starch-based particle matrix. Vitamin E TPGS is a GRAS approved excipient consumed in foods and pharmaceuticals. The starch matrix consists of either Capsul starch, refined from corn starch, or alternatively is composed of Gum Arabic and Maltodextrin. All of these starches are used in foods and dietary supplements. Gum Arabic and Maltodextrin are additionally approved for use in pharmaceuticals.

Formulation "D" described above was used as a self-emulsifying (SEDDS) DIM formulation.

Summary of Study Design:

Study Design: Single Center, Single-Blind, Single Dose, Oral Bioavailability Study, with Subject Crossover.

In Part I of the Study, a treatment group was administered a 300 mg dose of DIM from BR-DIM or a 300 mg dose of DIM from crystalline DIM on the first study day, followed by crossover to the other DIM formulation on the second study day, at least 14 days following the first treatment. 3 subjects were given crystalline DIM, 4 subjects were given BR-DIM. One subject receiving BR-DIM on the first day did not return for the second day, resulting in a N of 3 for crystalline and a N of 4 for BR-DIM.

In Part II of the Study, five individuals, four of whom participated in Part I of the Study, were administered a 300 mg dose of DIM from DIM SMEDDS Formulation D. Testing of DIM SMEDDS formula D took place on one day with 5 subjects. The subjects were all healthy, adult volunteers, both male and female, not consuming DIM containing supplements and in a fasting state on study days. Volunteers agreed not to consume cruciferous vegetable for one week prior to study days. Study groups consisted of 3, 4, or 5 individuals.

Conduct of Study:

For Part I of the Study, and after an overnight fast, all subjects had an indwelling Teflon catheter placed in a forearm vein. A baseline blood specimen was collected. For Part I of the Study, subjects ingested matching, opaque gelatin capsules containing either crystalline DIM (300 mg) or BR-DIM providing 300 mg DIM. Then, the subjects provided 8 cc samples of blood was collected at Baseline, and 1 hr, 2 hr, 3 hr, 4 hr, and 6 hr after administration of each of the formulations. A standard small meal was given at 4 hrs.

For Subsequent Evaluation of Formulations G and N and after an overnight fast, all subjects had an indwelling Teflon catheter placed in an a forearm vein. A baseline blood specimen was collected. Subjects ingested opaque gelatin capsules containing SEDDS DIM formulation (in particular, Formulation D described above) providing 300 mg dissolved DIM. The DIM SMEDDS formulation was provided in 3 hard gelatin capsules each containing 100 mg of DIM. Subsequently, 8 cc samples of blood were obtained and 30 cc samples of urine will be obtained according to the following chart. Blood was collected at Baseline, and 1 hr, 2 hr, 3 hr, 4 hr, and 6 hr after administration of the drug. A standard small meal was given at 4 hrs.

The study described above is to be followed up by a Part III study, described below.

For Part III of the Study, and after an overnight fast, all subjects will have an indwelling Teflon catheter placed in an a forearm vein. A baseline blood speciment will be collected. Subjects will ingest opaque gelatin capsules containing either a SMEDDS DIM formulation made with pharmaceutical excipients or a SMEDDS DIM formulation made with nutritional excipients. Each formulation will provide 300 mg dissolved DIM contained in 3 hard gelatin capsules each containing 100 mg of DIM. 8 cc samples of blood will be collected at Baseline, and 1 hr, 2 hr, 3 hr, 4 hr, and 6 hr after administration of each of the drugs. A standard small meal will be given at 4 hrs.

Blood sample handling: Within 15 minutes, plasma was centrifuged and frozen, stored on dry ice, then stored at minus 80 until assayed.

Additional Data: All subjects in the Part I and Part II of the Study completed and all subjects in Part III of the Study will complete a tolerability questionnaire with entries at 2, 4, 6, and 8 hrs.

Reporting adverse events: Adverse events were recorded for the Part I and Part II of the Study and will be recorded for the Part III of the Study in a structured interview, and reported as required.

Method for Plasma Analysis and Pharmacokinetic Comparison:

Pharmacokinetic evaluation was performed for all subjects. Blood samples (~8 ml for each) were collected at 0 (baseline), 1, 2, 3, 4, and 6 hours after the oral administration of the dose of DIM, BR-DIM, or DIM SMEDDS formulation (i.e., Formulation D described above). Within 15 minutes of the collection, the blood samples were centrifuged at 4° C., at 2000 g for 10 minutes, and plasma was collected immediately after centrifugation and transferred to the screw-cap polypropylene cryogenic tubes. The plasma samples were stored at −80° C. until analysis.

The concentrations of DIM in human plasma samples were determined by a validated high-performance liquid chromatography with tandem mass spectrometry (LC-MS/MS) method. Briefly, to 50 µl human plasma, 100 µl of 2% formic acid in methanol (containing 1 µg/mL internal standard zileuton) was added to precipitate proteins. The mixture was vortex-mixed for 1 minute, and centrifuged at 14,000 g at 4° C. for 10 minutes. The supernatant was collected and 10 µl was injected into the LC-MS/MS system. Chromatographic analysis was performed using a Waters model 2690 separation system (Milford, Mass., USA). The analytes were separated on a Waters X-Terra MS column (150 mm×2.1 mm i.d.) using a mobile phase consisting of methanol/0.45% formic acid (70:30, v/v), and isocratic flow at 0.2 mL/min. The analytes were monitored by a Waters Micromass triple quadrupole mass spectrometer (Milford, Mass., USA) using an electrospray probe in the positive ionization mode operating at a cone voltage of 23V for DIM and 13V for the internal standard zileuton. Samples were introduced into the ionization source through a heated nebulized probe (350° C.). The collision energy was set at 30 eV and 9 eV for DIM and zileuton, respectively. The transitions at 129.9>76.8 and 237.1>161.1 were monitored for DIM and zileuton, respectively. The linear calibration curve was set over the DIM plasma concentration range of 10 to 5,000 ng/mL. The lower limit of quantitation (LLOQ) was determined at 10 ng/mL for DIM in human plasma. The intra- and inter-day accuracy and precision were within the generally accepted criteria for bioanalytical method (<15%).

The pharmacokinetic parameters for individual patients were estimated using non compartmental analysis with the computer software program WinNonlin version 5 (Pharsight Corporation, Mountain View, Calif.). The maximum plasma concentration (Cmax), the time of occurrence for the Cmax (Tmax), were obtained by visual inspection of the plasma concentration-time curves after the oral administration. The total area under the plasma concentration-time curve from time zero to the last measurable time point (AUC0-t) was calculated using the linear and logarithmic trapezoidal method for ascending and descending plasma concentrations, respectively.

Results:

Tolerability: All 300 mg single doses of DIM for all formulations were well tolerated with no side effects reported in interviews and up to 8 hours following the time of ingestion. Further follow-up at 24 hours confirmed the absence of any side effect during this time period.

Pharmacokinetics: The following chart summarizes the averaged pharmacokinetic findings for each of the formulations studied in Part I and Part II of the Study as described above.

TABLE 6

Plasma pharmacokinetic parameters[a] of DIM after oral administration of a single dose (300 mg) of three formulations in healthy individuals:

| Formulation | n | $T_{max}$ (h) | $C_{max}$ (ng/mL) | $AUC_{0-\infty}$ (ng/mL*h) | $T_{1/2}$ (h) |
|---|---|---|---|---|---|
| Crystalline | 3 | 1.7 | 18.1 | 98.5 | 2.2 |
| BR-DIM | 4 | 3.0 | 68.1 | 242.2 | 4.5 |
| DIM SMEDDS (Formulation D) | 5 | 1.6 | 363.2 | 1507.2 | 2.3 |

[a]Parameters were estimated using non-compartmental analysis with WinNonlin software.
Abbreviations: $T_{max}$, time to reach the maximum concentration; Cmax, maximum plasma concentration; $AUC_{0-\infty}$, total area under the plasma concentration-time curve from time zero to infinity; $T_{1/2}$, terminal plasma half-life; n = number of subjects.

Relative absorption is shown in averaged plasma level data over time comparing crystalline DIM, spray-dried absorption-enhanced DIM (BR-DIM) and a DIM SEDDS oral formulation (Formulation D), see results in FIG. 2, which are also summarized in the table below:

| Time (hour) | Crystaline DIM | DIM SMEDDS Formulation "D" | Spray Dried DIM |
|---|---|---|---|
| 0 | 0.0 | 116.9 | 1.9 |
| 1 | 17.8 | 255.2 | 40.9 |
| 2 | 16.7 | 347.8 | 52.4 |
| 3 | 10.6 | 209.3 | 69.8 |
| 4 | 10.0 | 173.8 | 45.1 |
| 6 | 5.8 | 92.7 | 26.9 |

Relative systemic exposure to DIM is shown in averaged Area Under the Curve (AUC) data comparing area under the plasma concentration-time curve from time zero to infinity achieved with crystalline DIM, spray-dried absorption-enhanced DIM (BR-DIM) and a DIM SEDDS oral formulation (Formulation D), see results in FIG. 1, which are also summarized in the table below:

| | Avg. AUC (ng/ml*hr) | SD | CI (0.05) |
|---|---|---|---|
| Crystalline DIM | 98.5 | 24.25376 | 33.61338 |
| Spray Dried DIM | 242.2 | 150.7892 | 147.7707 |
| DIM SMEDDS Formulation "D" | 1507.2 | 972.6261 | 852.5287 |

Conclusions:

Out of all formulations tested, the least absorption and the lowest Cmax (maximal plasma concentration) and Area Under the Curve (AUC) (correlating with total absorption and bioavailability) were seen with crystalline DIM. Increases of approximately 2-3 times in the pharmacokinetic parameters were seen with the BR-DIM microencapsulated, spray dried formulation compared to crystalline DIM. The absorption of DIM from the self-emulsifying (SMEDDS) DIM formulation was approximately 5-6 times greater than from the BR-DIM formulation as demonstrated by higher Cmax and AUC values. The systemic exposure to DIM, assessed by Cmax and AUC, after oral administration of the DIM SMEDDS formulation was increased by ~20-fold, compared to that achieved after oral administration of the crystalline DIM, while the terminal elimination half-life ($T_{1/2}$) of both formulations was similar. Therefore, the use of self-emulsifying DIM formulation technology described herein achieves significant and unexpected advantages in bioavailability of DIM compared to the bioavailability of DIM from both crystalline DIM and absorption-enhanced, spray-dried BR-DIM formulations.

6.17 Example 17: Solvent-Diluted DIM SMEDDS Adapted for Topical DIM Delivery Preparation of Solvent Diluted DIM SMEDDS formulations for additional formulation development appropriate for various topical applications and delivery of DIM to wet topical surfaces, including topical wounds and selected mucosal surfaces, has been undertaken, These steps provide specialized formulation for site directed DIM delivery to wounds, cervico-vaginal epithelium and mucosa, and rectal mucosa.

The formulations and dosage forms described above were modified with the addition of a compatible Class 3 solvent to DIM SMEDDS formulations to produce a uniform diluted formulation providing for preparation of metered dose topical delivery of DIM from SMEDDS formulations. Solvent diluted DIM SMEDDS can be applied to delivery vehicles such as dry feminine tampons or wound dressings, or can be mixed with suppository bases. Following dipping of the absorbent tampon or metered dispensing on dressing, the diluted DIM SMEDDS dosage form is dried in conditions sufficient to evaporate the solvent. This allows the DIM SMEDDS to re-concentrate as an evenly distributed lipid based formulation. When utilized as a medicated tampon or wound dressing, the DIM SMEDDS formulation emulsifies in the use environment releasing mg amounts of DIM in consistent amounts within desired dose ranges.

The preparation of a solvent-diluted version of the DIM SMEDDS formulation included addition of a selected Class III solvent up to a final solvent: SMEDDS ratio of not more than 9:1 on a wt/wt basis. Preferred DIM SMEDDS formulations to be utilized are formulations K or L (see Table 3). Preferred solvents for dilution include ethanol, isopropanol, and acetone. Most preferred solvent for dilution is isopropanol, and the preparation regime includes mixing and gradual addition of the DIM SMEDDS to the solvent at a temperature of 36-38 degrees Celsius. Once the formulation is applied to a delivery vehicle such as a dry tampon or wound dressing, drying is optionally accomplished in a nitrogen enriched environment to reduce oxidation of the distributed SMEDDS formulation prior to sealing of the delivery vehicle in a unit dose closure system. Making of solvent-diluted DIM SEDDS formulations suitable for topical delivery in delivery vehicles can optionally utilize steps (e.g., for large scale manufacture) described in U.S. Patent Publication No. 2011/0288501, which is incorporated by reference herein in its entirety.

6.18 Example 18: Composition Optimization and Testing of DIM-Related Indole Self-Emulsifying Formulations This example describes preparation of Self-emulsifying Drug Delivery and Nutraceutical Delivery Formulations Containing Diindolylmethane (DIM) as a preferred DIM-Related Indole. This study was undertaken to optimize ingredient composition for antioxidant content of solvent oil and to confirm solubility during In Vitro Dispersion testing and resistance to lipolysis during the in vitro Simulated Digestion Test. Maintenance of greater dissolved DIM during dispersion and during simulated digestion both predict higher bioavailability following oral administration of the self-emulsifying formulations In Vivo.

A. Identification of an Optimal Oil Solvent Screened by Solubility Testing of DIM in Candidate Oils.

The method involved weighing of approximately 2 grams of each of the liquid excipients into a small vial. Subsequently, a small amount of DIM was added and the mixture was shaken. Further, small amounts of DIM were added until no further DIM was observed to go into solution using microscopic observation. Continued testing of acceptable oil solvents for, e.g., nutritional supplement, self-emulsifying formulations using DIM as a representative DIM-related indole active ingredient included testing of the following oils:

| Trade Name | Chemical Name | DIM Solubility % | Type of Oil |
| --- | --- | --- | --- |
| Rosemary Oil | None | 6 | Essential oil |
| Black Cumin | None | 2 | Essential oil |

B. Production of an Optimized Nutritional Self-Emulsifying Formulation Using Dim.

Rosemary oil has antioxidant and anti-inflammatory activity, and was selected as a favorable formulation ingredient. The method of making a bulk DIM-related indole self-emulsifying formulation was developed and conducted. Scaled up production of a 50 gram quantity of a Nutritional Self-emulsifying Formulation for DIM using Rosemary oil (Formulation "R") was conducted and included appropriate mixing of the following ingredients in specified amounts:

| Component | Percentage in formulation | Weight of Component (grams) |
| --- | --- | --- |
| Gelucire 44/14 | 35% | 17.5 |
| Capryol 90 | 10% | 5.0 |
| Rosemary oil | 10% | 5.0 |
| Polysorbate 80 | 25% | 12.5 |
| Phospholipon 85 | 8% | 4.0 |
| DIM | 12% | 6.0 |
| Total: | 100% | 50 gms |

The following ingredients were utilized to produce Formulation "T", a nutritional DIM SMEDSS formulation containing Rosemary oil and Melatonin as a second active:

| Component | Percentage in formulation | Weight of Component (grams) |
| --- | --- | --- |
| Gelucire 44/14 | 35% | 17.5 |
| Capryol 90 | 10% | 5.0 |
| Rosemary oil | 10% | 5.0 |
| Polysorbate 80 | 25% | 12.5 |
| Phospholipon 85 | 7.5% | 3.75 |
| DIM | 12% | 6.0 |
| Melatonin | 0.5% | 0.25 |
| Total: | 100% | 50 gms |

C. In Vitro Dispersion Testing of Optimized Nutritional Self-Emulsifying Formulations Using DIM.

The dispersions of Formulations R and T were tested for particle size by laser diffraction following dispersion and spontaneous emulsion formation in water. Each of the formulations were tested by dispersing approximately 1 gram of the formulation in 200 mL of deionized water at approximately 370 C with slow stirring of a magnetic spin bar in a 1 L beaker. Within five minutes of the addition, sufficient mixture was added to a Malvern Mastersizer dynamic laser light scattering instrument to satisfy the obscuration of the laser beams needed for measurement. The particle size determined is expressed as diameter in microns (µ) in the following chart, and comparison is made to other nutritional and pharmaceutical formulations described herein:

| Type of Formulation | Formulation Name | DIM Content | Particle Size, microns (µ) |
|---|---|---|---|
| Nutritional with Peppermint oil, "N," described in Example 11 and Table 4 | N | 12% | 0.128 |
| Nutritional with Rosemary oil, "R," described in this example and Example 19 | R | 12% | 0.084 |
| Nutritional with Peppermint oil and Melatonin, "O," described in Example 13 and Table 4 | O | 10% | 0.087 |
| Nutritional with Rosemary oil and Melatonin, "T," described in this example and Example 20 | T | 12% | 0.087 |

D. In Vitro Simulated Digestion and Lipolysis Testing of an Optimized Nutritional Self-Emulsifying Formulation Using DIM.

In vitro Simulated Digestion Testing was used to test the performance of the optimized nutraceutical formulation identified as Formulation "R" (described in this example and Example 19). The methods and conditions for testing utilized were exactly the same as described in Example 15: "In Vitro Testing to Simulate In Vivo Digestive Changes and Performance of DIM SMEDDS Formulations." Simulated Digestive Lipolysis evaluation of Formulations such as those described herein is an established technology to compare formulations in order to identify the best formulations in terms of their ability to maintain the API in solution during the dispersion and digestion steps. Maintaining solubilization in such testing has been directly linked to bioavailability of the formulation in vivo (see Cuiné et al., 2008, J Pharm Sci. 97(2):995-1012). The following chart summarizes the percentage of DIM dissolved from Formulation "R" after 10 minutes of dispersion in medium, after 15 minutes of digestion with pancreatin enzyme, and after 30 minutes of digestion with pancreatin enzyme. The performance of the optimized self-emulsifying formulation "R" was compared to performance of formulation "N" (the testing of which is described in Example 15, and the components and making of which are described in Example 11 and Table 4).

| Formulation | Mg DIM Dissolved in Lipolysis Medium after 10 Minutes Dispersion | Mg DIM Dissolved in Lipolysis Medium after 15 Minutes Digestion in Lipolysis Medium with Pancreatin | Mg DIM Dissolved in Lipolysis Medium after 30 Minutes Digestion in Lipolysis Medium with Pancreatin |
|---|---|---|---|
| "N" | 16.0 | 9.6 | 7.0 |
| "R" | 24.8 | 10.3 | 8.4 |

The above results demonstrate a greater percentage of DIM dissolved at 10 minutes after dispersion, and after 15 minutes and 30 minutes of simulated digestion, when formulation "R" is compared to formulation "N". This indicates improved performance and greater expected bioavailability of DIM from "R" compared to "N". In addition, these results demonstrate an unexpected benefit of the Rosemary oil component of "R", since formula "R" was equivalent to formula "N" except for the substitution of Rosemary oil in "R" for the Peppermint oil component of formula "N". Although both formula "N" and "R" demonstrated self-emulsifying activity for DIM, Rosemary oil demonstrated further advantage. Rosemary oil is a terpenoid oil containing p-cymene, linalool, alpha and beta pinene and eucalyptol providing more desirable DIM-related SMEDDS functionality than Peppermint oil which contains terpenoids, oxyterpenoids and sesquiterpenes including menthol, menthone, and menthol esters.

6.19 Example 19. Formulation R—A Nutritional Formulation with PC and Rosemary Oil The following were added to a small scintillation vial in the following order: 3.5 grams Lauroyl polyoxyl 32 glycerides (Gelucire 44/14), 1.0 grams of Propylene Glycol Caprylate (Capryol 90), 1.0 grams Rosemary Oil, and 2.5 grams Polysorbate 80. The mixture was warmed with stirring to 800 C and 0.8 grams of phosphatidyl choline (Lipoid Phospholipon 85G) was added to the mixture with stirring. After cooling to approximately 500 C, 1.2 grams of diindolylmethane was added with continuing agitation until the mixture was uniform. The total amount of ingredients in the formulation was 10 grams.

6.20 Example 20. Formulation T—A Nutritional Formulation with PC, Rosemary Oil, and Melatonin The following were added to a small scintillation vial in the following order: 3.5 grams Lauroyl polyoxyl 32 glycerides (Gelucire 44/14), 1.0 grams of Propylene Glycol Caprylate (Capryol 90), 1.0 gram Rosemary oil, and 2.5 grams Polysorbate 80. The mixture was warmed with stirring to 800 C and 0.75 grams of phosphatidyl choline (Lipoid Phospholipon 85G) was added to the mixture with stirring. After cooling to approximately 500 C, 1.2 grams of diindolylmethane and 0.25 grams of melatonin was added with continuing agitation until the mixture was uniform. The total amount of ingredients in the formulation was 10 grams.

6.21 Example 21. Comparative Pharmacokinetic Evaluation of DIM Pharmaceutical Formulations Repeated single-use of 300 mg oral doses of DIM in different DIM formulations was conducted. Absorption studies using the same adult male subject on separate test days were performed. This allowed comparison of DIM absorption and Plasma Pharmacokinetics through comparison of DIM plasma levels measured following administration of unformulated crystalline DIM, following administration of absorption-enhanced, microencapsulated DIM (BR-DIM), following administration of DIM SMEDDS Formulation "D" without Poloxamer 124, and following administration of DIM SMEDDS Formulation "G" with Poloxamer 124, to the human subject. The same oral administration and timed plasma sampling protocol was used on different study days, separated by at least 2 weeks. Plasma level results for each time point are presented in the following chart. Results demonstrate low absorption following crystalline DIM, increased absorption of DIM from non-SMEDDS, microencapsulated BR-DIM, and further increased absorption from DIM SMEDDS formulations compared to both DIM from crystalline DIM and from BR-DIM. In addition, a further advantage in absorption was demonstrated from Formulation "G" (described in Example 7 and Table 3) which is attributed to more stable self-emulsifying activity compared to DIM SMEDDS Formulation "D" (described in Example 6 and Table 2). This represents In Vivo demonstration of improved bioavailability of DIM from DIM SMEDDS formulation "G" compared to that from formulation "D." This finding is consistent with the finding of greater maintenance of solubility of DIM from formulation "G" compared to "D," which is demonstrated by the In Vitro SMEDDS digestion assay as described in Example 15 and shown in FIG. 3. These results support both the In Vivo performance of Formula "G" as an optimized pharmaceutical DIM SMEDDS formulation and the validity of the In Vitro Simulated Digestion Testing of SMEDDS formulations as a predictor of In Vivo performance of the SMEDDS formulations described herein.

Intra-individual Comparison of Plasma Levels* of DIM following an Oral Dose of Various DIM Formulations Administered on Separate Days:

| Formulation | Time (hr) | | | | | | $C_{Max}$ | AUC | $T_{1/2}$ |
|---|---|---|---|---|---|---|---|---|---|
| | 0 | 1 | 2 | 3 | 4 | 6 | | | |
| Crystalline DIM | 0 | 4.5 | 6.8 | 4.7 | 2.6 | — | 6.8 | 17 | — |
| BR-DIM$^{NG}$ | 0 | 40.9 | 52.4 | 69.8 | 45.1 | 26.9 | 69.8 | 242 | 3 |
| DIM-SMEDDS "D" | 0 | 93.9 | 156.7 | 146.5 | 71.6 | 40.7 | 156.7 | 537 | 1.7 |
| DIM-SMEDDS "G" | 0 | 79.9 | 346.1 | 257 | 186.1 | — | 346.1 | 773 | 2 |

*Plasma levels expressed as ng/ml, determined by validated LCMS/MS Assay 6.22 Example 22. Evidence for Stability of DIM as an API in DIM SMEDDS In order to evaluate stability during storage of DIM in DIM SMEDDS formulations, in particular, in a pharmaceutical DIM SMEDDS formulation, as well as compatibility of API DIM with excipient components of DIM SMEDDS formulations, testing was performed using a sensitive High Performance Liquid Chromatography (HPLC) assay for DIM in DIM SMEDDS. The assay method utilized an HPLC apparatus equipped with column oven, a UV detector and an appropriate data acquisition system and printer-plotter. Weighed amounts of DIM-SMEDDS (Formulation G) were weighed, diluted with acetonitrile, and sonicated. Weighed amounts of commercially available DIM standard (Sigma) was also dissolved in acetonitrile. Samples and standards were injected into the HPLC apparatus. Output was utilized to calculate the content of DIM per gram of composition as % DIM.

Samples from a production lot of a pharmaceutical DIM SMEDDS formulation (Formulation G, described in Example 7 and Table 3) were stored in standard controlled room temperature and humidity conditions and protected from light. The DIM SMEDDS formulation was tested shortly after production, at 1 month post production, and again at 3 months post production. The targeted DIM percentage was 12%. The following chart summarizes results:

| | Time point for Analysis of DIM Content | | |
|---|---|---|---|
| DIM SMEDDS Lot # | Time 0 (Production) | One Month | 3 Months |
| 5-15-15-2 | 12.5% | 13% | 12% |

The results demonstrate that DIM is stable in a DIM SMEDDS formulation during storage. In particular, the results provided in the table above demonstrate stability of DIM in Formulation G, as well as stability of DIM in association with SMEDDS excipients, during storage at controlled room temperature for a period of at least 3 months.

7. INCORPORATION BY REFERENCE

Various references such as patents, patent applications, and publications are cited herein, the disclosures of which are hereby incorporated by reference herein in their entireties.

What is claimed is:
1. A composition comprising 3,3'-diindolylmethane ("DIM") as the biologically active agent and a carrier of said active agent, wherein the carrier comprises:
   (i) an essential oil, wherein the essential oil is peppermint oil, tea tree oil, wintergreen oil, lemon oil, lime oil, lavender oil, ginger oil, nutmeg oil, fennel oil, *eucalyptus* oil, rosemary oil, pomegranate seed oil, black cumin oil, clove oil, mustard oil, or cinnamon bark oil,
   (ii) a lauroyl polyoxyl-32 glyceride,
   (iii) propylene glycol caprylate,
   (iv) polysorbate 80 or tocopherol PEG 1000 succinate, and
   (v) a lecithin;
   wherein the composition, upon dispersion in water or contact with gastrointestinal fluids, emulsifies to form a dispersion of oil-in-water globules.
2. The composition of claim 1, wherein the essential oil is peppermint oil, lavender oil, ginger oil, nutmeg oil, fennel oil, *eucalyptus* oil, rosemary oil, black cumin oil, mustard oil, or pomegranate seed oil.
3. The composition of claim 1, wherein the lecithin is phosphatidyl choline or an excipient enriched in phosphatidyl choline.
4. The composition of claim 3, wherein the phosphatidyl choline is a phosphatidyl choline preparation from soy or sunflower oil.
5. The composition of claim 1, which comprises tocopherol PEG 1000 succinate in item (iv), and wherein the essential oil is rosemary oil.
6. The composition of claim 1, which comprises tocopherol PEG 1000 succinate in item (iv), and wherein the essential oil is peppermint oil.

7. The composition of claim 1, which comprises polysorbate 80 in item (iv), and wherein the essential oil is rosemary oil, and the lecithin is phosphatidyl choline.

8. The composition of claim 1, which comprises polysorbate 80 in item (iv), and wherein the essential oil is peppermint oil, and the lecithin is phosphatidyl choline.

9. The composition of claim 1, which further comprises a retinoid.

10. The composition of claim 9, wherein the retinoid is retinyl palmitate.

11. The composition of claim 10, which further comprises Vitamin D.

12. The composition of claim 1, which further comprises melatonin.

13. The composition of claim 1, which further comprises Vitamin K2, wherein Vitamin K2 is menaquinone-7.

14. The composition of claim 1, which further comprises Vitamin D.

15. The composition of claim 1, which further comprises Vitamin K2 and Vitamin D.

16. The composition of claim 1, which further comprises ursolic acid, plumbagin or curcumin.

17. The composition of claim 1, wherein the DIM in the composition is in an amount from 5% to 20% by weight.

18. The composition of claim 17, wherein the DIM in the composition is in an amount of at least 10% by weight.

19. The composition of claim 1, wherein at least 50% of the globules are less than 1.5 μm in diameter, or wherein the globules have a mean particle size of less than 1.5 μm in diameter; and wherein the size of the particles is determined by in vitro dispersion testing.

20. The composition of claim 1, which is formulated for oral administration.

21. The composition of claim 2, wherein the essential oil is peppermint oil, rosemary oil, ginger oil, or black cumin oil.

22. The composition of claim 20, which further comprises ethanol.

23. The composition of claim 1, which further comprises one or more of: ethanol, isopropanol, acetone, ethyl myristate, propylene glycol, diethylene glycol monoethyl ether, and caprylocaproyl polyoxyl-8 glyceride; wherein the composition is formulated for topical administration.

24. A method for treating acne in a human subject in need thereof comprising administering the composition of claim 1 to the subject.

25. The method of claim 24 comprising further co-administering retinyl palmitate to the subject.

26. The method of claim 24, wherein the administering is topical, and wherein the composition is formulated as a wash, a scrub, a shampoo, or a cosmetic or hygiene product for use with water or administration to a wet surface.

27. A method for treating atopic dermatitis in a mammal in need thereof comprising administering the composition of claim 1 to the subject.

28. The method of claim 27, wherein the administering is topical, and wherein the composition is formulated as a wash, a scrub, a shampoo, or a cosmetic or hygiene product for use with water or administration to a wet surface.

* * * * *